(12) United States Patent
Blagg

(10) Patent No.: US 9,169,234 B2
(45) Date of Patent: Oct. 27, 2015

(54) SEPIAPTERIN REDUCTASE INHIBITORS FOR THE TREATMENT OF PAIN

(75) Inventor: Julian Blagg, Surrey (GB)

(73) Assignee: Children's Medical Center Corporation, Boston, MA (US)

( * ) Notice: Subject to any disclaimer, the term of this patent is extended or adjusted under 35 U.S.C. 154(b) by 156 days.

(21) Appl. No.: 13/501,932

(22) PCT Filed: Oct. 14, 2010

(86) PCT No.: PCT/US2010/052674
§ 371 (c)(1),
(2), (4) Date: Jun. 27, 2012

(87) PCT Pub. No.: WO2011/047156
PCT Pub. Date: Apr. 21, 2011

(65) Prior Publication Data
US 2012/0322800 A1 Dec. 20, 2012

Related U.S. Application Data

(60) Provisional application No. 61/252,013, filed on Oct. 15, 2009.

(51) Int. Cl.
C07D 209/14 (2006.01)
A61K 31/4045 (2006.01)
C07D 401/12 (2006.01)
C07D 413/12 (2006.01)
C07D 209/12 (2006.01)
C07D 209/16 (2006.01)
C07D 209/18 (2006.01)

(52) U.S. Cl.
CPC ............ *C07D 401/12* (2013.01); *C07D 209/12* (2013.01); *C07D 209/14* (2013.01); *C07D 209/16* (2013.01); *C07D 209/18* (2013.01); *C07D 413/12* (2013.01)

(58) Field of Classification Search
CPC .......................... C07D 209/14; A61K 31/4045
USPC .................................. 548/504; 514/415, 419
See application file for complete search history.

(56) References Cited

U.S. PATENT DOCUMENTS

| 5,861,425 | A | 1/1999 | Audia et al. |
| 6,593,331 | B2 | 7/2003 | Camborde et al. |
| 7,906,520 | B2 | 3/2011 | Woolf et al. |
| 2005/0197341 | A1 | 9/2005 | Woolf et al. |
| 2008/0287452 | A1 | 11/2008 | Bursavich |
| 2009/0163545 | A1 | 6/2009 | Goldfarb |

FOREIGN PATENT DOCUMENTS

| DE | 3613623 | 10/1987 |
| WO | 95022524 | 8/1995 |
| WO | 01015686 | 3/2001 |
| WO | 02050031 | 6/2002 |
| WO | 03000180 | 1/2003 |
| WO | 2004043899 | 5/2004 |
| WO | 2004071445 | 8/2004 |
| WO | 2005048926 | 6/2005 |
| WO | 2006061638 | 6/2005 |
| WO | 2007021682 | 2/2007 |
| WO | 2007063010 | 6/2007 |
| WO | 2007066784 | 6/2007 |
| WO | 2007101863 | 9/2007 |
| WO | 2007140317 | 12/2007 |
| WO | 2008006583 | 1/2008 |
| WO | 2008019357 | 2/2008 |
| WO | 2008047883 | 4/2008 |
| WO | 2008049997 | 5/2008 |
| WO | 2008073825 | 6/2008 |
| WO | 2008157740 | 12/2008 |

OTHER PUBLICATIONS

Isojima, et al. Document No. 152:6936, CAPLUS, retrieved on Jul. 1, 2013.*
Talley, et al. Document No. 148:239024 retrieved from CAPLUS; Feb. 15, 2008.*
Kalgutkar, et al. Document No. 134:207711 retrieved from CAPLUS; Mar. 9, 2001.*
Bodor. Document No. 112:7383, retrieved from CAPLUS; Jan. 6, 1990.*
Cao, et al. Document No. 149:215106, retrieved from CAPLUS; Jun. 22, 2008.*
Lesieur, et al. Document No. 118:254750, retrieved from CAPLUS; Jun. 26, 1993,.*
Mansfiedl, et al. Document No. 146:163002, retrieved from CAPLUS; Jan. 18, 2007.*
Peng, et al. Document No. 140:93919, retrieved from CAPLUS; Jan. 28, 2004.*
Szumilo, et al. Document No. 116:165678, retrieved from CAPLUS; May 3, 1992.*
Tkachenko, et al. Document No. 147:181575, retrieved from CAPLUS; Jul. 27, 2007.*
Yamazaki, et al. Document No. 151:336915, retrieved from CAPLUS; Jul. 14, 2009.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

(Continued)

Primary Examiner — Shawquia Jackson
(74) Attorney, Agent, or Firm — Pabst Patent Group LLP

(57) ABSTRACT

Disclosed herein are small molecule heterocyclic inhibitors of sepiapterin reductase (SPR), and prodrugs and pharmaceutically acceptable salts thereof. The Also featured are pharmaceutical compositions of the compounds and uses of these compounds for the treatment or prevention of pain (e.g., inflammatory pain, nociceptive pain, functional pain, and neuropathic pain).

16 Claims, 1 Drawing Sheet

(56) References Cited

OTHER PUBLICATIONS

Auerbach, et al., "The 1.25 a crystal structure of sepiapterin reductase reveals its binding mode to pterins and brain neurotransmitters", EMBO J., 16:7219-30 (1997).
Bennett, "An animal model of neuropathic pain: a review", Muscle Nerve, 16:1040-8 (1993).
Berge, at al., "Pharmaceutical salts", J. Pharm. Sci., 66:1-19 (1977).
Decosterd and Woolf, "Spared nerve injury: an animal model of persistent peripheral neuropathic pain", Pain, 87:149-58 (2000).
Judkins, et al., "A versatile synthesis of amidines from nitriles via amidoximes", Synthetic Communications 26(23):4351-67 (1996).
Katoh, et al., "Direct inhibition of brain sepiapterin reductase by a catecholamine and an indoleamine", Biochem. Biophys. Res. Commun.,105:75-81 (1982).
Kim and Chung, "An experimental model for peripheral neuropathy produced by segmental spinal nerve ligation in the rat", Pain, 50:355-63 (1992).
Seltzer, "A novel behavioral model of neuropathic pain disorders produced in rats by partial sciatic nerve injury", Pain, 43: 205-18 (1990).
Smith, at al., "New inhibitors of sepiapterin reductase. Lack of an effect of intracellular tetrahydrobiopterin depletion upon in vitro proliferation of two human cell lines", J. Biol. Chem. 267:5599-5607 (1992).
Stein, et al., "Unilateral inflammation of the hindpaw in rats as a model of prolonged noxious stimulation: alterations in behavior and nociceptive thresholds", Pharmacol. Bioche Behay., 31: 445-51(1988).
Tegeder, at al., "Gtp cyclohydrolase and tetrahydrobiopterin regulate pain sensitivity and persistence", Nature Medicine, 12:1269-77 (2006).
Thony, et al., "Tetrahydrobiopterin biosynthesis, regeneration and functions", Biochem. J. 347:1-16 (2000).
Woolf, et al., "Nerve growth factor contributes to the generation of inflammatory sensory hypersensitivity", Neurosci., 62: 327-31 (1994).
Du, et al., "A novel quantitative structure-activity relationship method to predict the affinities of MT3 melatonin binding site", Eu J Med. Chem., 43(12):2861-9 (2008).
Faust, et al., "7-substituted-melatonin and 7-substituted-1-methylmelatonin analogues: Effect of substituents on potency and binding affinity", Bioorg Med Chem., 15(13):4543-51 (2007).
Fujiwara, et al., "Synthetic studies on the fluorinated analogs for the putative oxindole-type metabolites of 5-halotryptamines", Heterocycles, 79:427-32 (2009).
Radogna, at al., "Rapid and transient stimulation of intracellular reactive oxygen species by melatonin in normal and tumor leukocytes", Toxic Appl. Pharmacol., 239(1):37-45 (2009).
Wei, et al., "Discovery of multitarget inhibitors by combining molecular docking with common pharmacophore matching", J Med. Chem., 51(24):7882-8 (2008).
McKew, et al., "Inhibition of cytosolic phospholipase A2alpha: hit to lead optimization", J. Med.Chem., 49(1):135-58 (2006).
Menciu, et al., "New N-(pyridin-4-yl)-(indol-3-yl)acetamides and propanamides as antiallergic agents", J. Med. Chem., 42(4):638-48 (1999).
Payne, et al., "Synthesis of highly methylated indole-3-acetic acids", J Chem. Engin. Data, 10(1):71-2 (1965).
Wooley, "Highly potent antimetabolites of serotonin with little serotonin-like action", Biochem Pharmacol., 3:51-9 (1959).

* cited by examiner

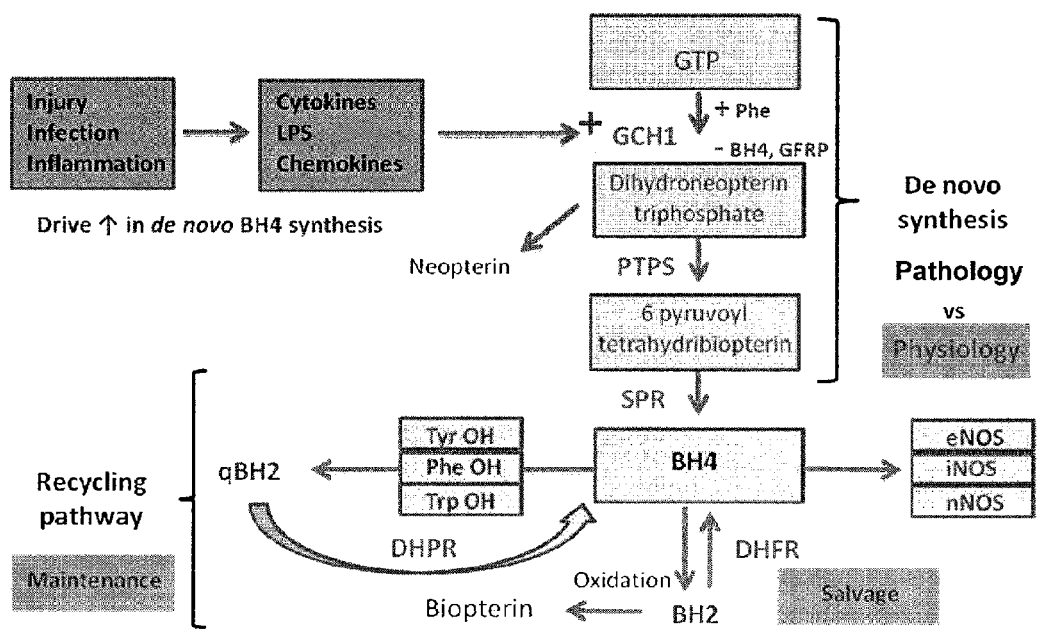

SEPIAPTERIN REDUCTASE INHIBITORS FOR THE TREATMENT OF PAIN

CROSS REFERENCE TO RELATED APPLICATIONS

This application is a filing under 35 U.S.C. §371 of PCT/US2010/052674 filed with the Patent Cooperation Treaty on Oct. 14, 2010, which claims priority to and benefit of U.S. Provisional Application No. 61/252,013, filed Oct. 15, 2009, all of which is herein incorporated in their entirety by reference.

BACKGROUND OF THE INVENTION

In general, the present invention relates to small molecule heterocyclic inhibitors of sepiapterin reductase (SPR), and to the medical use of these compounds.

Tetrahydrobiopterin (BH4), which has the following structure,

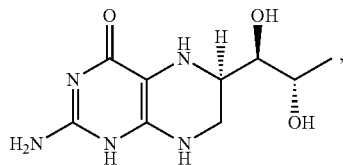 [SMILES: C[C@H](O)[C@H](O)[C@H]1CNc2[nH]c(N)nc(=O)c2N1]

is an essential cofactor of hydroxylase enzymes that are involved in the synthesis of neurotransmitters such as serotonin, melatonin, dopamine, norepinephrine (noradrenaline), epinephrine (adrenaline), and nitric oxide (NO). SPR catalyzes the final step in the BH4 synthetic pathway, which is the conversion of 6-pyruvoyl tetrahydropterin to BH4. SPR is also one of the two enzymes involved in de novo BH4 synthesis that is up-regulated in preclinical pain models, and reducing the activity of these enzymes leads to preclinical pain relief (Tegeder et al., *Nature Medicine* 12:1269-1277, 2006). Accordingly, the inhibition of SPR can be a useful target for developing new methods for the treatment or prevention of pain.

SUMMARY OF THE INVENTION

In general, in a first aspect, the invention features compounds having a structure according to Formula (I),

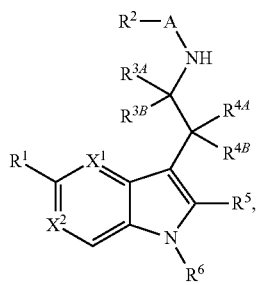

(I)

or a prodrug or pharmaceutically acceptable salt thereof, where each of $X^1$ and $X^2$ is, independently, N, C—H, or C-halogen;

A is a single bond, C(=O), or $SO_2$;

$R^1$ is $(CH_2)_n OR^{1A}$, halogen (e.g., F, Cl, Br, or I, preferably Cl), amino (e.g., $NH_2$), CN, $SO_2R^{1A}$, $NHSO_2R^{1A}$, NHC(=O)$R^{1A}$, or C(=O)N($R^{1A}$)$_2$;

each $R^{1A}$ is, independently, H or optionally substituted $C_{1-6}$ alkyl;

n is 0, 1, or 2;

$R^2$ is $CH_2OR^{2A}$, optionally substituted $C_{1-6}$ alkyl, optionally substituted $C_{3-9}$ cycloalkyl, optionally substituted aryl, optionally substituted heterocyclyl, or optionally substituted heteroaryl;

$R^{2A}$ is H or optionally substituted $C_{1-6}$ alkyl;

$R^{3A}$ and $R^{3B}$ are both H, or $R^{3A}$ and $R^{3B}$ combine to form =O;

$R^{4A}$ and $R^{4B}$ are both H, or $R^{4A}$ and $R^{4B}$ combine to form =O;

each of $R^5$ and $R^6$ is, independently, H, optionally substituted $C_{1-6}$ alkyl, optionally substituted $C_{3-10}$ cycloalkyl, optionally substituted alkaryl, or optionally substituted alkheteroaryl; and where when A is C(=O), $R^1$ is OH, $R^2$ is $CH_2OMe$, $R^{3A}$, $R^{3B}$, $R^{4A}$, and $R^{4B}$ are each H, and $R^5$ is H, $R^6$ is not H.

In some embodiments, one and only one of $R^{3A}$ and $R^{3B}$ and $R^{4A}$ and $R^{4B}$ can combine to form =O.

In other embodiments, one or both of $X^1$ and $X^2$ is C—H, or one or both of $X^1$ and $X^2$ is C—Cl.

In certain embodiments, $R^5$ and $R^6$ is, independently, H, branched $C_{1-6}$ alkyl, aminoalkyl, alkoxyalkyl, or haloalkyl.

In some embodiments, the compound has a structure according to Formula (I-A),

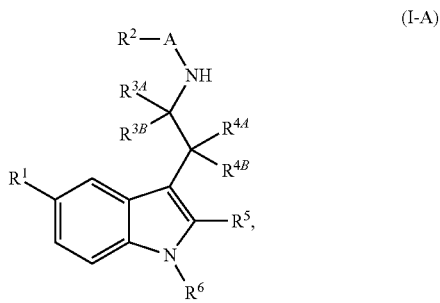

(I-A)

or a prodrug or pharmaceutically acceptable salt thereof, where $R^1$ is $(CH_2)_n OR^{1A}$, halogen, CN, $SO_2R^{1A}$, $NHSO_2R^{1A}$, or C(=O)N($R^{1A}$)$_2$; $R^5$ is H or optionally substituted $C_{1-6}$ alkyl; $R^6$ is H or optionally substituted $C_{1-6}$ alkyl; and where one and only one of $R^{3A}$ and $R^{3B}$ and $R^{4A}$ and $R^{4B}$ can combine to form =O.

In certain embodiments, $R^1$ is OH, $CH_2OH$, F, CN, $SO_2CH_3$, $NHSO_2CH_3$, or C(=O)$NH_2$.

In other embodiments, $R^2$ is $(CH_2)_m OR^{2B}$, wherein m is 1, 2, or 3, and $R^{2B}$ is H or optionally substituted $C_{1-6}$ alkyl.

In some embodiments, $R^5$ is H or $CH_3$.

In other embodiments, $R^6$ is H or $CH_3$.

In still other embodiments, $R^{3A}$, $R^{3B}$, $R^{4A}$, and $R^{4B}$ are each H.

In certain embodiments, $R^{3A}$ and $R^{3B}$ combine to form =O. In other embodiments, $R^{4A}$ and $R^{4B}$ combine to form =O.

In certain embodiments, the compound has a structure according to the following formula:

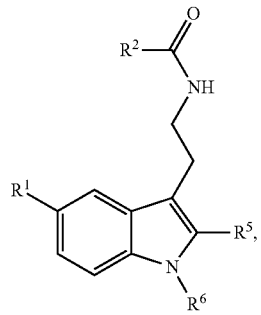
(I-B)

or a prodrug or pharmaceutically acceptable salt thereof, where $R^1$ is OH, $CH_2OH$, F, CN, $SO_2R^{1A}$, $NHSO_2R^{1A}$, or $C(=O)NH_2$; $R^{1A}$ is optionally substituted $C_{1-3}$ alkyl; $R^2$ is optionally substituted $C_{3-6}$ alkyl, optionally substituted $C_{3-6}$ cycloalkyl, optionally substituted 5-6 membered heterocyclyl, or optionally substituted heteroaryl; $R^5$ is H or $CH_3$; and $R^6$ is H or optionally substituted $C_{1-3}$ alkyl.

In some embodiments, the compound of Formula (I) has the following structure:

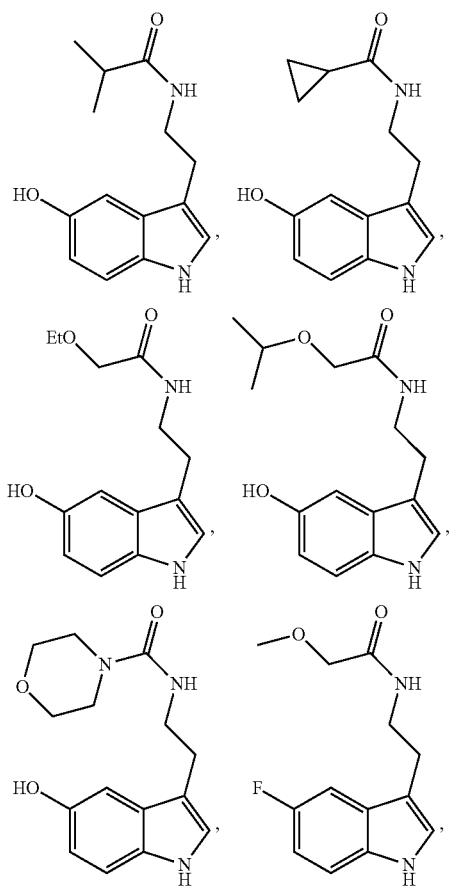

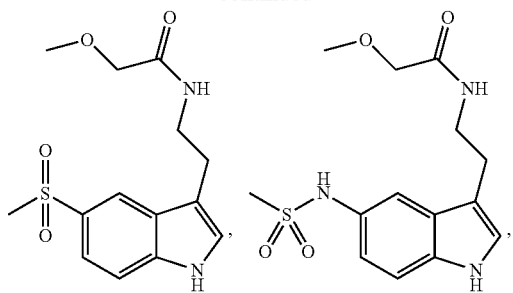

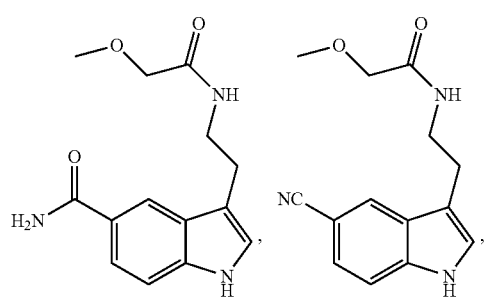

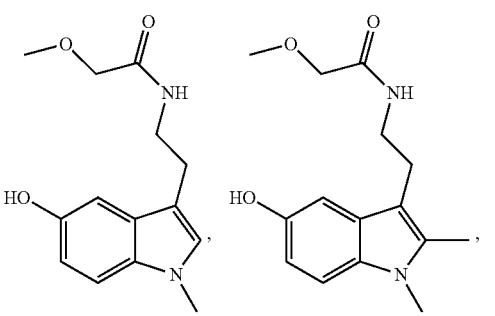

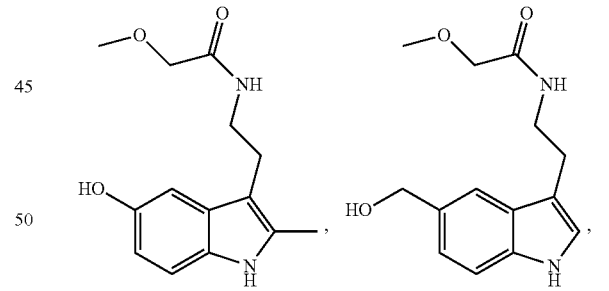

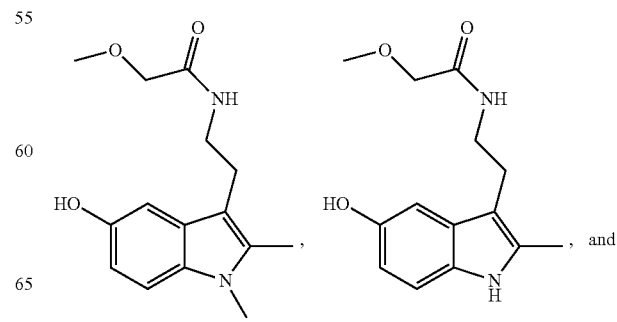
and

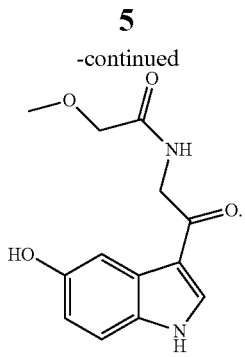

In some embodiments, the compound has a structure according to the following formula:

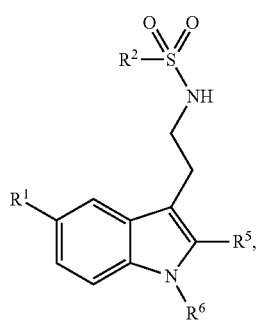

(I-C)

or a prodrug or pharmaceutically acceptable salt thereof, where $R^1$ is OH, $CH_2OH$, F, CN, $SO_2R^{1A}$, $NHSO_2R^{1A}$, or $C(=O)NH_2$; $R^{1A}$ is optionally substituted $C_{1-3}$ alkyl; $R^2$ is optionally substituted $C_{1-6}$ alkyl or optionally substituted $C_{3-6}$ cycloalkyl; $R^5$ is H or $CH_3$; and $R^6$ is H or optionally substituted $C_{1-3}$ alkyl. In some embodiments, $R^1$ is OH, and $R^5$, and $R^6$ are each H. In some embodiments, the compound is selected from the group consisting of:

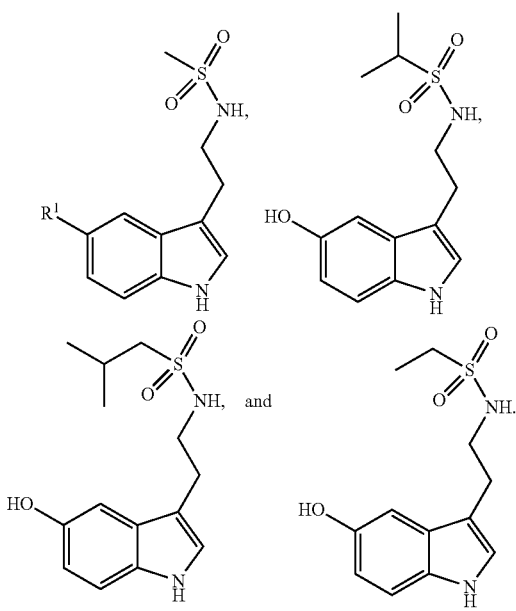

In still other embodiments, the compound has a structure according to the following formula:

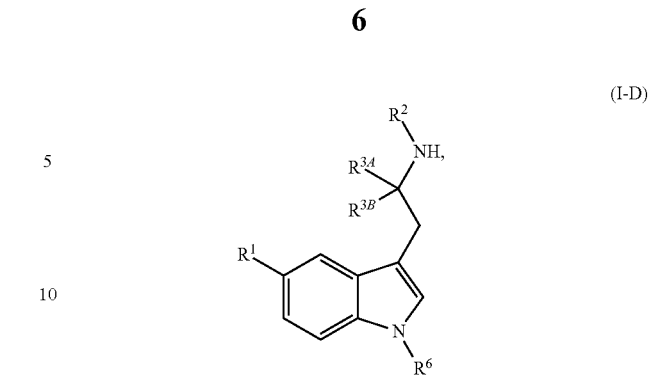

(I-D)

or a prodrug or pharmaceutically acceptable salt thereof, where $R^1$ is OH, $CH_2OH$, F, CN, $SO_2R^{1A}$, $NHSO_2R^{1A}$, or $C(=O)NH_2$; $R^{1A}$ is optionally substituted $C_{1-3}$ alkyl; $R^2$ is optionally substituted $C_{1-6}$ alkyl or optionally substituted heteroaryl; and $R^6$ is H or optionally substituted $C_{1-3}$ alkyl. In some embodiments, $R^1$ is OH and $R^6$ is H. In other embodiments, $R^2$ is optionally substituted pyridyl or $C_{1-3}$ alkyl that includes a $C_{1-2}$ alkoxy substituent. In some embodiments, the compound is selected from the group consisting of

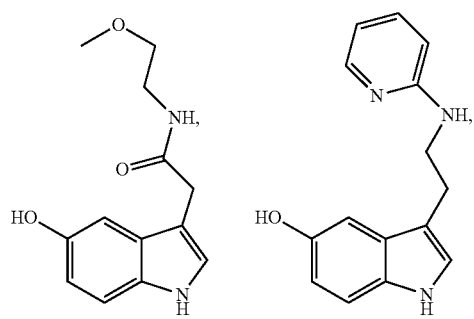

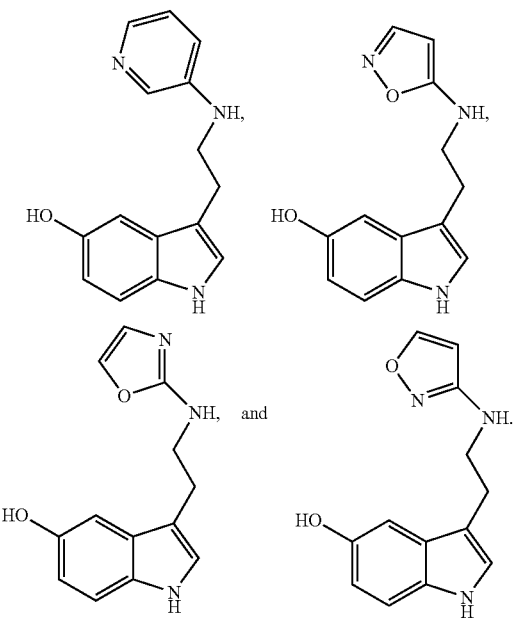

In a second aspect, the invention features further compounds having a structure according to Formula (II),

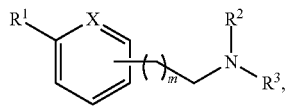

(II)

or a prodrug or pharmaceutically acceptable salt thereof, where

X is N or CH;

m is 0 or 1;

$R^1$ is $(CH_2)_nOR^{1A}$, halogen, CN, amino (e.g., $NH_2$), $SO_2R^{1A}$, $NHSO_2R^{1A}$, $NHC(=O)R^{1A}$, or $C(=O)N(R^{1A})_2$;

each $R^{1A}$ is, independently, H or optionally substituted $C_{1-6}$ alkyl;

n is 0, 1, or 2;

$R^2$ is H or optionally substituted $C_{1-3}$ alkyl;

$R^3$ is H, $C(=O)R^{3A}$, or $SO_2R^{3A}$; and $R^{3A}$ is optionally substituted $C_{1-6}$ alkyl.

In some embodiments, the compound has a structure according to any of the following formulas:

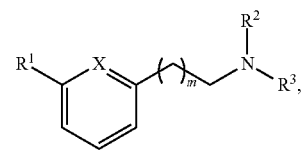

(II-A)

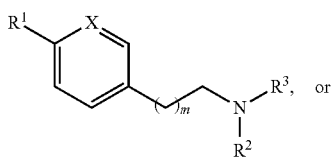

(II-B)

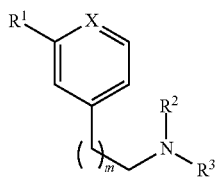

(II-C)

or a prodrug or pharmaceutically acceptable salt thereof. In certain embodiments, X is N, m is 1, and $R^2$ is H. In other embodiments, $R^1$ is amino. In some embodiments, $R^3$ is $C(=O)R^{3A}$, and $R^{3A}$ is $C_{1-3}$ alkyl that includes a $C_{1-3}$ alkoxy substituent. In further embodiments the compound is

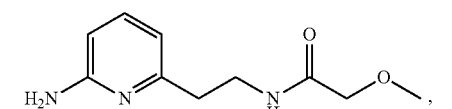

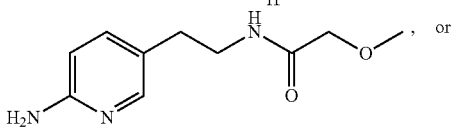, or

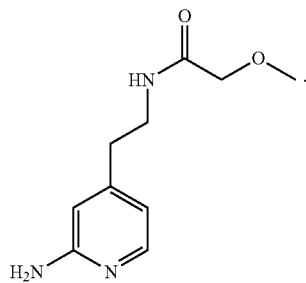

In some embodiments, X is CH, m is 1, and $R^2$ is H. In other embodiments, $R^1$ is F, OH, CN, $CH_2OR^{1A}$, $SO_2R^{1A}$, $NHSO_2R^{1A}$, or $C(=O)NH_2$; and $R^{1A}$ is H or $C_{1-2}$ alkyl.

In still other embodiments, $R^3$ is H or $C(=O)R^{3A}$, and $R^{3A}$ is $C_{1-3}$ alkyl that includes a $C_{1-3}$ alkoxy substituent. In certain embodiments, the compound is selected from the group consisting of:

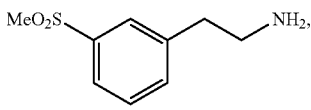

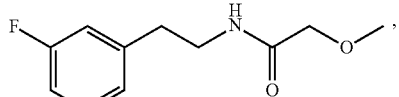

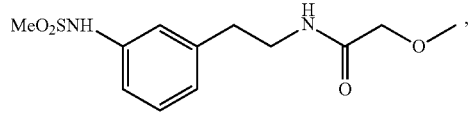

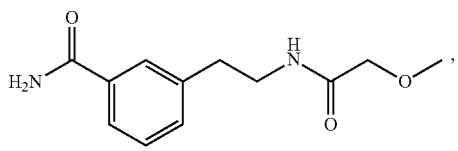

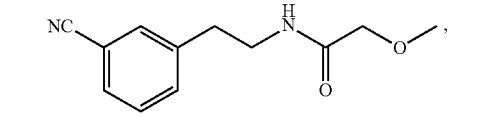

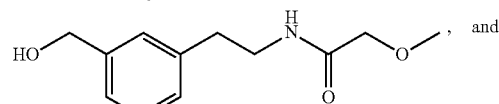, and

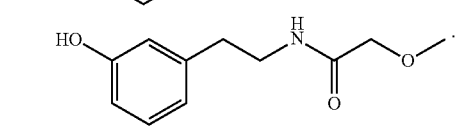

In some embodiments, $R^3$ is $SO_2R^{3A}$, and $R^{3A}$ is optionally substituted $C_{1-4}$ alkyl. In certain embodiments, the compound is selected from the group consisting of:

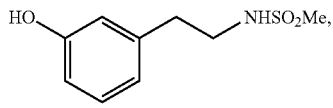

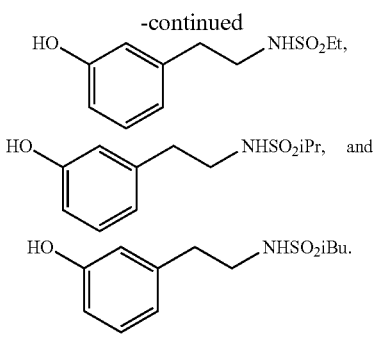

In any of the embodiments described herein (e.g., a compound of Formula (I) or (II)), the compound is an inhibitor of Sepiapterin Reductase (SPR).

In a related aspect, the invention relates to a pharmaceutical composition that includes any of the compounds (e.g., in an effective amount) described herein (e.g., a compound of Formula (I) or (II), or any of Compounds (1)-(39)), or a tautomer, prodrug, or pharmaceutically acceptable salt thereof, and a pharmaceutically acceptable excipient. The pharmaceutical composition may include an effective amount of the compound (e.g., a compound of Formula (I) or (II), or any of Compounds (1)-(39)), or a tautomer, prodrug, or pharmaceutically acceptable salt thereof.

In another related aspect, the invention relates to a method of treating, reducing, or preventing a condition in a mammal, wherein the method includes the administration of any of the compounds described herein (e.g., a compound of Formula (I) or (II), or any of Compounds (1)-(39)), or a tautomer, prodrug, or pharmaceutically acceptable salt thereof, or a pharmaceutical composition thereof, to the mammal in a dosage sufficient to inhibit SPR. In one embodiment, the condition is pain. The pain may be neuropathic, inflammatory, nociceptive, or functional pain. Further, the pain may be chronic or acute.

Finally, the invention relates to a method of inhibiting SPR in a cell, involving contacting a cell with any of the compounds described herein (e.g., a compound of Formula (I) or (II), or any of Compounds (1)-(39)), or a tautomer, prodrug, or pharmaceutically acceptable salt thereof.

The term "$C_{x-y}$ alkaryl," as used herein, represents a chemical substituent of formula —RR', where R is an alkylene group of x to y carbons and R' is an aryl group as defined herein. Similarly, by the term "$C_{x-y}$ alkheteroaryl" is meant a chemical substituent of formula —RR", where R is an alkylene group of x to y carbons and R" is a heteroaryl group as defined herein. Other groups preceded by the prefix "alk-" are defined in the same manner. Exemplary unsubstituted alkaryl groups are of from 7 to 16 carbons.

The term "alkcycloalkyl" represents a cycloalkyl group attached to the parent molecular group through an alkylene group.

The terms "alkenyl" or "$C_{2-6}$ alkenyl," as used herein, represent monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like. A substituted $C_{2-6}$ alkenyl may have, for example, 1, 2, 3, 4, 5, or 6 substituents located at any position.

The term "alkheterocyclyl" represents a heterocyclic group attached to the parent molecular group through an alkylene group. Exemplary unsubstituted alkheterocyclyl groups are of from 2 to 14 carbons.

The term "alkoxy" represents a chemical substituent of formula —OR, where R is an optionally substituted alkyl group of 1 to 6 carbons, unless otherwise specified (e.g., "$C_{1-3}$ alkoxy" refers to alkoxy groups including a $C_{1-3}$ alkyl group), where the optionally substituted alkyl may be branched, linear, or cyclic. The $C_{1-6}$ alkyl may be substituted or unsubstituted. A substituted $C_{1-6}$ alkyl can have, for example, 1, 2, 3, 4, 5, or 6 substituents located at any position. Exemplary alkoxy groups include, but are not limited to, methoxy, ethoxy, propoxy, isopropoxy, tert-butoxy, and the like.

The term "alkoxyalkyl" represents an alkyl group that is substituted with an alkoxy group. Exemplary unsubstituted alkoxyalkyl groups include between 2 to 12 carbons. In some embodiments, the alkyl and the alkoxy each can be further substituted with 1, 2, 3, or 4 substituent groups as defined herein for the respective group.

The terms "alkyl" and the prefix "alk-," as used herein, are inclusive of both straight chain and branched chain saturated groups of from 1 to 6 carbons, unless otherwise specified (e.g., "$C_{1-4}$ alkyl" refers to alkyl groups having 1-4 carbons).

Alkyl groups are exemplified by methyl, ethyl, n- and iso-propyl, n-, sec-, iso- and tert-butyl, neopentyl, and the like, and may be optionally substituted. Exemplary substituted alkyl groups include, but are not limited to, alkaryl, alkoxyalkyl, aminoalkyl, and haloalkyl (e.g., perfluoroalkyl) groups, as defined herein.

The term "alkylene," as used herein, represents a saturated divalent hydrocarbon group derived from a straight or branched chain saturated hydrocarbon by the removal of two hydrogen atoms, and is exemplified by methylene (—$CH_2$—), ethylene (—$CH_2CH_2$—), isopropylene, and the like.

By "amino" is meant a group having a structure —NR'R", where each R' and R" is selected, independently, from H, optionally substituted $C_{1-6}$ alkyl, optionally substituted cycloalkyl, optionally substituted heterocyclyl, optionally substituted aryl, optionally substituted heteroaryl, or R' and R" combine to form an optionally substituted heterocyclyl. When R' is not H or R" is not H, R' and R" may be unsubstituted or substituted with, for example, 1, 2, 3, 4, 5, or 6 substituents.

The term "aminoalkyl" or "$C_{1-6}$ alkylamino," as used herein, represents an alkyl group, as defined herein, substituted by an amino group, as defined herein. The alkyl and amino each can be further substituted with 1, 2, 3, or 4 substituent groups as described herein for the respective group.

By "aryl" is meant is an optionally substituted $C_6$-$C_{10}$ cyclic group with [4n+2] π electrons in conjugation and where n is 1, 2, or 3. Non-limiting examples of aryls include heteroaryls and, for example, benzene and naphthalene. Aryls also include bi- and tri-cyclic ring systems in which a non-aromatic saturated or partially unsaturated carbocyclic ring (e.g., a cycloalkyl or cycloalkenyl) is fused to an aromatic ring such as benzene or naphthalene. Exemplary aryls fused to a non-aromatic ring include indanyl and tetrahydronaphthyl. Any aryls as defined herein may be unsubstituted or substituted. A substituted aryl may be optionally substituted with, for example, 1, 2, 3, 4, 5, or 6 substituents located at any position of the ring.

By "cycloalkyl" is meant an optionally substituted, saturated or partially unsaturated 3- to 10-membered monocyclic or polycyclic (e.g., bicyclic, or tricyclic) hydrocarbon ring system. Where a cycloalkyl is polycyclic, the constituent cycloalkyl rings may be fused together, form a spirocyclic structure, or the polycyclic cycloalkyl may be a bridged cycloalkyl (e.g., adamantyl or norbonanyl). Exemplary cycloalkyls include cyclopropyl, cyclobutyl, cyclopentyl, cyclohexyl, and cycloheptyl. Cycloalkyls may be unsubstituted or substituted. A substituted cycloalkyl can have, for example, 1, 2, 3, 4, 5, or 6 substituents.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted The term an "effective amount" of a compound (e.g., any of Compounds (1)-(39) or a compound according to Formula (I) or (II)), as used herein, is that amount sufficient to effect beneficial or desired results, such as clinical results, and, as such, an "effective amount" depends upon the context in which it is being applied. For example, in the context of administering an agent that inhibits SPR, an effective amount of an agent is, for example, an amount sufficient to achieve a reduction in SPR activity as compared to the response obtained without administration of the agent and thereby prevents, reduces, or eliminates the sensation of pain. The effective amount of active compound(s) used to practice the present invention for therapeutic treatment of pain also varies depending upon the manner of administration, the age, and body weight, of the subject as well as the underlying pathology that is causing the pain. Ultimately, the attending physician or veterinarian will decide the appropriate amount and dosage regimen.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. In some embodiments, the haloalkyl group can be further substituted with 1, 2, 3, or 4 substituent groups as described herein for alkyl groups. Haloalkyl groups include perfluoroalkyls.

By "halogen" or "halo" is meant fluorine (—F), chlorine (—Cl), bromine (—Br), or iodine (—I).

The term "heteroaryl," as used herein, represents that subset of heterocycles, as defined herein, which are aromatic: i.e., they contain 4n+2 pi electrons within the mono- or multicyclic ring system. Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, benzoxazole, isoxazole, isothiazole, pyrazole, thiazole, benzthiazole, triazole (e.g., 1,2,4-triazole or 1,2,3-triazole), benzotriazole, pyridines, pyrimidines, pyrazines, quinoline, isoquinoline, purine, pyrazine, pteridine, triazine (e.g, 1,2,3-triazine, 1,2,4-triazine, or 1,3,5-triazine)indoles, 1,2,4,5-tetrazine, benzo[b]thiophene, benzo[c]thiophene, benzofuran, isobenzofuran, and benzimidazole. Heteroaryls may be unsubstituted or substituted. Substituted heteroaryls can have, for example, 1, 2, 3, 4, 5, or 6 substituents.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocyclyl" also represents a heterocyclic compound having a bridged multi-cyclic structure in which one or more carbons and/or heteroatoms bridges two non-adjacent members of a monocyclic ring, e.g., a quinuclidinyl group. The term "heterocycle" includes bicyclic, tricyclic and tetracyclic groups in which any of the above heterocyclic rings is fused to one, two, or three rings, e.g., an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Examples of fused heterocycles include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Any of the heterocycle groups mentioned herein may be optionally substituted with one, two, three, four or five substituents The term "hydroxyl," as used herein, represents an —OH group.

The term "nitrile," as used herein, represents a —CN group.

By "pain" is meant all types of pain including inflammatory pain, nociceptive pain, functional pain, and neuropathic pain (peripheral and central), whether acute or chronic. Exemplary, non-limiting types of pain that can be treated according to the methods described herein include musculoskeletal pain (after trauma, infections, and exercise), neuropathic pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative pain. Pain can also be associated with conditions that include, for example, soft tissue, joint, bone inflammation and/or damage (e.g., acute trauma, osteoarthritis, or rheumatoid arthritis), myofascial pain syndromes (fibromyalgia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures).

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "pharmaceutical composition," as used herein, represents a composition containing a compound (e.g., an effective amount of the compound) described herein (e.g., any of Compounds (1)-(39) or a compound according to Formula (I) or (II)), formulated with a pharmaceutically acceptable excipient, and typically manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The terms "pharmaceutically acceptable solvate" or "solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prevent," as used herein, refers to prophylactic treatment or treatment that prevents one or more symptoms or conditions of a disease, disorder, or conditions described herein such as pain (e.g. neuropathic or inflammatory pain). Preventative treatment can be initiated, for example, prior to ("pre-exposure prophylaxis") or following ("post-exposure prophylaxis") an event that precedes the onset of the disease, disorder, or conditions. Preventive treatment that includes administration of a compound of the invention, or a pharmaceutical composition thereof, can be acute, short-term, or chronic. The doses administered may be varied during the course of preventative treatment.

The term "prodrug," as used herein, represents compounds which are rapidly transformed in vivo to the parent compound of the above formula (e.g., any of Compounds (1)-(39) or a compound according to Formula (I) or (II)), for example, by hydrolysis in blood. Prodrugs of the compounds of the invention may be conventional esters. Some common esters which have been utilized as prodrugs are phenyl esters, aliphatic ($C_7$-$C_8$ or $C_8$-$C_{24}$) esters, cholesterol esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are pharmaceutically acceptable.

The term "thioether," as used herein, refers to a C—SR group, where R is an unsubstituted alkyl or a substituted alkyl (e.g., an alkaryl group that may be further substituted) as described herein.

The term "thiol," as used herein, refers to the —SH group.

The term "thiooxo," as used herein, refers to a C=S group, where a carbon atom is double-bonded to sulfur.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. As compared with an equivalent untreated control, such a reduction of pain is at least a 5%, 10%, 20%, 40%, 50%, 60%, 80%, 90%, 95%, or 100% reduction as measured by any standard technique known in the art. To treat pain, according to the methods of this invention, the treatment does not necessarily provide therapy for the underlying pathology that is causing the painful sensation. Treatment of pain can be purely symptomatic.

Any of the groups described herein can be substituted or unsubstituted. Where a group is substituted, the group may be substituted with 1, 2, 3, 4, 5, or 6 substituents. Optional substituents include, but are not limited to: $C_{1-6}$ alkyl, $C_{2-6}$ alkenyl, $C_{2-6}$ alkynyl, cycloalkyl, cycloalkenyl, heterocyclyl, aryl, heteroaryl, halogen; azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O) OR'), hydroxy (—OH), isocyano (—NC), sulfonate (—S(=O)$_2$OR), sulfonamide (—S(=O)$_2$NRR' or —NRS(=O)$_2$R), or sulfonyl (—S(=O)$_2$R), where each R or R' is selected, independently, from H, $C_{1-6}$ alkyl, $C_{2-6}$ alkenyl, $C_{2-6}$ alkynyl, cycloalkyl, heterocyclyl, aryl, or heteroaryl. A substituted group may have, for example, 1, 2, 3, 4, 5, 6, 7, 8, or 9 substituents. In some embodiments, each hydrogen in a group may be replaced by a substituent group (e.g., perhaloalkyl groups such as —$CF_3$ or —$CF_2CF_3$ or perhaloaryls such as —$C_6F_5$). In other embodiments, a substituent group may itself be further substituted by replacing a hydrogen of the substituent group with another substituent group such as those described herein. Substituents may be further substituted with, for example, 1, 2, 3, 4, 5, or 6 substituents as defined herein. For example, a lower $C_{1-6}$ alkyl or an aryl substituent group (e.g., heteroaryl, phenyl, or naphthyl) may be further substituted with 1, 2, 3, 4, 5, or 6 substituents as described herein.

Asymmetric or chiral centers may exist in any of the compounds of the present invention. The present invention contemplates the various stereoisomers and mixtures thereof. Individual stereoisomers of compounds of the present invention are prepared synthetically from commercially available starting materials that contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Alternatively, chiral compounds can be prepared by an asymmetric synthesis that favors the preparation of one enantiomer over the other. Alternatively a chiral pool synthesis (starting with an enantiomerically pure building block) can be used wherein the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively. In other cases, diastereomeric isomers such as cis and trans isomers may be separated by column chromatography, chiral chromatography, or recrystallization. In some cases, derivatization can improve the separation of these mixtures.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration. It is also recognized that for structures in which tautomeric forms are possible, the description of one tautomeric form is equivalent to the description of both, unless otherwise specified.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages of the invention will be apparent from the following Detailed Description, the drawings, and the claims.

BRIEF DESCRIPTION OF THE DRAWING

FIG. 1 is a schematic of BH4 biosynthesis and control. BH4 is synthesized de novo from guanosine triphosphate (GTP) in three steps mediated by GTP cyclohydrolase (GCH-1), 6-pyruvoyltetrahydriobiopterin synthase (PTPS), and sepiapterin reductase (SPR). BH4 is also generated by a separate recycling pathway that converts quinoid BH4 or BH2 to BH4 via enzymatic reduction.

DETAILED DESCRIPTION

In general, the invention relates to compounds according to Formulas (I) and (II), or a tautomer, prodrug, or pharmaceutically acceptable salt thereof, or a pharmaceutical composition thereof, and the use of these compounds and compositions in methods of treatment or to inhibit sepiapterin reductase (SPR).

Compounds of Formula (I) have the following structure

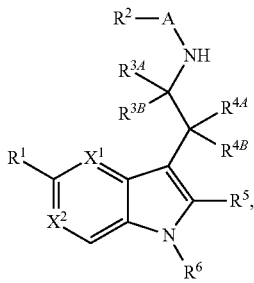
(I)

or a tautomer, prodrug, or pharmaceutically acceptable salt thereof, where each of $X^1$ and $X^2$ is, independently, N, C—H, or C-halogen;

A is a single bond, C(=O), or SO$_2$;

$R^1$ is $(CH_2)_nOR^{1A}$, halogen (e.g., F, Cl, Br, or I, preferably Cl), amino (e.g., NH$_2$), CN, SO$_2R^{1A}$, NHSO$_2R^{1A}$, NHC(=O)R$^{1A}$, or C(=O)N(R$^{1A}$)$_2$;

each $R^{1A}$ is, independently, H or optionally substituted C$_{1-6}$ alkyl; n is 0, 1, or 2;

$R^2$ is CH$_2$OR$^{2A}$, optionally substituted C$_{1-6}$ alkyl, optionally substituted C$_{3-9}$ cycloalkyl, optionally substituted aryl, optionally substituted heterocyclyl, or optionally substituted heteroaryl;

$R^{2A}$ is H or optionally substituted C$_{1-6}$ alkyl;

$R^{3A}$ and $R^{3B}$ are both H, or $R^{3A}$ and $R^{3B}$ combine to form =O;

$R^{4A}$ and $R^{4B}$ are both H, or $R^{4A}$ and $R^{4B}$ combine to form =O;

each of $R^5$ and $R^6$ is, independently, H, optionally substituted C$_{1-6}$ alkyl, optionally substituted C$_{3-10}$ cycloalkyl, optionally substituted alkaryl, or optionally substituted alkheteroaryl; and where when A is C(=O), $R^1$ is OH, $R^2$ is CH$_2$OMe, $R^{3A}$, $R^{3B}$, $R^{4A}$, and $R^{4B}$ are each H, and $R^5$ is H, $R^6$ is not H.

In some embodiments, one and only one of $R^{3A}$ and $R^{3B}$ and $R^{4A}$ and $R^{4B}$ can combine to form =O.

Compounds of Formula (II) have the following structure:

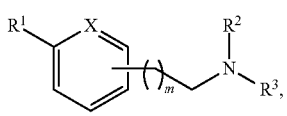
(II)

or a tautomer, prodrug, or pharmaceutically acceptable salt thereof, where

X is N or CH;

m is 0 or 1;

$R^1$ is $(CH_2)_nOR^{1A}$, halogen, CN, amino, SO$_2R^{1A}$, NHSO$_2R^{1A}$, NHC(=O)R$^{1A}$, or C(=O)N(R$^{1A}$)$_2$;

each $R^{1A}$ is, independently, H or optionally substituted C$_{1-6}$ alkyl;

n is 0, 1, or 2;

$R^2$ is H or optionally substituted C$_{1-3}$ alkyl;

$R^3$ is H, C(=O)R$^{3A}$, or SO$_2R^{3A}$; and $R^{3A}$ is optionally substituted C$_{1-6}$ alkyl.

Exemplary compounds of the invention, or a tautomer, prodrug, or pharmaceutically acceptable salt thereof, include those shown in Table 1.

TABLE 1

| No. | Structure |
| --- | --- |
| (1) | ![structure 1] |
| (2) | ![structure 2] |
| (3) | ![structure 3] |
| (4) | ![structure 4] |
| (5) | ![structure 5] |

TABLE 1-continued

| No. | Structure |
|---|---|
| (6) | N-(2-(5-hydroxy-1H-indol-3-yl)ethyl)methanesulfonamide |
| (7) | N-(2-(5-hydroxy-1H-indol-3-yl)ethyl)propane-2-sulfonamide |
| (8) | N-(2-(5-hydroxy-1H-indol-3-yl)ethyl)-2-methylpropane-1-sulfonamide |
| (9) | N-(2-(5-hydroxy-1H-indol-3-yl)ethyl)ethanesulfonamide |
| (10) | 2-(5-hydroxy-1H-indol-3-yl)-N-(2-methoxyethyl)acetamide |
| (11) | N-(2-(5-hydroxy-1H-indol-3-yl)ethyl)pyridin-2-amine |
| (12) | N-(2-(5-hydroxy-1H-indol-3-yl)ethyl)pyridin-3-amine |
| (13) | N-(2-(5-hydroxy-1H-indol-3-yl)ethyl)isoxazol-5-amine |
| (14) | N-(2-(5-hydroxy-1H-indol-3-yl)ethyl)oxazol-2-amine |
| (15) | N-(2-(5-hydroxy-1H-indol-3-yl)ethyl)isoxazol-3-amine |

TABLE 1-continued

| No. | Structure |
|---|---|
| (16) | 5-fluoro-tryptamine N-methoxyacetamide |
| (17) | 5-methylsulfonyl-tryptamine N-methoxyacetamide |
| (18) | 5-cyano-tryptamine N-methoxyacetamide |
| (19) | 5-cyano-tryptamine N-methoxyacetamide (isomer) |
| (20) | 5-carbamoyl-tryptamine N-methoxyacetamide |

TABLE 1-continued

| No. | Structure |
|---|---|
| (21) | 5-hydroxy-1-methyl-tryptamine N-methoxyacetamide |
| (22) | 5-hydroxy-1,2-dimethyl-tryptamine N-methoxyacetamide |
| (23) | 5-hydroxy-2-methyl-tryptamine N-methoxyacetamide |
| (24) | 5-hydroxy-indol-3-yl glyoxylamide N-methoxyacetamide |
| (25) | 5-hydroxymethyl-tryptamine N-methoxyacetamide |

TABLE 1-continued

| No. | Structure |
|---|---|
| (26) | 3-F-C6H4-CH2CH2-NH-C(O)-CH2-OMe |
| (27) | 3-(MeO2S)-C6H4-CH2CH2-NH2 · HCl |
| (28) | 3-(MeO2SNH)-C6H4-CH2CH2-NH-C(O)-CH2-OMe |
| (29) | 3-NC-C6H4-CH2CH2-NH-C(O)-CH2-OMe |
| (30) | 3-(H2NC(O))-C6H4-CH2CH2-NH-C(O)-CH2-OMe |
| (31) | 3-(HOCH2)-C6H4-CH2CH2-NH-C(O)-CH2-OMe |
| (32) | 3-HO-C6H4-CH2CH2-NH-C(O)-CH2-OMe |
| (33) | 6-amino-pyridin-2-yl-CH2CH2-NH-C(O)-CH2-OMe |
| (34) | 2-amino-pyridin-4-yl-CH2CH2-NH-C(O)-CH2-OMe |
| (35) | 6-amino-pyridin-3-yl-CH2CH2-NH-C(O)-CH2-OMe |
| (36) | 3-HO-C6H4-CH2CH2-NHSO2Me |

TABLE 1-continued

| No. | Structure |
|---|---|
| (37) | 3-HO-C6H4-CH2CH2-NHSO2Et |
| (38) | 3-HO-C6H4-CH2CH2-NHSO2iPr |
| (39) | 3-HO-C6H4-CH2CH2-NHSO2iBu |

Synthesis

The compounds described herein, e.g., any of Compounds (1)-(39) or a compound according to Formula (I) or (II), can be prepared according to methods known in the art. Exemplary methods include the following.

Synthesis Of Formula (I) Compounds

Compounds of Formula (I) can be synthesized by treating various 2-(1H-indol-3-yl)ethanamine starting materials with electrophiles as shown in Scheme 1.

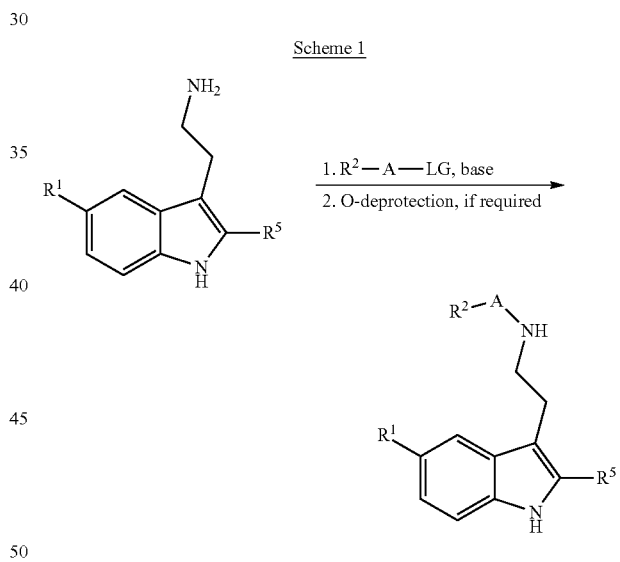

Scheme 1

In this scheme, $R^2$-A-LG is an electrophilic reagent, where $R^2$ and A are as defined for Formula (I) and LG is a leaving group. Suitable $R^2$-A-LG reagents include, but are not limited to, alkyl halides, alkyl sulfonates, acyl chlorides, carbonates, acyl anhydrides, and sulfonyl chlorides. Further exemplary reagents are described in the synthetic examples provided herein. In some embodiments, e.g., when $R^1$ is OH, it may be desirable to selectively deprotect this group (e.g., deacylate any acyl esters that may have formed). Such transformations can be accomplished using methods known in the art, e.g., deprotection under basic conditions, or those described in Greene, *Protective Groups In Organic Synthesis*, 3$^{rd}$ Edition (John Wiley & Sons, New York, 1999), which is incorporated herein by reference.

Compounds of Formula (I) can also be prepared from other indole starting materials, as shown in Scheme 2.

Scheme 2

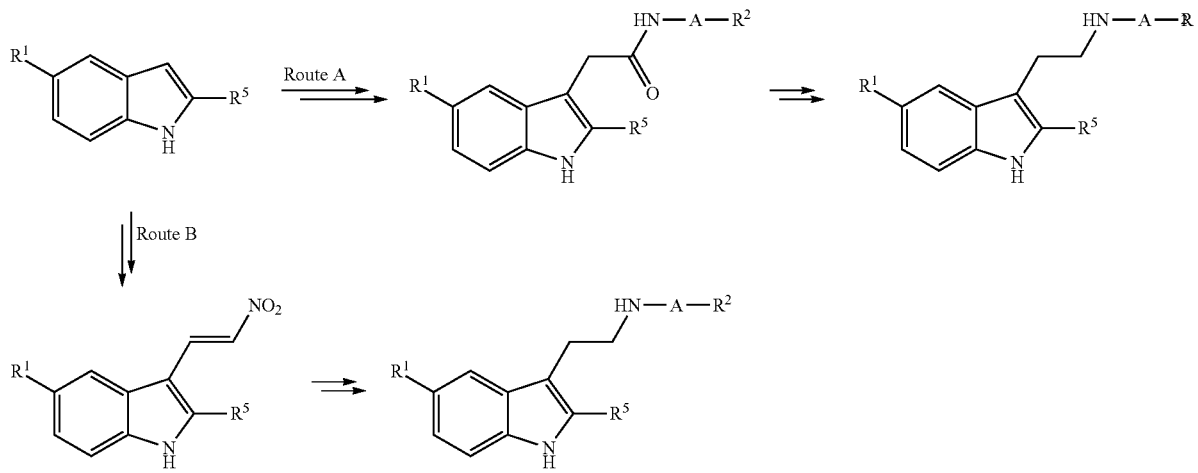

Using Route A, an indole compound can be elaborated to the corresponding 3-carboxamido intermediate (see, for example, the synthetic protocols for Compounds (10)-(12)). If desired, the carbonyl can be treated under reducing conditions to afford a saturated linking group.

When $R^1$ is an electron-withdrawing group, Route B can be used. Accordingly, the indole starting material is olefinated to form the corresponding nitro-alkene intermediate. Reduction of the nitro group to an amino group followed by treatment with an electrophile $R^2$-A-LG, as described for Scheme 1, can afford still other compounds of Formula (I). If desired, the indole compound can be N-alkylated using an electrophilic reagent such as $R^6$-LG, where $R^6$ is as defined for Formula (I) and LG is a leaving group.

Compounds of Formula (I) can also be prepared by the cyclization of arylhydrazine starting materials as shown in Scheme 3 (see, for example, the synthesis of Compound (17)).

Scheme 3

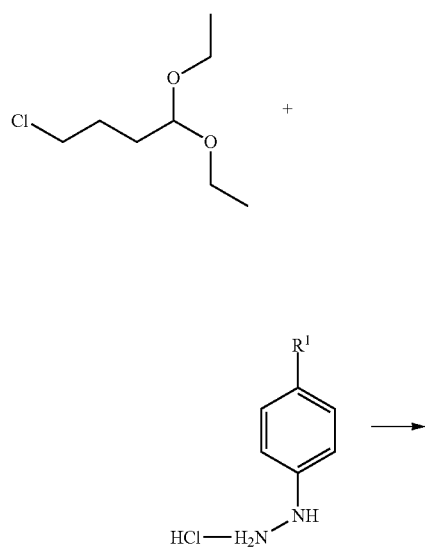

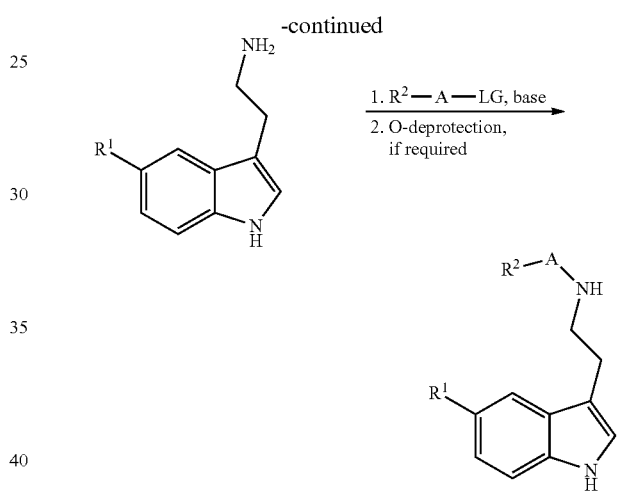

Synthesis Of Formula (II) Compounds

Compounds of Formula (II) can be prepared by the treatment of phenethylamino starting materials with electrophilic RLG reagents, as shown in Scheme 4.

Scheme 4

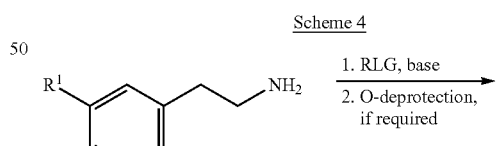

In Scheme 4, R can be any of the $R^2$ or $R^3$ groups described for Formula (II), and LG is a leaving group. If a tertiary amine is desired, the number of equivalents of RLG can be adjusted accordingly.

If the required phenethylamino starting material is not commercially available, the required compounds can be prepared from the corresponding phenylcarboxaldehyde via olefination to the corresponding nitroalkene and reduction to form the desired phenethylamino compound (Scheme 5).

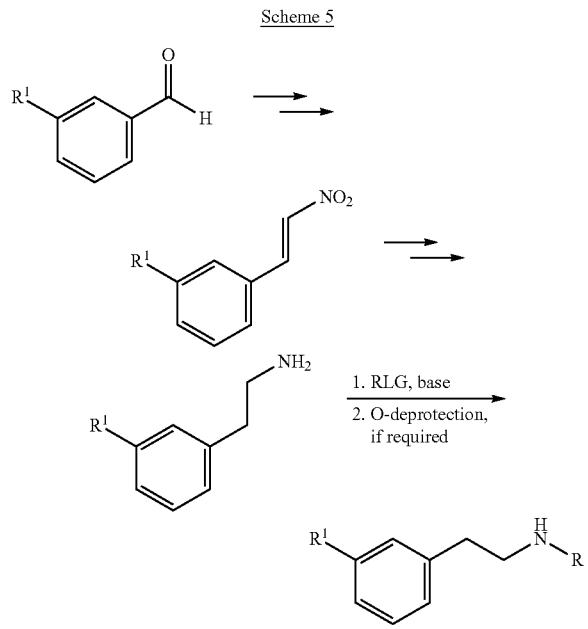

Scheme 5

Compounds of Formula (II) can also be prepared using carboxylic acid starting materials, as shown in Scheme 6.

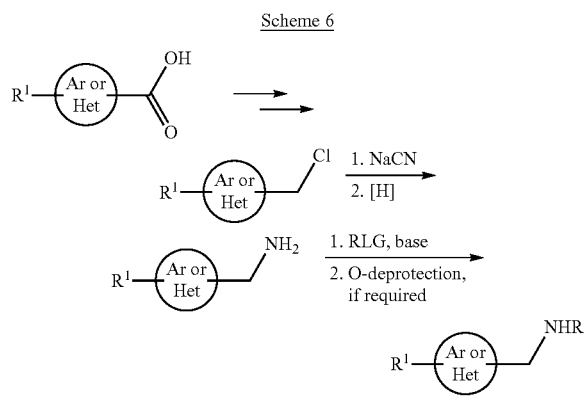

Scheme 6

In Scheme 6, Ar represents an aryl group, e.g., phenyl, and Het represents a heteroaryl group, e.g., pyridyl. In this scheme, the carboxylic acid group is transformed to a chloromethyl group. Treatment of this intermediate with cyanide followed by reduction affords the desired amine compound. If required, the amine compound can be treated with an electrophile RLG to afford still other compounds of Formula (II).

Pharmaceutical Compositions

The compounds of the invention (e.g., any of Compounds (1)-(39) or a compound according to Formula (I) or (II)), or tautomers, salts, solvates, or prodrugs thereof, are preferably formulated into pharmaceutical compositions for administration to human subjects in a biologically compatible form suitable for administration in vivo. Accordingly, in another aspect, the present invention provides a pharmaceutical composition that includes a compound of the invention, or a tautomer, salt, solvate, or prodrug thereof, in admixture with a suitable diluent, carrier, or excipient.

The compounds of the invention (e.g., any of Compounds (1)-(39) or a compound according to Formula (I) or (II)) may be used in the form of the free base, in the form of tautomers, salts, solvates, prodrugs, or pharmaceutical compositions. All forms are within the scope of the invention. In accordance with the methods of the invention, the described compounds, or tautomers, salts, solvates, prodrugs, or pharmaceutical compositions thereof, may be administered to a patient in a variety of forms depending on the selected route of administration, as will be understood by those skilled in the art. The compounds of the invention, or tautomers, salts, solvates, prodrugs, or pharmaceutical compositions thereof, may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention (e.g., any of Compounds (1)-(39) or a compound according to Formula (I) or (II)), or a tautomer, salt, solvate, or prodrug thereof, may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention, or a tautomer, salt, solvate, or prodrug thereof, may be incorporated with an excipient and used in the form of ingestible tablets, buccal tablets, troches, capsules, elixirs, suspensions, syrups, wafers, and the like.

A compound of the invention (e.g., any of Compounds (1)-(39) or a compound according to Formula (I) or (II)), or a tautomer, salt, solvate, or prodrug thereof, may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 32-NF 27), published in 2008.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Pharmaceutical compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated.

One of skill in the art can determine the appropriate dosage based on the above factors. The compounds of the invention may be administered initially in a suitable dosage that may be adjusted as required, depending on the clinical response. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

Kits

Any of the compounds or pharmaceutical compositions of the invention (e.g., any of Compounds (1)-(39) or a compound according to Formula (I) or (II)) can be used together with a set of instructions, i.e., to form a kit. The kit may include instructions for use of the compounds of the invention in a screening method or as a therapy as described herein. For example, the instructions may provide dosing and therapeutic regimes for use of the compounds of the invention to reduce pain, including any type of pain described herein.

Inhibitors of SPR

The compounds and compositions described herein can be used to inhibit SPR, which catalyzes the final step of the transformation of GTP to BH4. BH4 is an essential co-factor required for normal function of several enzyme and neurotransmitter systems: phenylalanine hydroxylase, tyrosine hydroxylase, tryptophan hydroxylase, and the 3 nitric oxide synthases (NOS) subtypes all rely on BH4 allosteric regulation (Thony et al., *Biochem. J.* 347:1-16, 2000). BH4 is synthesized from guanosine triphosphate (GTP) in three tightly regulated steps by GCH-1,6-pyruvoyltetrahydriobiopterin synthase (PTPS), and sepiapterin reductase (SPR) (FIG. 1). The final step in the BH4 synthetic pathway is the conversion of 6-pyruvoyl tetrahydropterin to BH4 by sepiapterin reductase (SPR).

Two of the enzymes involved in de novo BH4 synthesis, GCH-1 and SPR, are up-regulated in preclinical pain models, and reducing the activity of these enzymes leads to preclinical pain relief (Tegeder et al., *Nature Medicine* 12:1269-1277, 2006). Accordingly, agents that reduce de novo BH4 synthesis (e.g., via direct active site inhibition of SPR) can be used in the prevention or treatment of pain.

Initial studies demonstrated that SPR is weakly inhibited by catecholamines and indoleamines, suggesting a negative feedback mechanism by downstream biogenic amines (Katoh et al., *Biochem. Biophys. Res. Commun.* 105:75-81, 1982; Smith et al., *J. Biol. Chem.* 267:5509-5607, 1992). Additional structural information can be obtained by analysis of the SPR protein structure. The crystal structures of human, mouse, and *Chlorobium tepidum* SPR have been solved in complex with a range of active site ligands including N-acetyl serotonin, NADPH, NADPH+, oxaloacctate and sepiapterin. The first solved structure of mouse SPR reveals a homodimeric structure of 261 amino acids (Auerbach et al., *EMBO J.* 16:7219-7230, 1997). The liganded protein X-ray crystal structure complexes of SPR reveal an active site formed by a 15 Å-deep pocket surrounded by the hydrophobic residues Leu105, Leu159, Tyr165, Trp168, Tyr171, Met206 and Cys160. SPR is a homolog of other oxidoreductase drug targets such as the M.tb InhA, the target of anti-tuberculosis drug isoniazid. The inhibition of SPR can be a useful target for developing new methods for the treatment or prevention of pain.

Inhibitors of SPR can be identified according to the methods described herein or known in the art (e.g., Katoh et al., *Biochem. Biophys. Res. Commun.* 105:75-81, 1982; Smith et al., *J. Biol. Chem.* 267:5509-5607, 1992).

Although not necessary, if desired, candidate SPR inhibitors can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water. Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used, if desired, to confirm the efficacy of SPR inhibitors (Stein et al., *Pharmacol. Biochem. Behav.* (1988) 31: 445-451; Woolf et al., *Neurosci.* (1994) 62: 327-331). Additionally, various tests assess peripheral neuropathic pain using lesions of the peripheral nervous system. One such example is the "axotomy pain model" (Watson, *J. Physiol.* (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCl) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied peri-neurally), models of post-herpetic neuralgia using HSV infection, and compression models.

In all of the above tests, outcome measures may be assessed, for example, according to behavior, electrophysiology, neurochemistry, or imaging techniques to detect changes in neural activity. Furthermore, several pain tests that mimic central neuropathic pain involve lesions of the central nervous system including, for example, spinal cord injury (e.g., mechanical, compressive, ischemic, infective, or chemical). In these particular tests, outcome measures are the same as those used for peripheral neuropathic pain.

Therapy and Other Uses

The methods of this invention are useful, for example, for the diagnosis, treatment, reduction, or prevention of various forms of pain.

Pain can take a variety of forms depending on its origin. Pain may be described as being peripheral neuropathic if the initiating injury occurs as a result of a complete or partial transection of a nerve or trauma to a nerve plexus. Alternatively, pain is described as being central neuropathic following a lesion to the central nervous system, such as a spinal cord injury or a cerebrovascular accident. Inflammatory pain is a form of pain that is caused by tissue injury or inflammation (e.g., in postoperative pain or rheumatoid arthritis). Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness associated with hypersensitivity to normally innocuous tactile stimuli), and/or spontaneous burning or shooting lancinating pain. In inflammatory pain, symptoms are apparent, at least initially, at the site of injury or inflamed tissues and typically accompany arthritis-associated pain, musculo-skeletal pain, and postoperative pain. Nociceptive pain is the pain experienced in response to a noxious stimulus, such as a needle prick or during trauma or surgery. Functional pain refers to conditions in which there is no obvious peripheral pathology or lesion to the nervous system. This particular form of pain is generated by abnormal function of the nervous system and conditions characterized by such pain include fibromyalgia, tension-type headache, and irritable bowel syndrome. The different types of pain may coexist or pain may be transformed from inflammatory to neuropathic during the natural course of the disease, as in post-herpetic neuralgia.

The methods of this invention are useful for the diagnosis, treatment, reduction, or prevention of various forms of pain, namely inflammatory pain, nociceptive pain, functional pain, and neuropathic pain, whether acute or chronic. Exemplary conditions that may be associated with pain include, for example, soft tissue, joint, bone inflammation and/or damage (e.g., acute trauma, osteoarthritis, or rheumatoid arthritis), myofascial pain syndromes (fibromylagia), headaches (including cluster headache, migraine, and tension type headache), myocardial infarction, angina, ischemic cardiovascular disease, post-stroke pain, sickle cell anemia, peripheral vascular occlusive disease, cancer, inflammatory conditions of the skin or joints, diabetic neuropathy, and acute tissue damage from surgery or traumatic injury (e.g., burns, lacerations, or fractures). The present invention is also useful for the treatment, reduction, or prevention of musculo-skeletal pain (after trauma, infections, and exercise), neuropathic pain caused by spinal cord injury, tumors, compression, inflammation, dental pain, episiotomy pain, deep and visceral pain (e.g., heart pain, bladder pain, or pelvic organ pain), muscle pain, eye pain, orofacial pain (e.g., odontalgia, trigeminal neuralgia, glossopharyngeal neuralgia), abdominal pain, gynecological pain (e.g., dysmenorrhea and labor pain), pain associated with nerve and root damage due to trauma, compression, inflammation, toxic chemicals, metabolic disorders, hereditary conditions, infections, vasculitis and autoimmune diseases, central nervous system pain, such as pain due to spinal cord or brain stem damage, cerebrovascular accidents, tumors, infections, demyelinating diseases including multiple sclerosis, low back pain, sciatica, and post-operative pain. Conditions that are amenable to treatment according to the present invention are described in detail, for example, in U.S.S.N. 10/987,289 and 11/584,449, as well as U.S. Pat. No. 6,593,331, each of which are hereby incorporated by reference.

Combination Therapy

The compounds of the present invention (e.g., any of Compounds (1)-(39) or a compound according to Formula (I) or (II)), or a tautomer, salt, solvate, prodrug, or pharmaceutical composition thereof, may be administered either alone or in combination with one or more additional therapeutic agents, such as an analgesic agent used in the treatment of nociception, inflammatory, functional, or neuropathic pain. According to this invention, the second therapeutic agent may or may not produce a therapeutic effect when administered on its own, but results in such an effect (e.g., pain reduction) when administered with the composition of the invention.

Exemplary analgesic agents include, without limitation, nonsteroidal anti-inflammatory agents (NSAIDs) (e.g. rofexocib, celecoxib, valdecoxib, paracoxib, salicylic acid, acetominophen, diclofenac, piroxican indomethacin, ibuprofen, and naproxen), opioid analgesics (e.g., propoxyphene, meperidine, hydromorphone, hydrocodone, oxycodone, morphine, codeine, and tramodol), NMDA antagonist analgesics (e.g., 2-piperidino-1 alkanol derivatives, ketamine, dextormethorphan, eliprodil, or ifenprodil), anesthetic agents (e.g., nitrous oxide, halothane, fluothane), local anesthetics (lidocaine, etidocaine, ropivacaine, chloroprocaine, sarapin, and bupivacaine), benzodiazepines (diazepam, chlordiazepoxide, alprazolam, and lorazepam), capsaicin, tricyclic antidepressants (e.g., amitriptyline, perphanazine, protriptyline, tranylcypromine, imipramine, desimipramine, and clomipramine), skeletal muscle relaxant analgesics (flexeril, carisoprodol, robaxisal, norgesic, and dantrium), migraine therapeutic agents (e.g., elitriptan, sumatriptan, rizatriptan, zolmitriptan, and naratriptan), anticonvulsants (e.g., phenyloin, lamotrigine, pregabalin, carbamazepine, oxcarbazepine, topiramate, valproic acid, and gabapentin), baclofen, clonidine, mexilitene, diphenyl-hydramine, hydroxysine, caffeine, prednisone, methylprednisone, decadron, paroxetine, sertraline, fluoxetine, tramodol, ziconotide, and levodopa.

Further, if desired, the mammal being treated may be administered more than one agent that inhibits the production of BH4 (e.g., those described in U.S. Ser. No. 10/987,289, hereby incorporated by reference). Optionally, the composition of the invention may contain more than one such inhibitor. Alternatively, the mammal may further be administered with specific inhibitors of enzymes that function downstream of BH4, in addition to the composition of the invention.

The following non-limiting examples are illustrative of the present invention.

EXAMPLES

Synthesis of Formula (I) Compounds
Synthesis of Compounds (1)-(5)

Compounds (1)-(5) were prepared according to Scheme 7. In this scheme, R can be, for example, any group that is defined for $R^2$ in Formula (I).

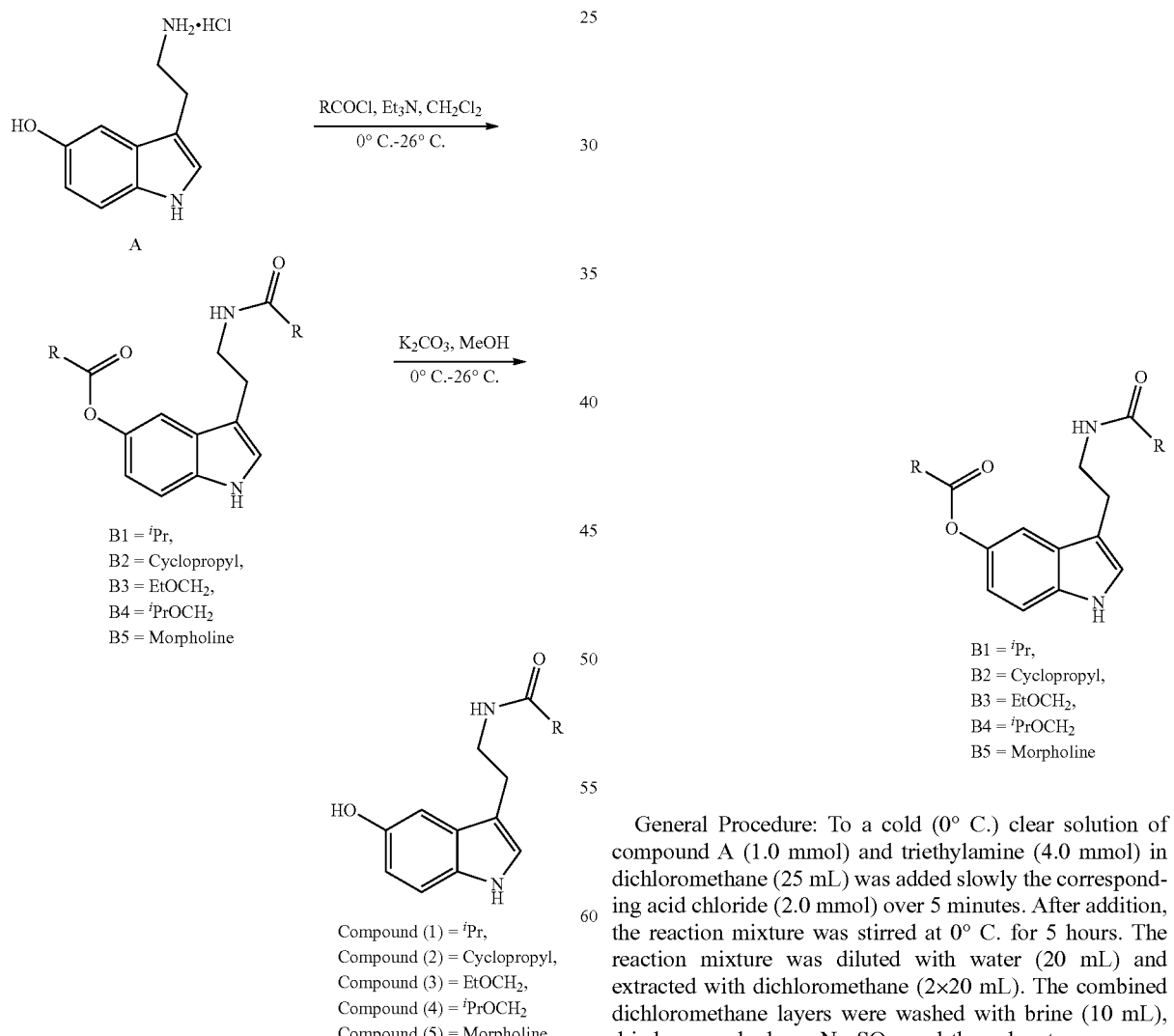

Preparation of Intermediates B1-B5

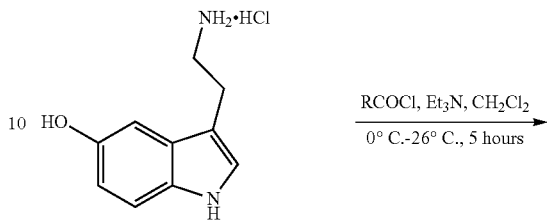

General Procedure: To a cold (0° C.) clear solution of compound A (1.0 mmol) and triethylamine (4.0 mmol) in dichloromethane (25 mL) was added slowly the corresponding acid chloride (2.0 mmol) over 5 minutes. After addition, the reaction mixture was stirred at 0° C. for 5 hours. The reaction mixture was diluted with water (20 mL) and extracted with dichloromethane (2×20 mL). The combined dichloromethane layers were washed with brine (10 mL), dried over anhydrous $Na_2SO_4$, and the solvent was evaporated to afford crude Intermediate B, which was then used in the next step (Table 2).

TABLE 2

| | | |
|---|---|---|
| B1 | 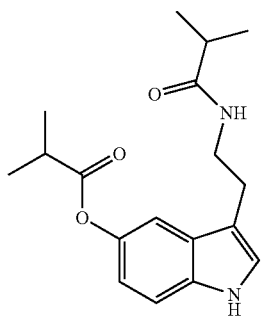 [SMILES: CC(C)C(=O)NCCc1c[nH]c2ccc(OC(=O)C(C)C)cc12] | Compound A (300 mg, 1.41 mmol) was reacted with 2-isopropoxy acetyl chloride (300 mg, 2.82 mmol) in the presence of triethylamine (1.32 mL, 9.40 mmol) and dichloromethane (7.5 mL). Compound B1 was obtained as a pale brown gum (230 mg, crude). Mass (M − H): 315.0. |
| B2 | 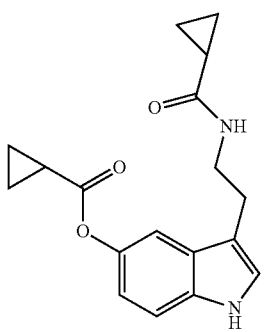 [SMILES: O=C(NCCc1c[nH]c2ccc(OC(=O)C3CC3)cc12)C1CC1] | Compound A (200 mg, 0.94 mmol) was reacted with cyclopropane carbonyl chloride (0.34 mL, 3.76 mmol) in the presence of triethylamine (mmol) and dichloromethane (5.0 mL). Compound B2 was obtained as a pale brown gum (200 mg, 61%). $^1$H NMR (CDCl$_3$): δ 8.10 (s, 1H), 7.34-7.30 (m, 2H), 7.06 (s, 1H), 6.94-6.91 (m, 1H), 5.67 (bs, 1H), 3.61-3.56 (q, 2H), 2.93 (s, J = 6.63 Hz; 2H), 1.91-1.84 (m, 1H), 1.30-1.16 (m, 4H), 1.05-0.95 (m, 4H), 0.72-0.67 (m, 2H). Mass (M + H): 313.0. |
| B3 | 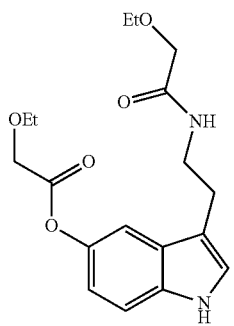 [SMILES: CCOCC(=O)NCCc1c[nH]c2ccc(OC(=O)COCC)cc12] | Compound A (300 mg, 1.41 mmol) was reacted with 2-ethoxy acetylchloride(206 mg, 1.69 mmol) in the presence of triethylamine (0.4 mL, 2.82 mmol) and dichloromethane (30.0 mL). Compound B3 was obtained as a pale brown gum (200 mg, crude). Mass (M + H): 349.0. |
| B4 | 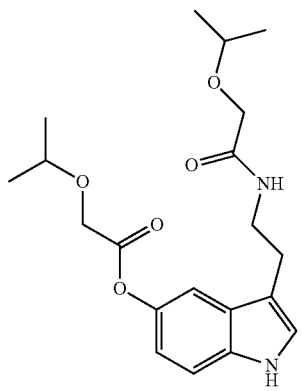 [SMILES: CC(C)OCC(=O)NCCc1c[nH]c2ccc(OC(=O)COC(C)C)cc12] | Compound A (300 mg, 1.41 mmol) was reacted with 2-isopropoxy acetyl chloride (289 mg, 2.02 mmol) in the presence of triethylamine (0.6 mL, 4.35 mmol) and dichloromethane (15.0 mL) to give compound B4 as a pale brown gum (230 mg, crude). Mass (M + H): 378.0. |

TABLE 2-continued

| | | |
|---|---|---|
| B5 | 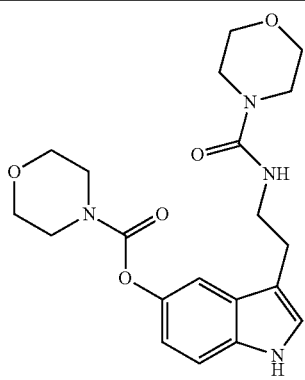 | Compound A (500mg, 2.35 mmol) was reacted with morpholine-4-carbonyl chloride (1.08 mL, 9.40 mmol) in the presence of triethylamine (1.32 mL, 9.40 mmol) and dichloromethane (15.0 mL). Compound B5 was obtained as a pale brown gum (230 mg, crude). |

Preparation of Compounds (1)-(5)

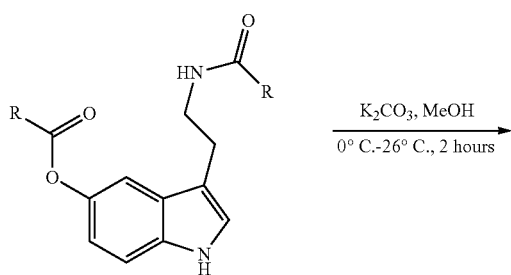

B1 = $^i$Pr,
B2 = Cyclopropyl,
B3 = EtOCH$_2$,
B4 = $^i$PrOCH$_2$
B5 = Morpholine $\xrightarrow[0°\text{C.-}26°\text{C., 2 hours}]{\text{K}_2\text{CO}_3, \text{MeOH}}$ -continued

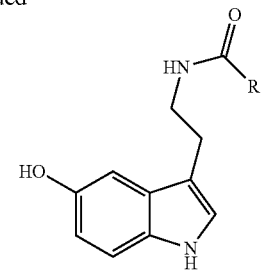

Compound (1) = $^i$Pr,
Compound (2) = Cyclopropyl,
Compound (3) = EtOCH$_2$,
Compound (4) = $^i$PrOCH$_2$
Compound (5) = Morpholine General Procedure: A suspension of Intermediate B (1.0 mmol) and K$_2$CO$_3$ (1 mmol) in methanol (20 mL) was stirred at 26° C. for 2 hours. The reaction mixture was concentrated under reduced pressure. The residue was diluted with water (30 mL) and extracted with ethyl acetate (2×20 mL). The combined ethyl acetate layers were washed with water (10 mL), brine (10 mL), dried over anhydrous Na$_2$SO$_4$, and the solvent was removed to afford the corresponding crude product (Table 3), which was purified by column chromatography (100-200 mesh silica gel) using 3% MeOH in chloroform as eluent.

TABLE 3

| (1) | 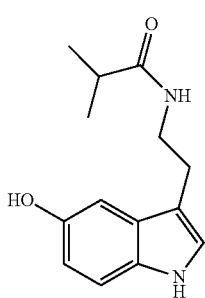 [SMILES: CC(C)C(=O)NCCc1c[nH]c2ccc(O)cc12] | Intermediate B1 (250 mg, 0.761 mmol) was reacted with K$_2$CO$_3$ (110 mg, 0.761 mmol) in MeOH (5.0 mL) to give Compound (1) (70 mg, 38.4%) as a pale brown gum. $^1$H NMR (DMSO-d$_6$: δ 10.47 (bs, 1H), 8.5 (s, 1H), 7.82 (bs, 1H), 7.11 (d, J = 8.70 Hz; 1H), 7.01 (s, 1H), 6.82 (s, 1H), 6.59-6.56 (m, 1H), 3.28-3.23 (m, 2H), 2.70 (t, J = 7.46 Hz; 2H), 2.35-2.31 (m, 1H), 1.00 (s, 3H), 0.98 (s, 3H). Mass (M + H): 247.0. IR (cm$^{-1}$): 3401, 2967, 2928, 1642, 1231, 935, 796. HPLC purity (%): 94.5 (Max plot), 87.98 (254 nm), 96.9 (215 nm). |

TABLE 3-continued

| | | |
|---|---|---|
| (2) | 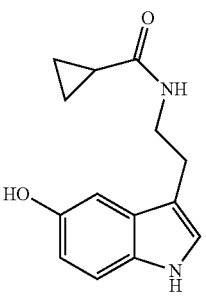 [SMILES: O=C(NCCc1c[nH]c2ccc(O)cc12)C1CC1] | Intermediate B2 (180 mg, 0.51 mmol) was reacted with $K_2CO_3$ (72 mg, 0.51 mmol) in MeOH (5.0 mL) to give Compound (2) (80 mg, 63%) Pale brown solid. $^1$H NMR (DMSO-$d_6$): δ 10.49 (bs, 1H), 8.59 (s, 1H), 8.16 (t, J = 5.12 Hz; 1H), 7.11 (d, J = 8.78 Hz; 1H), 7.02 (s, 1H), 6.81 (s, 1H), 6.59-6.56 (m, 1H), 3.32-3.27 (m, 2H), 2.71 (t, J = 7.31 Hz; 2H), 1.55-1.49 (m, 1H), 0.69-0.61 (m, 4H). Mass (M + H): 245.0. IR (cm$^{-1}$): 3420, 2925, 1648, 1456, 1242, 929. HPLC purity (%): 96.32 (Max plot), 96.29 (254 nm), 98.8 (215 nm). |
| (3) | 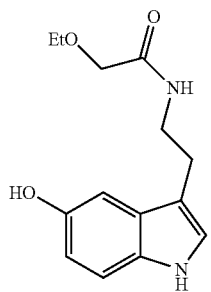 [SMILES: CCOCC(=O)NCCc1c[nH]c2ccc(O)cc12] | Intermediate B3 (250 mg, 0.718 mmol) was reacted with $K_2CO_3$ (99 mg, 0.718 mmol) in MeOH (5.0 mL) to give Compound (3) (100 mg, 52.9%) Pale brown solid. $^1$H NMR (DMSO-$d_6$): δ 10.49 (bs, 1H), 8.59 (s, 1H), 7.73 (t, J = 5.61 Hz; 1H), 7.11 (d, J = 8.29 Hz; 1H), 7.04 (s, 1H), 6.84 (s, 1H), 6.59-6.57 (m, 1H), 3.81 (s, 2H), 3.47-3.42 (m, 2H), 3.37-3.32 (m, 2H), 2.76 (t, J = 7.56 Hz; 2H), 1.12 (t, J = 6.83 Hz; 3H). Mass (M + H): 263.0. IR (cm$^{-1}$): 3368, 2921, 1644, 1459, 1374, 671. HPLC purity (%): 97.31 (Max plot), 91.76 (254 nm), 97.63 (215 nm). |
| (4) | 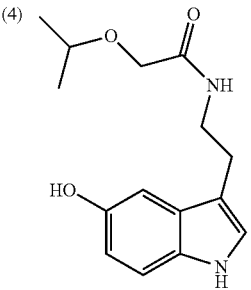 | Intermediate B4 (532 mg, 1.41 mmol) was reacted with $K_2CO_3$ (195 mg, 1.41 mmol) in MeOH (6.0 mL) to give Compound (4) (150 mg, 38.4%) as a pale brown gum. $^1$H NMR (CDCl$_3$): δ 7.91 (bs, 1H), 7.23-7.21 (m, 1H), 7.05-7.02 (m, 2H), 6.08-6.78 (m, 2H), 5.13 (s, 1H), 3.91 (s, 2H), 3.63-3.53 (m, 3H), 1.09 (s, 3H), 1.08 (s, 3H). Mass (M + H): 277.0. IR (cm$^{-1}$): 3398, 2972, 1655, 1459, 1213, 935. HPLC purity (%): 98.72 (Max plot), 98.73 (254 nm), 99.23 (215 nm). |
| (5) | 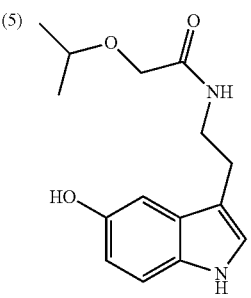 | Intermediate B5 (400 mg, 0.99 mmol) was reacted with $K_2CO_3$ (137 mg, 0.99 mmol) in MeOH (8.0 mL) to give Compound (5) (170 mg, 59%) Pale brown solid, $^1$H NMR (DMSO-$d_6$): δ 10.45 (bs, 1H), 8.56 (s, 1H), 7.10 (d, J = 8.70 Hz; 1H), 7.01 (s, 1H), 6.83 (s, 1H), 6.63-6.56 (m, 2H), 3.53 (t, J = 4.35 Hz; 4H), 3.26-3.25 (m, 6H), 2.73 (t, J = 7.46 Hz; 2H). Mass (M + H): 290.0. IR (cm$^{-1}$): 3409, 2921, 2853, 1629, 1534, 1263, 1112, 851. HPLC purity (%): 97.27 (Max plot), 98.47 (254 nm), 98.88 (215 nm). |

Synthesis of Compounds (6), (7), and (8)
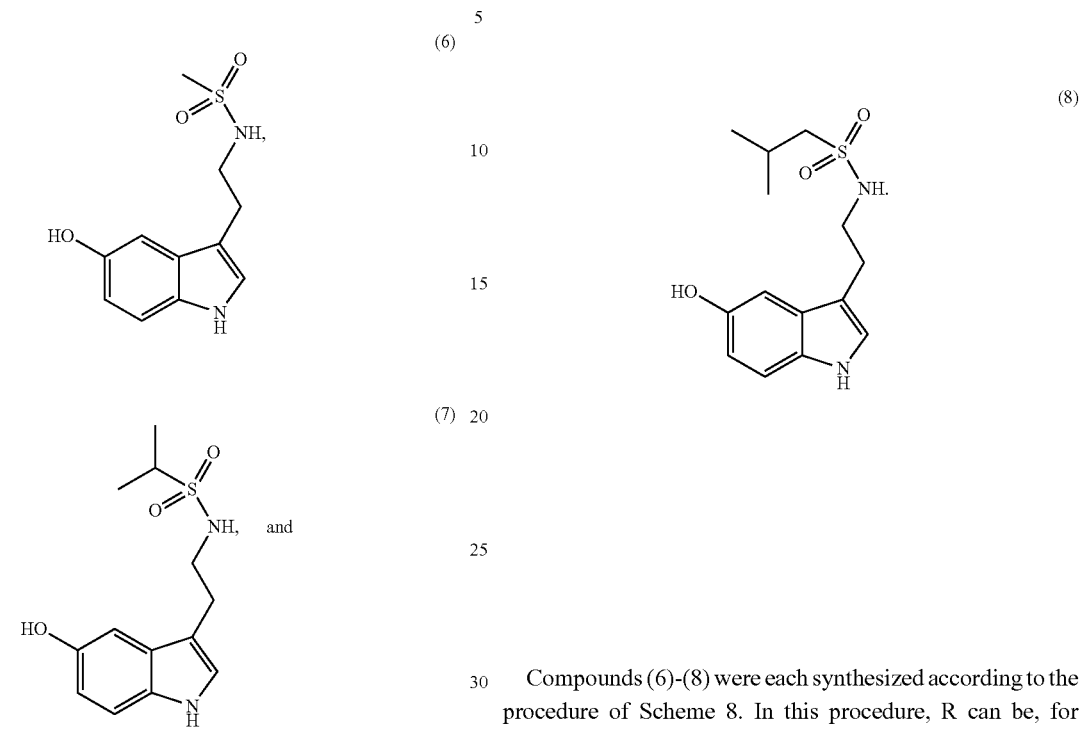
Compounds (6)-(8) were each synthesized according to the procedure of Scheme 8. In this procedure, R can be, for example, any group as defined for $R^2$ in Formula (I).
Scheme 8
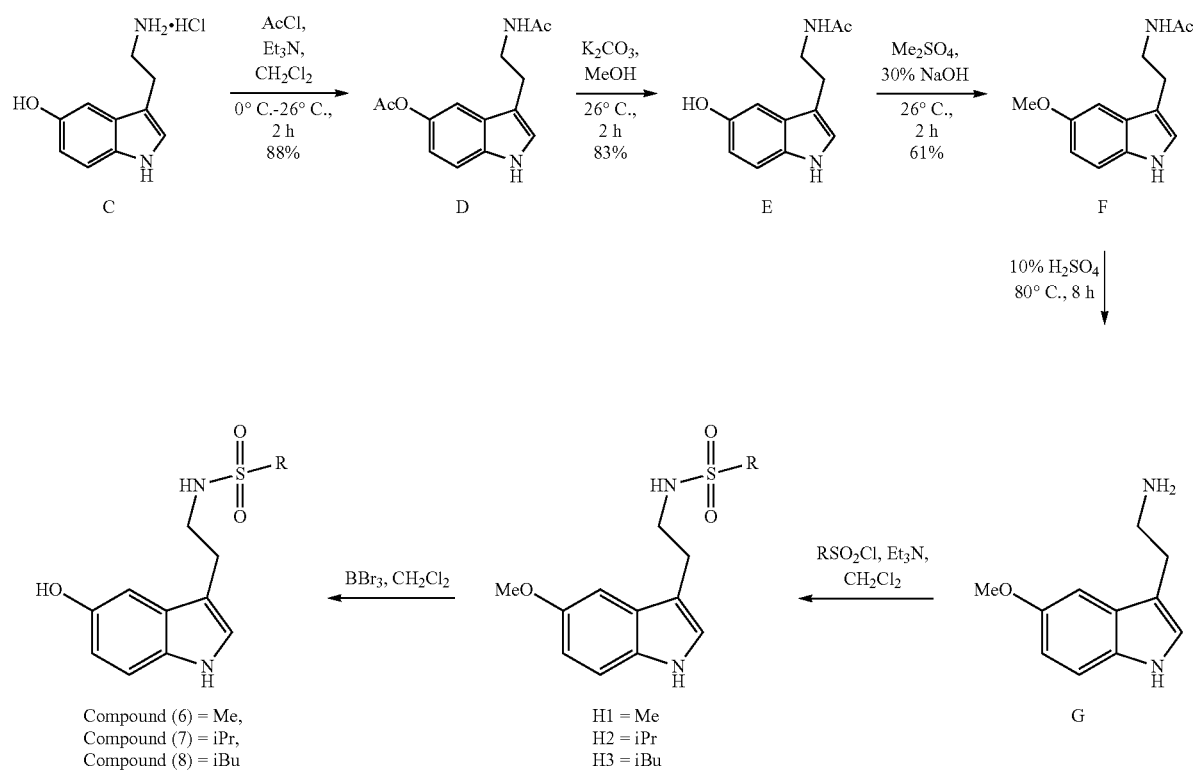

Preparation of Intermediate D

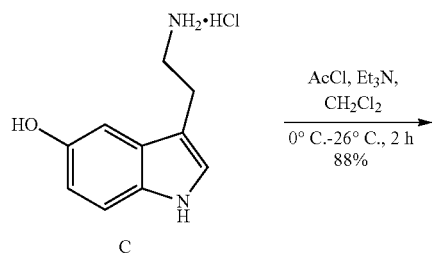

Preparation of Intermediate F

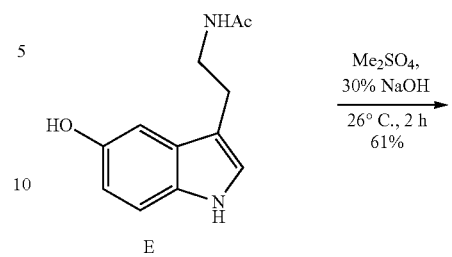

To a cold (0° C.), clear solution of Intermediate C (2.5 g, 11.75 mmol) and triethylamine (8.25 mL, 58.77 mmol) in dichloromethane (80.0 mL) was added slowly acetyl chloride (2.67 mL, 37.61 mmol) over 10 minutes. After the addition was complete, the reaction mixture was allowed to warm at room temperature and stirred for 2 hours. The reaction mixture was diluted with dichloromethane (20 mL) and washed with water (2×20 mL) and brine (30 mL), dried over anhydrous $Na_2SO_4$, and the solvent was removed to afford the crude Intermediate D (3.3 g, 88%) as a pale brown gum. Mass (M+H): 261.0.

Preparation of Intermediate E

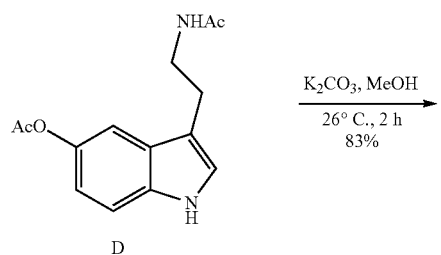

To a solution of Intermediate E (2.3 g, 10.55 mmol) in a 30% NaOH solution (1.3 mL) at 26° C., dimethyl sulfate (1.7 mL, 17.93 mmol) was added slowly for 15 minutes. After the addition was complete, the reaction mixture was stirred at ambient temperature for 2 hours. The reaction mixture was acidified with 2N HCl (pH ~2), diluted with water (20 mL), and extracted with ethyl acetate (2×50 mL). The combined ethyl acetate layers were washed with water (2×20 mL) and brine (20 mL), dried over anhydrous $Na_2SO_4$, and the solvent was removed to afford the crude Intermediate F, which was washed with ether (2×10 ml) and n-pentane (10 mL) and then dried to afford the Intermediate F (1.5 g, 61.4%), as off white solid. $^1$H NMR (CDCl$_3$): δ 8.02 (bs, 1H), 7.26 (s, 1H), 7.04-7.01 (m, 2H), 6.89-6.86 (m, 1H), 5.54 (bs, 1H), 3.86 (s, 3H), 3.60 (q, 2H), 2.94 (t, J=6.73 Hz; 2H), 1.93 (s, 3H). Mass (M+H): 233.0.

Preparation of Intermediate G

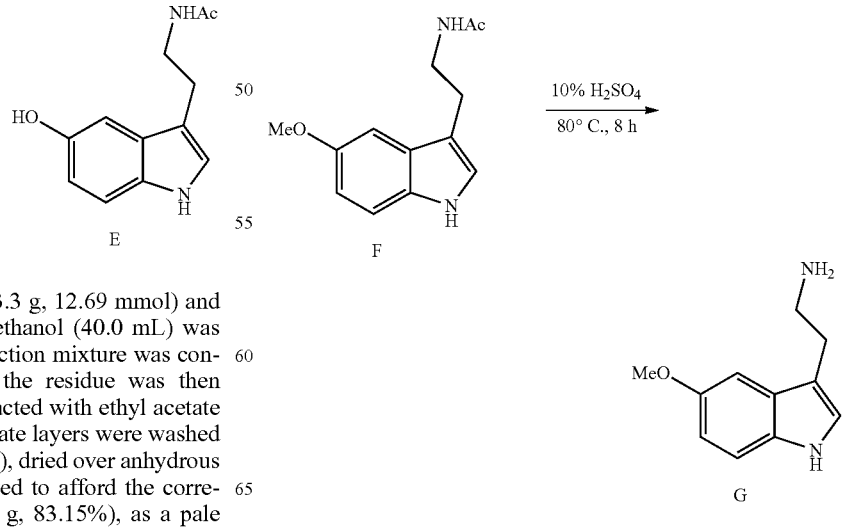

A suspension of Intermediate D (3.3 g, 12.69 mmol) and $K_2CO_3$ (1.75 g, 12.69 mmol) in methanol (40.0 mL) was stirred at 26° C. for 2 hours. The reaction mixture was concentrated under reduced pressure; the residue was then diluted with water (50 mL) and extracted with ethyl acetate (2×50 mL). The combined ethyl acetate layers were washed with water (20 mL) and brine (20 mL), dried over anhydrous $Na_2SO_4$, and the solvent was removed to afford the corresponding crude Intermediate E (2.3 g, 83.15%), as a pale brown gum. Mass (M+H): 219.0.

A solution of Intermediate F (1.4 g, 6.03 mmol) in a 10% NaOH solution (13.5 mL) was stirred at 80° C. for 8 hours. The reaction mixture was basified with 20% NaOH (pH ~10) and extracted with ethyl acetate (2×50 mL). The combined ethyl acetate layers were washed with water (30 mL) and brine (20 mL), dried over anhydrous $Na_2SO_4$, and the solvent was removed to afford the crude product, which was washed with pet ether (2×10 ml) and n-pentane (10 mL) then dried to afford Intermediate G (1.2 g, crude), as pale brown solid. $^1$H NMR (CDCl$_3$): δ 10.58 (bs, 1H), 7.20 (t, J=8.78 Hz; 1H), 7.07 (s, 1H), 6.98 (s, 1H), 6.71-6.68 (m, 1H), 3.75 (s, 3H), 2.81-2.69 (m, 4H), 1.39 (bs, 2H).

Preparation of Intermediates H1-H3

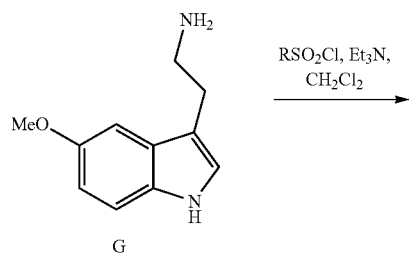

G

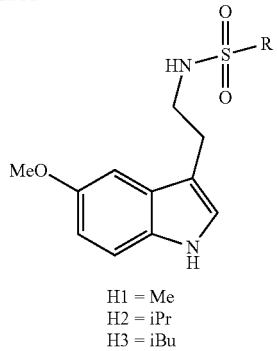

H1 = Me
H2 = iPr
H3 = iBu

General Procedure: To a cold (0° C.) solution of Intermediate G (1.0 mmol) and triethylamine (1.5 mmol) in dichloromethane (30 mL), the requisite sulfonyl chloride (1.2 mmol) was added slowly for 5 minutes. After the addition was complete, the reaction mixture was allowed to reach room temperature and stirred for 2 hours. The reaction mixture was diluted with dichloromethane (20 mL), washed with water (2×10 mL) and brine (20 mL), dried over anhydrous $Na_2SO_4$, and the solvent was removed to afford the crude Intermediate H (Table 4), which was purified by column chromatography (silica gel 100-200 mesh) using 40% ethyl acetate in petroleum ether as eluent.

TABLE 4

| | | |
|---|---|---|
| H1 | (structure) | Intermediate G (300 mg, 1.57 mmol) was reacted with methanesulfonyl chloride (271 mg, 2.36 mmol) and triethylamine (0.660 mL, 4.73 mmol) in dichloromethane (20 mL) to give Intermediate H1 (140 mg, crude), as white solid. $^1$H NMR (CDCl$_3$): δ 7.95 (bs, 1H), 7.29 (d, J = 8.78 Hz; 1H), 7.07 (s, 1H), 7.03 (s, 1H), 6.90-6.87 (m, 1H), 4.23 (m, 1H), 3.87 (s, 3H), 3.47 (q, 2H), 3.03 (t, J = 6.54 Hz; 2H), 2.85 (s, 3H). Mass (M + H): 269.1. |
| H2 | (structure) | Intermediate G (230 mg, 1.31 mmol) was reacted with isopropane sulfonyl chloride (225 mg, 1.57 mmol) and triethylamine (0.28 mL, 1.97 mmol) in dichloromethane (20 mL) to give Intermediate H2 (200 mg, crude), as a pale brown gum. $^1$H NMR (CDCl$_3$): δ 7.97 (bs, 1H), 7.27 (d, J = 8.78 Hz; 1H), 7.07 (s, 1H), 7.03 (s, 1H), 6.89-6.87 (m, 1H), 4.06 (m, 1H), 3.87 (s, 3H), 3.45 (q, 2H), 3.15-3.08 (m, 1H), 3.03 (t, J = 6.63 Hz; 2H), 1.30 (s, 3H), 1.29 (s, 3H). Mass (M + H): 297.0. |
| H3 | (structure) | Intermediate G (400 mg, 2.10 mmol) was reacted with ethylsulfonyl chloride (395 mg, 2.52 mmol) and triethylamine (0.88 mL, 6.31 mmol) in dichloromethane (20.0 mL) to give Intermediate H3 (400 mg, crude), as a pale brown gum. $^1$H NMR (CDCl$_3$): δ 7.97 (bs, 1H), 7.27 (d, J = 8.78 Hz; 1H), 7.06 (s, 1H), 7.03 (s, 1H), 6.89-6.87 (m, 1H), 4.18 (m, 1H), 3.87 (s, 3H), 3.43 (q, 2H), 3.03 (t, J = 6.42 Hz; 2H), 2.80 (d, J = 6.63 Hz; 2H), 2.18-2.11 (m, 1H), 1.02 (s, 3H), 1.01 (s, 3H). Mass (M + H): 311.0. |

Preparation of Compounds (6)-(8)

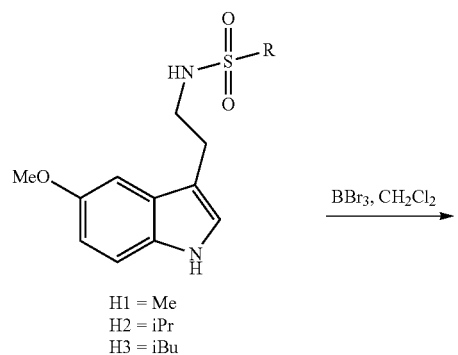

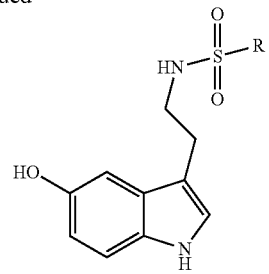

Compound (6) = Me,
Compound (7) = iPr,
Compound (8) = iBu

General Procedure: To a cold (−40° C.) solution of Intermediate H (1.0 mmol) in dichloromethane (20 mL) was added slowly BBr$_3$ (4.0 mmol). After the addition was complete, the reaction mixture was allowed to reach 0° C. and then stirred for 2 hours. The reaction mixture was diluted with dichloromethane (20 mL) and washed with water (2×10 mL). The combined dichloromethane layers were washed with water (10 mL) and brine (10 mL), dried over anhydrous Na$_2$SO$_4$, and the solvent was removed to afford the crude product, which was purified by column chromatography (silica gel 100-200 mesh) using 40% ethyl acetate in petroleum ether as eluent (Table 5).

TABLE 5

| | | |
|---|---|---|
| (6) | [structure] | Intermediate H1 (130 mg, 0.48 mmol) was reacted with BBr$_3$ (0.19 mL, 1.95 mmol) in dichloromethane (20.0 mL) to give Compound (6) (20 mg, 16%), as white solid. $^1$H NMR (DMSO-d$_6$): δ 10.53 (bs, 1H), 8.62 (s, 1H), 7.13-7.07 (m, 3H), 6.80 (s, 1H), 6.59-6.57 (m, 1H), 3.19-3.13 (m, 2H), 2.83-2.76 (m, 5H). Mass (M − H): 253.0. IR (cm$^{-1}$): 3443, 2923, 1635, 1318, 1160, 762. HPLC purity (%): 97.12 (Max plot), 97.84 (254 nm), 97.91 (215 nm). |
| (7) | [structure] | Intermediate H2 (200 mg, 0.67 mmol) was reacted with BBr$_3$ (0.26 mL, 2.71 mmol) in dichloromethane (20 mL) to give Compound (7) (45 mg, 23.5%), as white solid, $^1$H NMR (DMSO-d$_6$): δ 10.51 (bs, 1H), 8.60 (s, 1H), 7.12-7.06 (m, 3H), 6.79 (s, 1H), 6.59-6.56 (m, 1H), 3.19-3.10 (m, 3H), 2.79-2.75 (m, 2H), 1.20 (s, 3H), 1.18 (s, 3H). Mass (M + H): 283.0. IR (cm$^{-1}$): 3408, 2925, 1460, 1305, 1134, 792. HPLC purity (%): 95.48 (Max plot), 95.68 (215 nm). |
| (8) | [structure] | Intermediate H3 (400 mg, 1.29 mmol) was reacted with BBr$_3$ (0.5 mL, 5.16 mmol) in dichloromethane (30 mL) to give Compound (8) (85 mg, 22.3%) as brown solid. $^1$H NMR (DMSO-d$_6$): δ 10.52 (bs, 1H), 8.60 (s, 1H), 7.13-7.07 (m, 3H), 6.79 (s, 1H), 6.59-6.57 (m, 1H), 3.18-3.13 (m, 2H), 2.79-2.75 (m, 4H), 2.05-2.01 (m, 1H), 0.98 (s, 3H), 0.96 (s, 3H). Mass (M + H): 297.0. IR (cm$^{-1}$): 3424, 2924, 1305, 1138, 793. HPLC purity (%): 98.64 (Max plot), 96.97 (254 nm). 98.37 (215 nm). |

Synthesis of Compound (9)

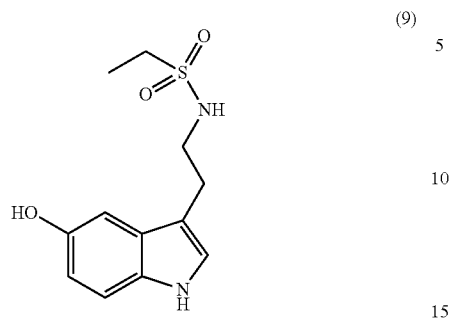

(9)

Compound (9) was prepared according to the procedure of Scheme 9.

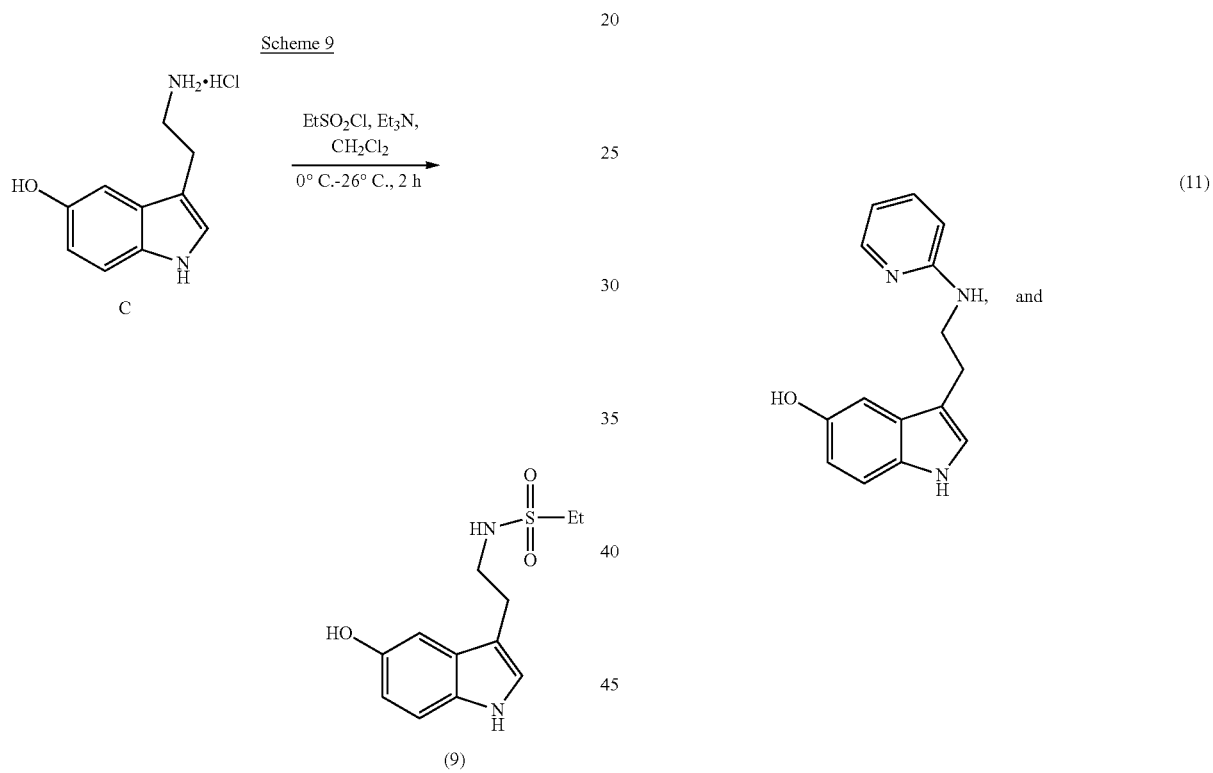

Scheme 9

(9)

To a cold (0° C.) solution of Intermediate C (500 mg, 2.35 mmol) and triethylamine (3.5 mL, 25.51 mmol) in dichloromethane (20.0 mL), was added slowly ethyl sulfonyl chloride (453 mg, 3.52 mmol) over 5 minutes. After the addition was complete, the reaction mixture was allowed to reach room temperature and stirred for 2 hours. The reaction mixture was diluted with dichloromethane (50 mL), washed with water (2×10 mL) and brine (20 mL), dried over anhydrous $Na_2SO_4$, and the solvent was removed to afford the crude product, which was purified by column chromatography (silica gel 100-200 mesh) using 30% ethyl acetate in petroleum ether as eluent. Compound (9) was obtained in 15 mg as a pale brown gum. $^1$H NMR (DMSO-$d_6$): δ 10.52 (bs, 1H), 8.61 (s, 1H), 7.16-7.07 (m, 3H), 6.79 (s, 1H), 6.59-6.57 (m, 1H), 3.17-3.12 (m, 3H), 2.97-2.91 (m, 2H), 2.79-2.75 (m, 2H), 1.15 (t, J=7.22 Hz; 3H). Mass (M+H): 268.9. IR (cm$^{-1}$): 3398, 2925, 1307, 1134, 790. HPLC purity (%): 93.74 (Max plot), 92.54 (215 nm).

Synthesis of Compounds (10)-(12)

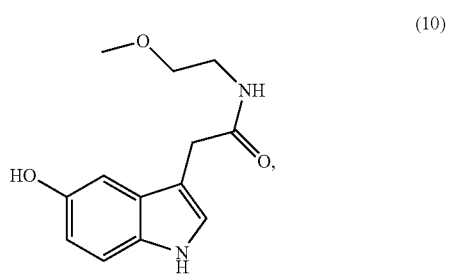

(10)

(11)

and

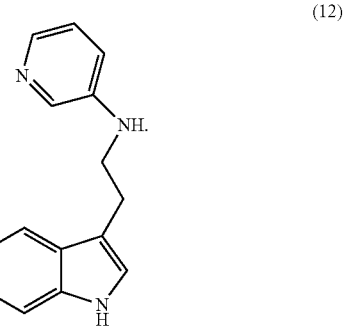

(12)

Compounds (10)-(12) were prepared according to the procedure shown in Scheme 10.

Scheme 10

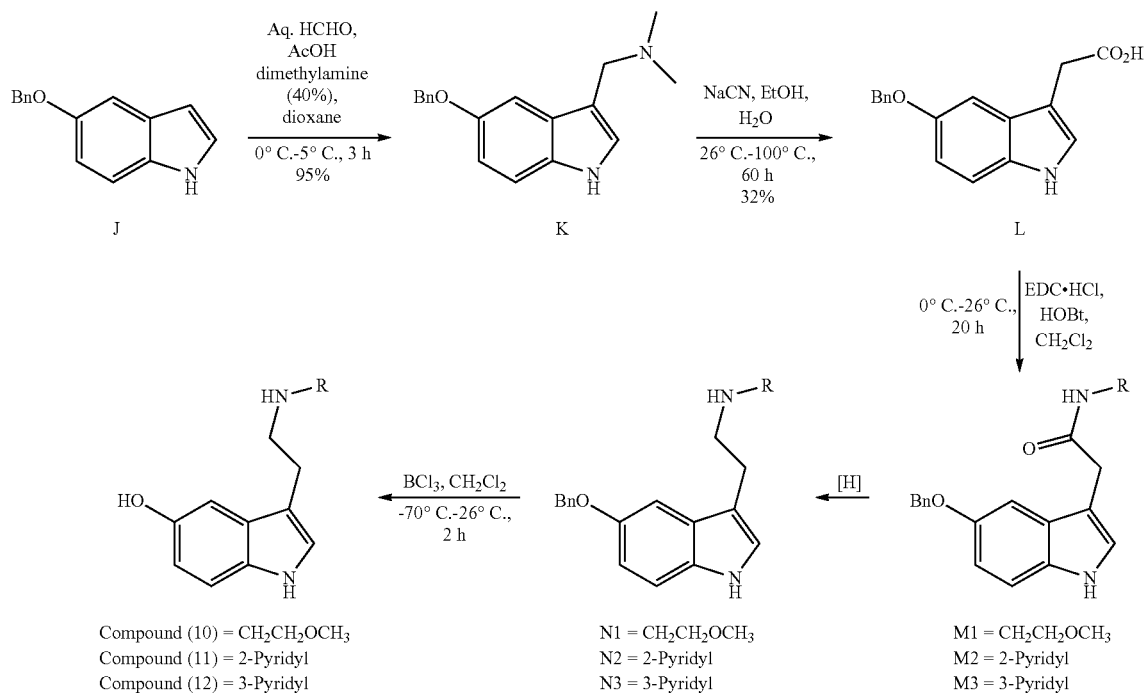

Compound (10) = CH$_2$CH$_2$OCH$_3$
Compound (11) = 2-Pyridyl
Compound (12) = 3-Pyridyl N1 = CH$_2$CH$_2$OCH$_3$
N2 = 2-Pyridyl
N3 = 3-Pyridyl M1 = CH$_2$CH$_2$OCH$_3$
M2 = 2-Pyridyl
M3 = 3-Pyridyl Preparation of Intermediate K

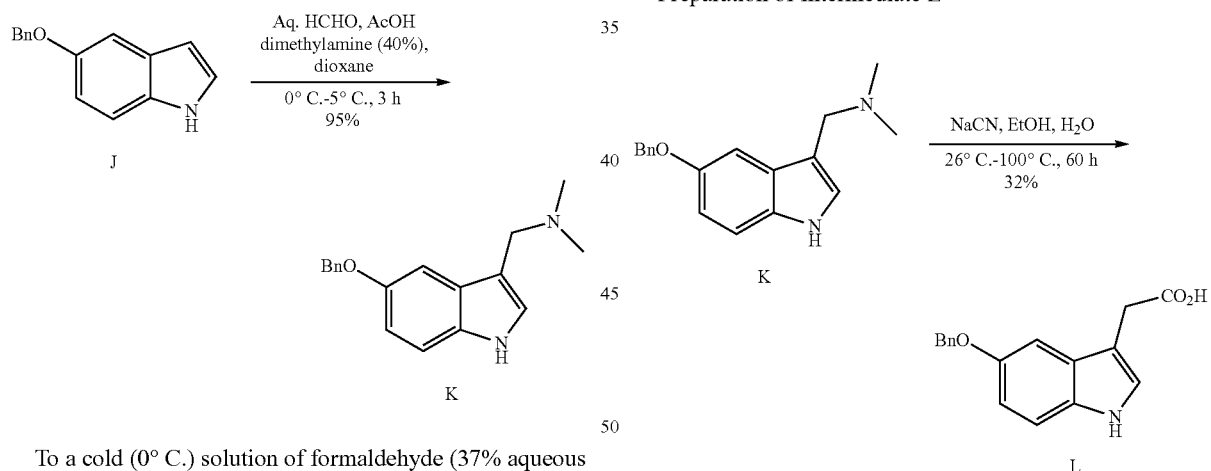

To a cold (0° C.) solution of formaldehyde (37% aqueous solution; 4.0 mL, 49.32 mmol) and acetic acid (46.0 g, 762.28 mmol) in dioxane (40.0 mL), was added dimethylamine (40% aqueous solution; 6.4 mL, 58.29 mmol) dropwise for 15 minutes. The reaction was then stirred for an additional 15 minutes. At the same temperature, a solution of Intermediate J (10.0 g, 44.84 mmol) in dioxane (70.0 mL) was added slowly. After the addition was complete, the reaction mixture was stirred at 0° C. for 2 hours. The reaction mixture was diluted with dioxane (100 mL) and then basified (pH~10) using an aqueous 10% KOH solution. The obtained solid was collected by filtration, washed with water (3×50 mL) and dried to afford crude Intermediate K (12.0 g, 95%) as an off white solid, which was used in the next step without further purifications. $^1$H NMR (DMSO-d$_6$): δ 10.72 (bs, 1H), 7.47 (d, J=7.42 Hz; 2H), 7.40-7.29 (m, 3H), 7.23 (d, J=8.78 Hz; 1H), 7.15 (m, 2H), 6.80-6.77 (m, 1H), 5.07 (s, 2H), 3.47 (s, 2H), 2.49 (s, 6H). Mass (M+H): 281.1.

Preparation of Intermediate L

To a solution of Intermediate K (14 g, 50.0 mmol) in water (40.0 mL) and ethanol (157.0 mL) at room temperature, sodium cyanide (20.0 g, 408.0 mmol) was added, and the reaction mixture was stirred at 100° C. for 60 hours. The reaction mixture was concentrated; the aqueous residue was then diluted with water (100 mL) and extracted with ethyl acetate (2×50 mL) to remove the impurities. The aqueous layer was acidified (pH~2) using diluted HCl and extracted with dichloromethane (3×50 mL). The combined organic layers were washed with water (30 mL) and brine (25 mL), dried over anhydrous Na$_2$SO$_4$, and the solvent was removed to afford the crude Intermediate L (4.5 g, 32%) as pale brown solid. $^1$H NMR (CDCl$_3$): δ 7.98 (bs, 1H), 7.48-7.46 (m, 2H), 7.39-7.28 (m, 4H), 7.18-7.13 (m, 2H), 6.96-6.94 (m, 1H), 5.10 (s, 2H), 3.78 (s, 2H). Mass (M+H): 282.1.

Preparation of Intermediates M1-M3

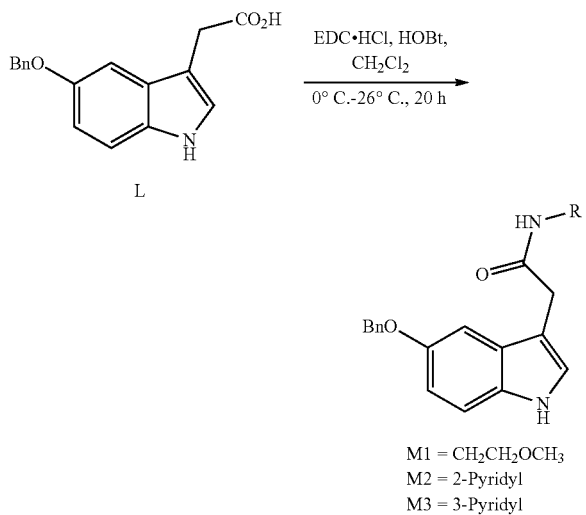

M1 = CH$_2$CH$_2$OCH$_3$
M2 = 2-Pyridyl
M3 = 3-Pyridyl

General Procedure: To a cold (0° C.) solution of Intermediate L (1.0 mmol), EDC.HCl (1.3 mmol), HOBt (1.3 mmol), and triethylamine (1.0 mmol) in dichloromethane (30 mL) was added slowly a solution of corresponding amine (1.1 mmol) in dichloromethane (2 mL) over 5 minutes. After the addition was complete, the reaction mixture was allowed to reach room temperature and stirred for 16 hours. The reaction mixture was diluted with dichloromethane (25 mL) and washed sequentially with water (10 mL), 10% NaHCO$_3$ solution (10 mL), water (10 mL), and brine solution (20 mL). The organic layer was then dried over anhydrous Na$_2$SO$_4$, and the solvent was removed to afford the crude Intermediate M (Table 6), which was purified by column chromatography (silica gel 100-200 mesh) using 1% MeOH in chloroform as eluent.

TABLE 6

| | Structure | Description |
|---|---|---|
| M1 | (structure shown) | Intermediate L (125 mg, 0.445 mmol) was reacted with methoxy ethylamine (37 mg, 0.49 mmol), EDC•HCl (111 mg, 0.577 mmol), HOBt (78 mg, 0.577 mmol), and Et$_3$N (0.063 mL, 0.45 mmol) to give Intermediate M1 (110 mg, 73%), off white solid. $^1$H NMR (CDCl$_3$): δ 8.09 (bs, 1H), 7.48-7.46 (m, 2H), 7.39-7.28 (m, 4H), 7.12-7.07 (m, 2H), 6.98-6.96 (m, 1H), 6.04 (b, 1H), 5.09 (s, 2H), 3.70 (s, 2H), 3.37-3.32 (m, 4H), 3.18 (s, 3H). Mass (M + H): 339.2. |
| M2 | (structure shown) | Intermediate L ((500 mg, 1.779 mmol) was reacted with 2-aminopyridine (185 mg, 1.96 mmol), EDC•HCl (442 mg, 2.31 mmol), HOBt (312 mg, 2.31 mmol), and Et$_3$N (0.25 mL, 1.78 mmol) to give Intermediate M2 (180 mg, 29%), off white solid. $^1$H NMR (CDCl$_3$): δ 8.26 (d, J = 8.59 Hz; 1H), 8.15 (m, 2H), 8.00 (bs, 1H), 7.70-7.66 (m, 1H), 7.45-7.43 (m, 2H), 7.36-7.25 (m, 4H), 7.22-7.20 (s, 1H), 7.11 (s, 1H), 7.00-6.96 (m, 2H), 5.07 (s, 2H), 3.88 (s, 2H). Mass (M + H): 358.2. |
| M3 | (structure shown) | Intermediate L ((500 mg, 1.779 mmol) was reacted with 3-aminopyridine (185 mg, 1.96 mmol), EDC•HCl (442 mg, 2.31 mmol), HOBt (312 mg, 2.31 mmol), and Et$_3$N (0.25 mL, 1.78 mmol) to give Intermediate M3 (180 mg, 35%), off white solid. $^1$H NMR (CDCl$_3$): δ 8.31-8.25 (m, 1H), 8.12-8.03 (m, 2H), 7.45-7.43 (m, 2H), 7.36-7.32 (m, 2H), 7.28-7.20 (m, 4H), 7.09 (m, 1H), 7.03-7.00 (m, 1H), 5.08 (s, 2H), 3.88 (s, 2H). Mass (M + H): 358.1. |

Preparation of Intermediates N2 and N3

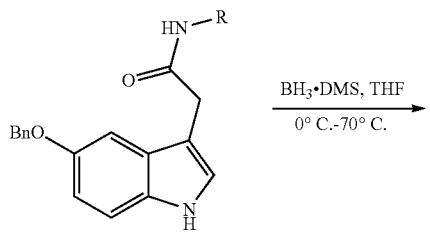

M2 = 2-Pyridyl
M3 = 3-Pyridyl

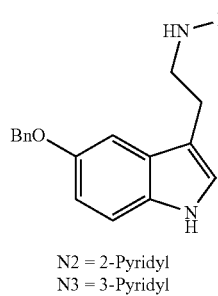

N2 = 2-Pyridyl
N3 = 3-Pyridyl

General Procedure: To a cooled solution of Intermediate M (1.0 mmol) in THF (30 mL) at 0° C., a solution of $BH_3DMS$ (15.0 mmol) was added at 0° C. After the addition was complete, the reaction mixture was stirred at 70° C. for 2 hours. The reaction mixture was cooled to 0° C., quenched with a mixture of methanol (2.0 mL) and 2N HCl (5.0 mL). After refluxing for 1 hour, the solvent was evaporated and the aqueous residue was basified (pH~10) using 2N NaOH solution. The aqueous layer was extracted with ethyl acetate (2×50 mL), washed with water (2×15 mL) and brine (15 mL), dried over dried over anhydrous $Na_2SO_4$, and evaporated to yield the crude product, which was purified by column chromatography (silica gel 100-200 mesh) using 80% ethyl acetate in pet ether as eluent to afford Intermediate N (Table 7).

TABLE 7

| | | |
|---|---|---|
| N2 | (structure) | Intermediate M2 (150 mg, 0.42 mmol) was reacted with BH₃•DMS (0.6 mL, 6.30 mmol) in THF (20.0 mL) to give Intermediate N2 (75 mg, 52%), off white solid. $^1$H NMR (CDCl$_3$): δ 8.25 (bs, 1H), 8.09-8.08 (m, 1H), 7.47-7.23 (m, 7H), 7.14 (s, 1H), 6.98-6.92 (m, 2H), 6.57-6.54 (m, 1H), 6.35 (d, J = 8.29 Hz; 1H), 5.07 (s, 2H), 4.61 (bs, 1H), 3.60-3.56 (q, 2H), 3.03 (t, J = 6.83 Hz, 2H). Mass (M + H): 344.2. |
| N3 | (structure) | Intermediate M3 (300 mg, 0.84 mmol) was reacted with BH₃•DMS (1.15 mL, 12.63 mmol) in THF (20.0 mL) to give Intermediate N3 (120 mg, 42%), off white solid. $^1$H NMR (CDCl$_3$): δ 8.04-7.94 (m, 3H), 7.47-7.25 (m, 6H), 7.09-7.03 (m, 3H), 6.96 (d, J = 8.78 Hz; 1H), 6.87-6.84 (m, 1H), 5.08 (s, 2H), 3.78 (bs, 1H), 3.44 (bs, 2H), 3.05 (t, J = 6.54 Hz, 2H). Mass (M + H): 344.2. |

Preparation of Compounds (11) and (12)

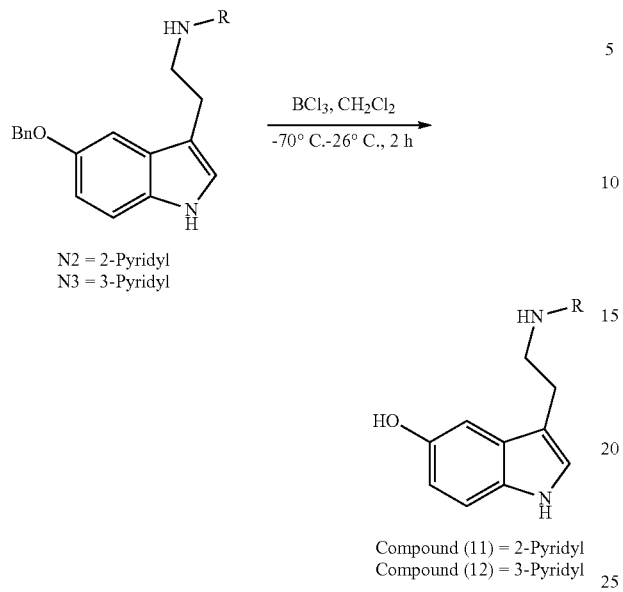

N2 = 2-Pyridyl
N3 = 3-Pyridyl

Compound (11) = 2-Pyridyl
Compound (12) = 3-Pyridyl

General Procedure: To a cold (−70° C.) solution of Intermediate O (1.0 mmol) in dichloromethane (30 mL), BCl$_3$ (0.1 M in DCM)(1.4 mmol) was added slowly. After the addition was complete, the reaction mixture was allowed to reach room temperature and stirred for 1 hour. The reaction mixture was diluted with dichloromethane (20 mL), washed with water (2×20 mL) and brine (10 mL), dried over anhydrous Na$_2$SO$_4$, and the solvent was removed to afford the crude product (Table 8), which was purified by PREP-TLC using 6% MeOH in chloroform as eluent.

Preparation of Compound (10)

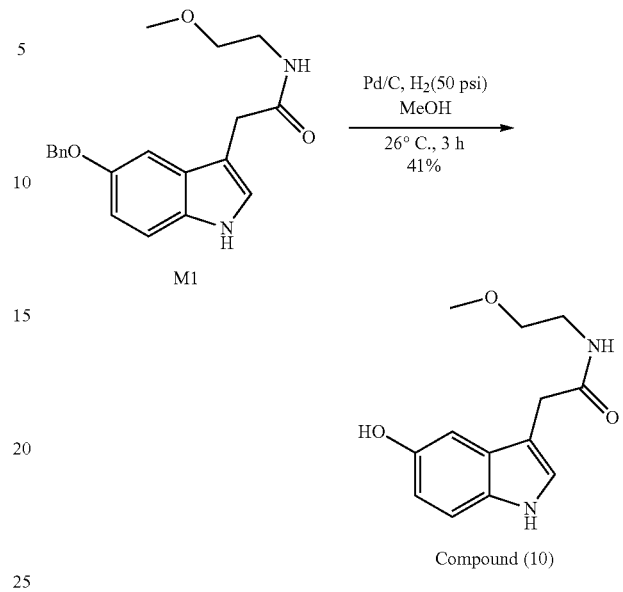

Compound (10)

A suspension of Intermediate M1 (100 mg, 0.29 mmol) and 10% Pd/C (30 mg, dry) in MeOH (10.0 mL) was hydrogenated (50 psi H$_2$ pressure) at room temperature for 5 hours. The reaction mixture was filtered, and the cake was washed with methanol (3×5 mL). The combined filtrates were concentrated under reduced pressure to give crude Compound (10), which was purified by PREP-TLC using 5% MeOH in chloroform as eluent to afford the product (30 mg, 41%) as an off white solid. NMR (DMSO-d$_6$): δ 10.54 (bs, 1H), 8.57 (s, 1H), 7.85 (s, 1H), 7.11 (d, J=8.78 Hz; 1H), 7.06 (s, 1H), 6.83

TABLE 8

| | | |
|---|---|---|
| (11) | ![structure] | Intermediate N2 (75 mg, 0.218 mmol) was reacted with BCl$_3$ (3.05 mL, 0.305 mmol) in dichloromethane (10 mL) to give Compound (11) (18 mg, 30%) as an off white solid. $^1$H NMR (DMSO-d$_6$): δ 10.48 (bs, 1H), 8.58 (s, 1H), 7.98 (m, 1H), 7.34 (m, 1H), 7.12 (d, J = 8.70 Hz; 1H), 7.06 (s, 1H), 6.86 (s, 1H), 6.60-6.43 (m, 4H), 3.49-3.44 (m, 2H), 2.85-2.81 (m, 2H). Mass (M + H): 254.1. IR (cm$^{-1}$): 3406, 2920, 2854, 1606, 1210, 1095, 771. HPLC purity (%): 96.37 (Max plot), 96.26 (254 nm), 96.18 (215 nm). |
| (12) | ![structure] | Intermediate N3 (120 mg, 0.348 mmol) was reacted with BCl$_3$ (5.0 mL, 0.5 mmol) in dichloromethane (15.0 mL) to give Compound (12) (25 mg, 28%) as an off while solid. $^1$H NMR (DMSO- d$_6$): δ 10.52 (bs, 1H), 8.60 (s, 1H), 7.98 (s, 1H), 7.75 (m, 1H), 7.13-7.05 (m, 3H), 6.91 (d, J = 8.29 Hz; 1H), 6.82 (s, 1H), 6.60-6.57 (m, 1H), 5.91 (s, 1H), 3.30-3.25 (m, 2H), 2.87-2.83 (m, 2H). Mass (M + H): 254.1. IR (cm$^{-1}$): 3398, 2919, 2851, 1586, 1467, 791. HPLC purity (%): 95.72 (Max plot), 94.43 (254 nm), 96.01 (215 nm). |

(s, 1H), 6.58 (dd, 1H), 3.40 (s, 2H), 3.34-3.30 (m, 2H), 3.22-3.17 (m, 5H). Mass (M+H): 249.1. IR (cm$^{-1}$): 3378, 3323, 2934, 1641, 1228, 1019, 669. HPLC purity (%): 99.73 (Max plot), 99.71 (215 nm).

Preparation of Compounds (13)-(15)

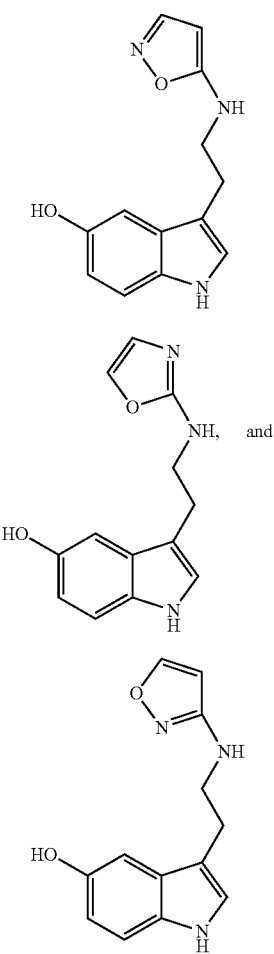

Compounds (13)-(15) can be synthesized according to the procedure shown in Scheme 10 by using one of the following amines in the preparation of Intermediate M (Table 9).

TABLE 9

| Compound | Amine reagent |
|---|---|
| (13) | |
| (14) | |
| (15) | |

Synthesis of Compound (16)

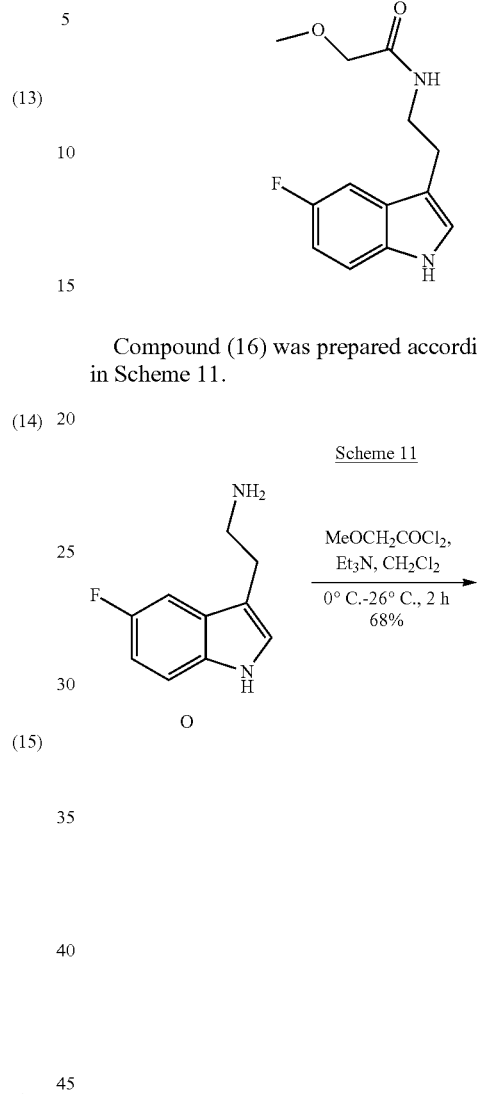

Compound (16) was prepared according to the procedure in Scheme 11.

To a cold (0° C.) solution of Intermediate 0 (250 mg, 1.16 mmol) and triethylamine (0.32 mL, 2.32 mmol) in dichloromethane (5.0 mL) was added slowly methoxyacetyl chloride (0.12 mL, 1.39 mmol) over 5 minutes. After the addition was complete, the reaction mixture was allowed to reach room temperature and stirred for 2 hours. The reaction mixture was diluted with dichloromethane (20 mL), washed with water (2×20 mL) and brine (20 mL), dried over anhydrous Na$_2$SO$_4$, and the solvent was removed to afford the crude product. The material was then washed with petroleum ether (2×4 mL), n-pentane (3 mL), and dried to afford Compound (16) (20 mg, 68.2%) as pale yellow solid. $^1$H NMR (CDCl$_3$): δ 8.15 (bs, 1H), 7.29-7.22 (m, 2H), 7.09 (s, 1H), 6.97-6.93 (m, 1H), 6.68 (bs, 1H), 3.87 (s, 2H), 3.64-3.59 (m, 2H), 3.33 (s, 3H), 2.95 (t, J=6.84, Hz; 2H). Mass (M+H): 251.0. HPLC purity (%): 98.87 (Max plot), 98.00 (254 nm), 98.88 (215 nm).

Synthesis of Compound (17)

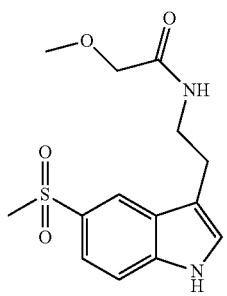

Compound (17) was prepared according the procedure described in Scheme 12.

Scheme 12

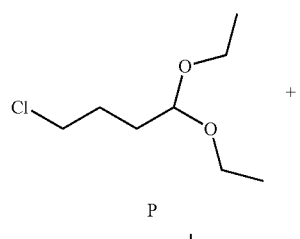

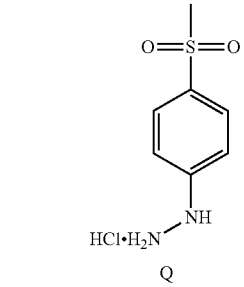

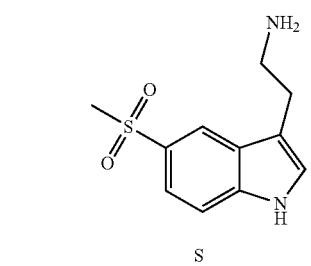

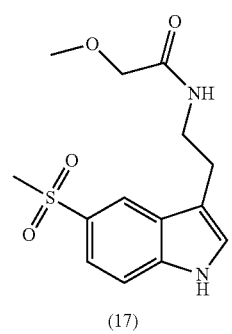

Preparation of Intermediate S

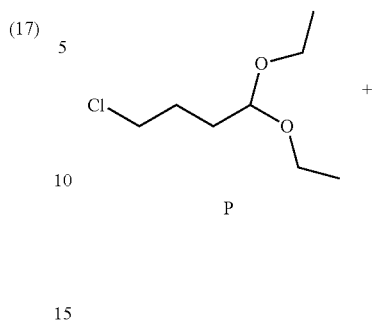

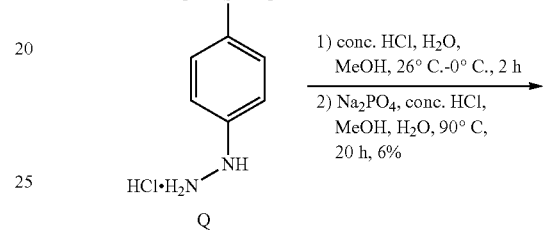

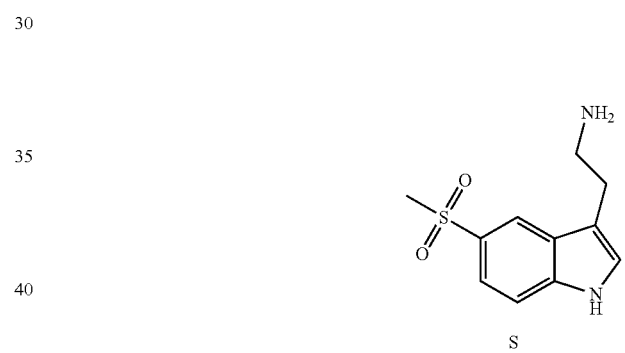

A solution of Intermediate P (1.0 g, 5.53 mmol) in concentrated HCl (0.2 mL) and water (11.6 mL) was stirred at room temperature for 1 hour. A solution of Intermediate Q (1.1 g, 4.97 mmol) in water (2.4 mL) and MeOH (12.8 mL) was added to the above mixture, which was then stirred at room temperature for 1 hour. The reaction mixture was cooled to 0° C. and the solid was filtered off, washed with 9:1 aqueous methanol (5.0 mL) and water (10.0 mL), and dried. To the solution of this compound in water (7.2 mL) and MeOH (29.0 mL) was then added $Na_2HPO_4$ (0.5 g, 3.54 mmol) and concentrated HCl (0.1 mL). The reaction mixture was then stirred at reflux for 20 hours. The reaction mixture was concentrated; the aqueous residue was then diluted with water (20 mL), saturated with $Na_2CO_3$, and extracted with dichloromethane (3×25 mL). The combined dichloromethane layers were dried over anhydrous $Na_2SO_4$, and the solvent was removed to afford the crude Intermediate S, which was purified by column chromatography (silica gel 100-200 mesh) using 2% (MeOH/$NH_3$) in chloroform as eluent to afford the product (80 mg, 6%) as brown solid. $^1$H NMR (DMSO-$d_6$): δ 11.41 (bs, 1H), 8.12 (s, 1H), 7.59-7.53 (m, 2H), 7.38 (s, 1H), 3.15 (s, 3H), 2.83 (s, 4H). Mass (M+H): 239.0.

Preparation of Compound (17)

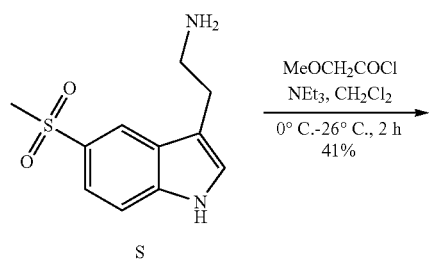

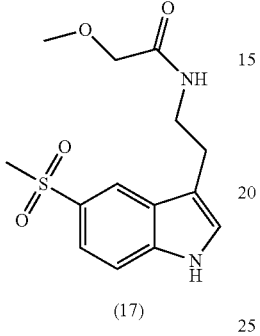

To a cold (0° C.) solution of Intermediate S (150 mg, 0.63 mmol) and triethylamine (0.13 mL, 0.94 mmol) in dichloromethane (10.0 mL) was added slowly a solution of methoxyacetyl chloride (0.06 mL, 0.69 mmol) in dichloromethane (2.0 mL) over 5 minutes. After the addition was complete, the reaction mixture was allowed to reach room temperature and stirred for 2 hours. The reaction mixture was diluted with dichloromethane (20 mL), washed with water (2×20 mL) and brine (10 mL), dried over anhydrous $Na_2SO_4$, and the solvent was removed to afford the crude product. This material was then purified by column chromatography (silica gel 100-200 mesh) using 2% MeOH in chloroform as eluent to afford Compound (17) (80 mg, 41%) as off white solid. $^1$H NMR ($CDCl_3$): δ 8.40 (bs, 1H), 8.25 (s, 1H), 7.75 (d, J=8.39 Hz; 1H), 7.50 (d, J=8.78 Hz; 1H), 7.24 (s, 1H), 6.66 (bs, 1H), 3.89 (s, 2H), 3.68-3.63 (m, 2H), 3.36 (s, 3H), 3.09 (s, 3H), 3.06-3.03 (t, J=7.03 Hz; 2H). Mass (M−H): 309.0. IR ($cm^{-1}$): 3344, 2925, 1656, 1289, 1147, 750. HPLC purity (%): 98.90 (Max plot), 94.95 (254 nm), 97.96 (215 nm).

Synthesis of Compound (18)

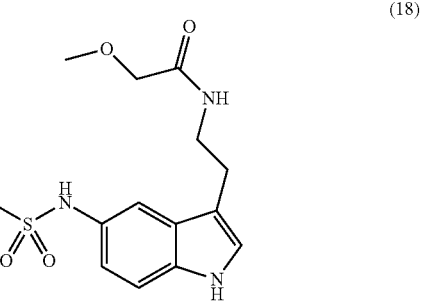

Compound (18) was synthesized according to the procedure shown in Scheme 13.

Scheme 13

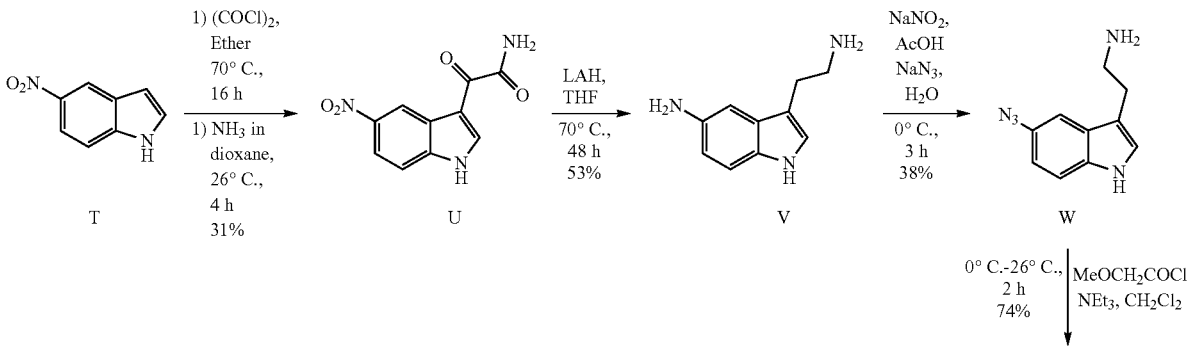

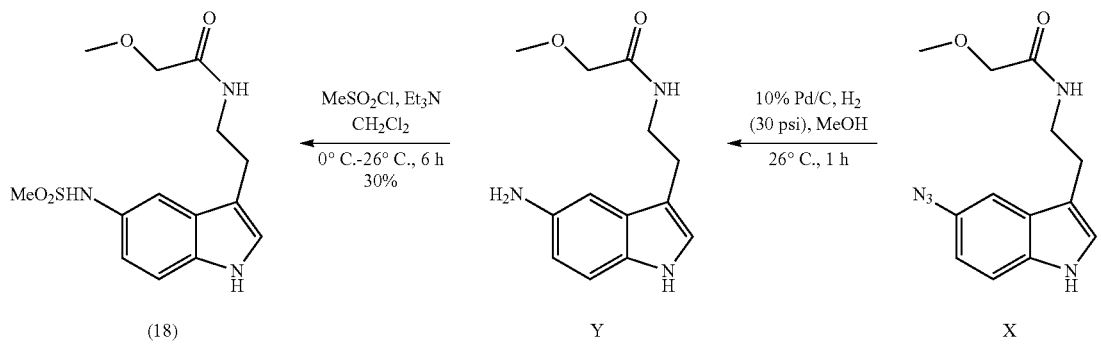

Preparation of Intermediate T

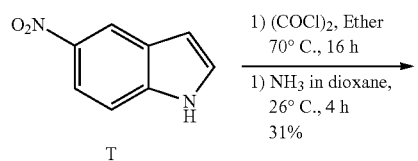

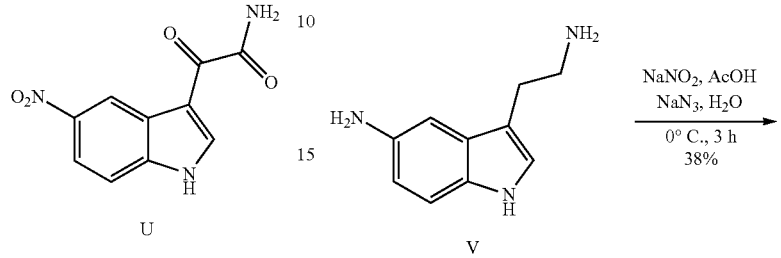

To a solution of Intermediate T (2.5 g, 15.41 mmol) in ether (50.0 mL) was added a solution of oxalyl chloride (5.4 mL, 61.67 mmol) in ether (15.0 mL) at room temperature. The resulting reaction was stirred at 40° C. for 16 hours. The reaction mixture was filtered, and the resulting solid was washed with ether (2×20 mL). The solid was then added to a saturated solution of $NH_3$ in dioxane (100.0 mL) and stirred for 4 hours. The reaction mixture was basified with $Na_2CO_3$, and concentrated to yield the crude product, which was purified by column chromatography (silica gel 100-200 mesh) using 70% ethyl acetate in petroleum ether as eluent to afford Intermediate U (1.2 g, 31%) pale yellow solid. $^1$H NMR (DMSO-$d_6$): δ 12.75 (bs, 1H), 9.08 (s, 1H), 8.93 (s, 1H), 8.19-8.15 (m, 2H), 7.86 (s, 1H), 7.74 (d, J=8.78 Hz; 1H). Mass (M−H): 232.0.

Preparation of Intermediate V

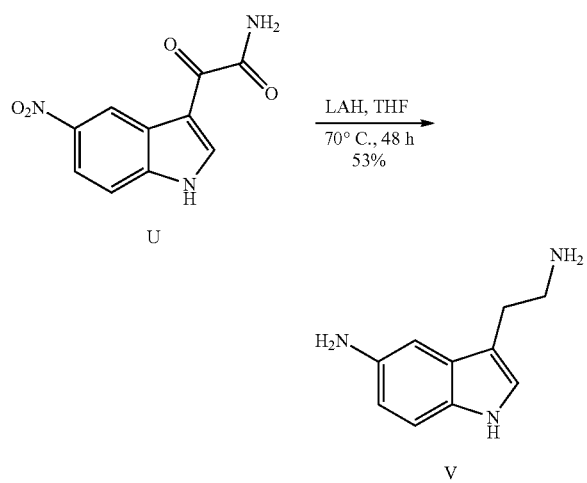

To a suspension of lithium aluminum hydride (3.26 g, 85.0 mmol) in THF (150.0 mL) at room temperature was added a solution of Intermediate U (1.0 g, 4.29 mmol) was added. The resulting mixture was stirred at 70° C. for 48 hours. The reaction mixture was then cooled to 0° C., quenched with ice cold water (5.0 mL), and filtered. The cake was washed with ethyl acetate (3×100 mL), and the combined filtrates were extracted. The separated organic layer was washed with water (25 mL) and brine (15 mL), dried over dried over anhydrous $Na_2SO_4$, and evaporated to yield crude Intermediate V, which was purified by column chromatography (silica gel 100-200 mesh) using (5:94:1 to 20:79:1) MeOH: chloroform: aq $NH_3$ as the eluent to afford the product (400 mg, 53.2%) as a brown gum. $^1$H NMR (DMSO-$d_6$): δ 10.30 (s, 1H), 7.22-7.00 (m, 2H), 6.93 (s, 1H), 6.47-6.44 (dd, 1H), 4.39 (bs, 2H), 2.81 (t, J=7.07 Hz; 2H), 2.66 (t, J=7.31 Hz; 2H). Mass (M+H): 176.1.

Preparation of Intermediate W

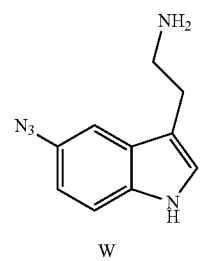

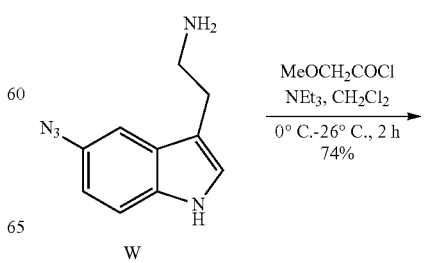

To a cold (0° C.) solution of Intermediate V (500 mg, 2.86 mmol) in acetic acid (15.0 mL) was added slowly a solution of $NaNO_2$ (217 mg, 3.14 mmol) in cold water (1.6 mL) over 5 minutes. After stirring for 5 minutes, a solution of $NaN_3$ (204 mg, 3.14 mmol) in cold water (1.6 mL) was added slowly. After the addition was complete, the reaction mixture was stirred at 0° C. for 2 hours. The reaction mixture was concentrated under reduced pressure, and the crude product was purified by column chromatography (silica gel 100-200 mesh) using (5:94:1 to 20:79:1) MeOH:chloroform:(aqueous $NH_3$) as the eluent to afford Intermediate W (220 mg, 38%) as a brown solid. $^1$H NMR (DMSO-$d_6$): δ 10.97 (bs, 1H), 7.42-7.32 (m, 1H), 7.21 (m, 2H), 6.82-6.80 (m, 1H), 2.79-2.74 (m, 4H). Mass (M+H): 202.1. IR (cm$^{-1}$): 3433, 2918, 2106, 920, 792.

Preparation of Intermediate X

-continued

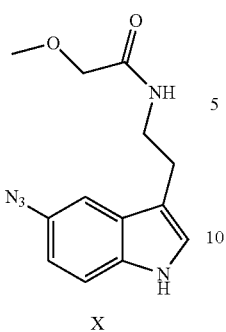

X

To a cold (0° C.) solution of Intermediate W (200 mg, 0.995 mmol) and triethylamine (20.14 mL, 0.995 mmol) in dichloromethane (20 mL) was added slowly a solution of methoxyacetyl chloride (100 mg, 0.895 mmol) in dichloromethane (5.0 mL) over 30 minutes. After the addition was complete, the reaction mixture was allowed to reach room temperature and stirred for 1 hour. The reaction mixture was diluted with dichloromethane (30 mL), washed with water (2×15 mL) and brine (20 mL), dried over anhydrous $Na_2SO_4$, and the solvent was removed to afford the crude product, which was purified by column chromatography (silica gel 100-200 mesh) using 20% MeOH in chloroform as the eluent to afford Intermediate X (200 mg, 74%) as an off white solid. $^1$H NMR (CDCl$_3$): δ 8.08 (bs, 1H), 7.34 (d, J=8.59 Hz; 1H), 7.24 (s, 1H), 7.09 (s, 1H), 6.90 (dd, 1H), 6.64 (b, 1H), 3.88 (s, 2H), 3.65-3.60 (q, 2H), 3.35 (s, 3H), 2.96 (t, J=6.93 Hz; 2H). Mass (M+H): 274.1.

Preparation of Intermediate Y

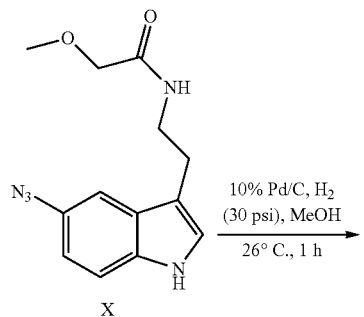

A suspension of Intermediate X (200 mg, 0.73 mmol) and 10% Pd/C (30 mg, dry) in MeOH (20.0 mL) was hydrogenated (30 psi $H_2$ pressure) at room temperature for 1 hour. The reaction mixture was filtered through Celite, and the cake was washed with methanol (3×5 mL). The combined filtrates were concentrated under reduced pressure to give crude Intermediate Y (180 mg, crude) brown gum. $^1$H NMR (DMSO-d$_6$): δ 10.31 (bs, 1H), 7.80 (t, J=5.39 Hz; 1H), 7.01 (d, J=8.29 Hz; 1H), 6.95 (s, 1H), 6.66 (s, 1H), 6.46 (dd, 1H), 4.42 (m, 2H), 3.78 (s, 2H), 3.41-3.28 (m, 5H), 2.72 (t, J=7.46 Hz; 2H). Mass (M+H): 248.1.

Preparation of Compound (18)

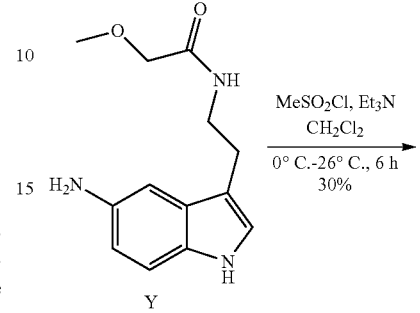

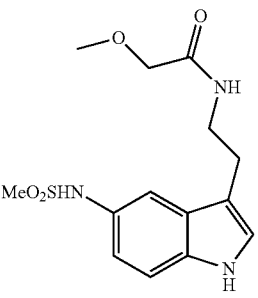

(18)

To a cold (0° C.) solution of Intermediate Y (90 mg, 0.364 mmol) and triethylamine (0.06 mL, 0.40 mmol) in dichloromethane (10.0 mL) was added slowly a solution of methanesulfonyl chloride (0.03 mL, 0.327 mmol) in dichloromethane (2.0 mL) over 15 minutes. After the addition was complete, the reaction mixture was allowed to reach room temperature and stirred for 6 hours. The reaction mixture was diluted with dichloromethane (30 mL), washed with water (2×10 mL) and brine (10 mL), dried over anhydrous $Na_2SO_4$, and the solvent was removed to afford the crude product, which was purified by PREP-TLC using 5% MeOH in chloroform as the eluent to afford Compound (18) (35 mg, 30%) as a pale brown gum. $^1$H NMR (CDCl$_3$): δ 8.12 (bs, 1H), 7.52 (s, 1H), 7.35 (d, J=8.35 Hz; 1H), 7.14-7.11 (m, 2H), 6.66 (bs, 1H), 6.33 (bs, 1H), 3.88 (s, 2H), 3.63-3.60 (q, 2H), 3.36 (s, 3H), 3.00-2.96 (m, 5H). Mass (M+H): 326.1. IR (cm$^{-1}$): 3387, 3275, 2930, 1658, 1321, 1148, 975. HPLC purity (%): 97.97 (Max plot), 97.20 (215 nm).

Synthesis of Compounds (19) and (20)

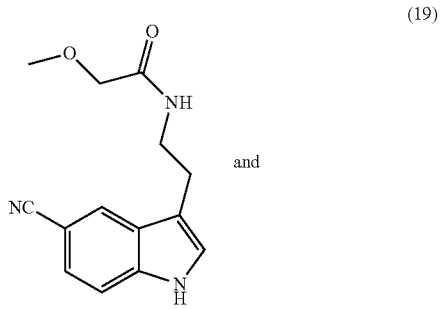

(19)

and

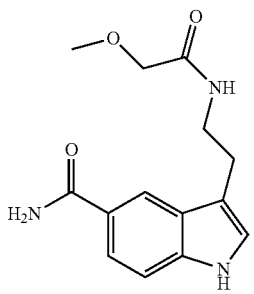

(20)

Compounds (19) and (20) were synthesized according to Scheme 14.

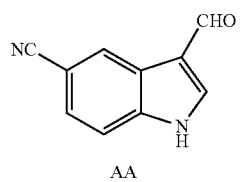

AA

POCl₃ (3.6 mL, 38.68 mmol) was added to DMF (16.5 mL) dropwise at 0° C.-10° C. The resulting mixture was stirred for 30 minutes, cooled to 0° C., and a solution of Intermediate Z (5.0 g, 35.17 mmol) in DMF (10.0 mL) was added over 15 minutes. After the addition was complete, the reaction mix-

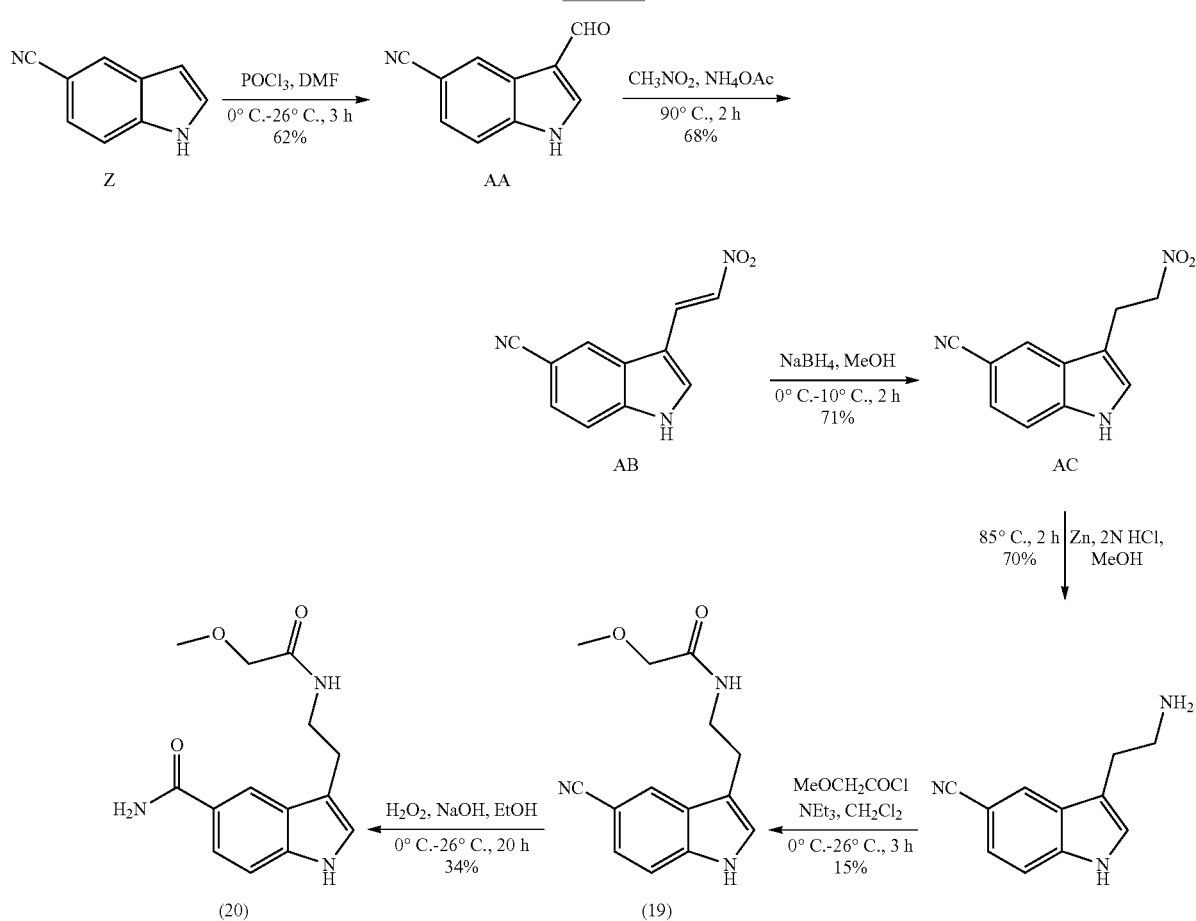

Preparation of Intermediate AA

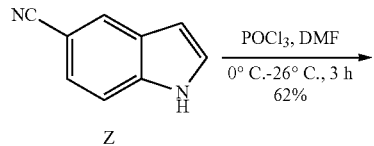

ture was stirred at ambient temperature for 2 hours. The reaction mixture was quenched with ice (25 g), poured into water (50 mL), and NaOH (1.5 g) was added. The mixture was filtered, and the yellow colored filtrate was diluted with water (100 mL) and left to stand at room temperature for 20 hours. The solid was then filtered and dried to afford Intermediate AA (1.5 g, 62%) as a yellow solid. ¹H NMR (DMSO-d₆): δ 12.59 (bs, 1H), 10.00 (s, 1H), 8.52 (s, 1H), 8.51 (s, 1H), 7.71 (s, J=8.29 Hz; 1H), 7.65 (d, J=8.70 Hz; 1H). Mass (M−H): 169.1.

Preparation of Intermediate AB

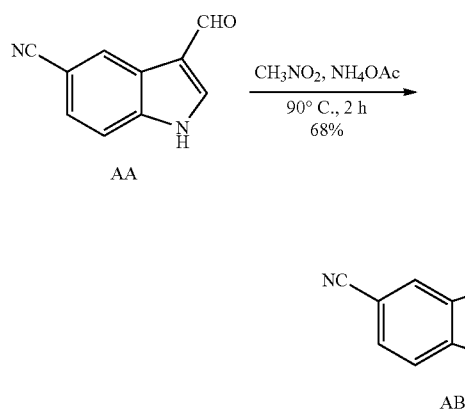

A suspension of Intermediate AA (4.2 g, 24.7 mmol) and ammonium acetate (4.18 g, 54.34 mmol) in nitromethane (263.0 mL) was stirred at 90° C. for 2 hours. The reaction mixture was concentrated under reduced pressure. The crude product was washed with 25% ethyl acetate in petroleum ether (2×20 mL) and dried to afford Intermediate AB (3.5 g, 68%) as yellow solid. $^1$H NMR (DMSO-$d_6$): δ 10.84 (bs, 1H), 8.67 (s, 1H), 8.43-8.40 (m, 2H), 8.23 (d, J=13.66 Hz; 1H), 7.68 (d, J=8.29 Hz; 1H), 7.61 (d, J=8.78 Hz; 1H). Mass (M−H): 212.0.

Preparation of Intermediate AC

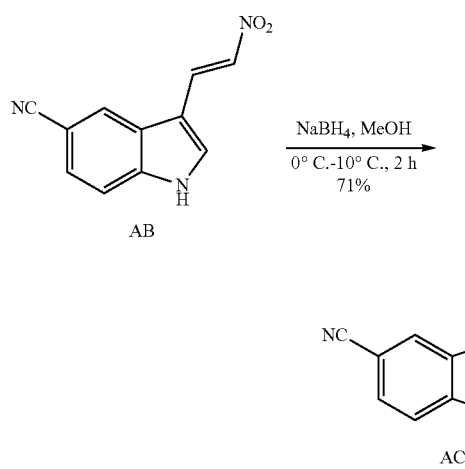

To a cold (0° C.) solution of Intermediate AB (3.5 g, 16.4 mmol) in methanol and DMF (1:1; 35 mL) was added portionwise NaBH$_4$ (7.08 g, 18.73 mmol) over 15 minutes. After the addition was complete, the reaction mixture was allowed to reach 10° C. and stirred for 2 hours.

The reaction mixture was quenched with water (10 mL) and concentrated under reduced pressure. The resulting aqueous residue was diluted with water (25 mL) and extracted with ethyl acetate (2×50 mL). The combined ethyl acetate layers were washed with water (30 mL) and brine solution (25 mL), dried over anhydrous Na$_2$SO$_4$, and the solvent was removed to afford the crude Intermediate AC, which was purified by column chromatography (silica gel 100-200 mesh) using 20% ethyl acetate in petroleum ether as the eluent to afford the product (2.5 g, 71.4%) as pale yellow solid. $^1$H NMR (CDCl$_3$): δ 8.39 (bs, 1H), 7.93 (s, 1H), 7.48- 7.43 (m, 2H), 7.21 (s, 1H), 4.68 (t, J=6.84 Hz, 2H), 3.49 (t, J=6.84 Hz, 2H). Mass (M−H): 214.0.

Preparation of Intermediate AD

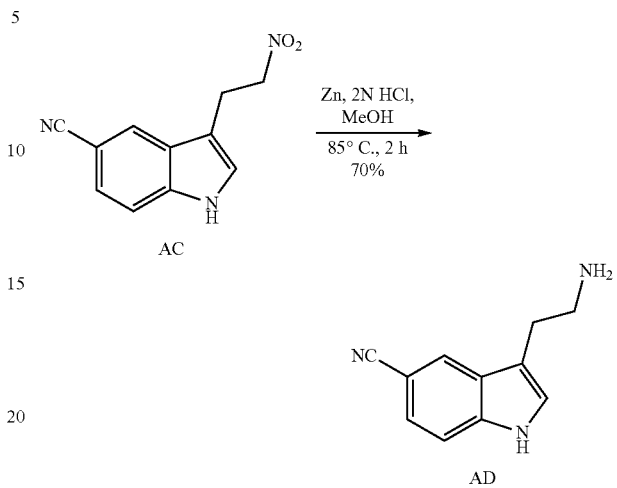

A suspension of Intermediate AC (2.5 g, 11.6 mmol), zinc powder (17.9 g) in methanol (330.0 mL) and 2N HCl (330.0 mL) was stirred at 85° C. for 2 hours. The reaction mixture was basified (pH~10) and filtered. The cake was washed with methanol (3×10 mL), and the combined filtrate was concentrated under reduced pressure. The residue was dissolved in 5% MeOH in chloroform and washed with water. The organic layer was dried over anhydrous Na$_2$SO$_4$, and the solvent was removed to afford the crude Intermediate AD (1.5 g, 70%) as a brown gum. $^1$H NMR (DMSO-$d_6$): δ 11.43 (bs, 1H), 8.09 (s, 1H), 7.49 (d, J=8.49 Hz; 1H), 7.44-7.35 (m, 2H), 2.84-2.77 (m, 4H), 3.29 (t, J=7.03 Hz, 2H). Mass (M+H): 186.0.

Preparation of Compound (19)

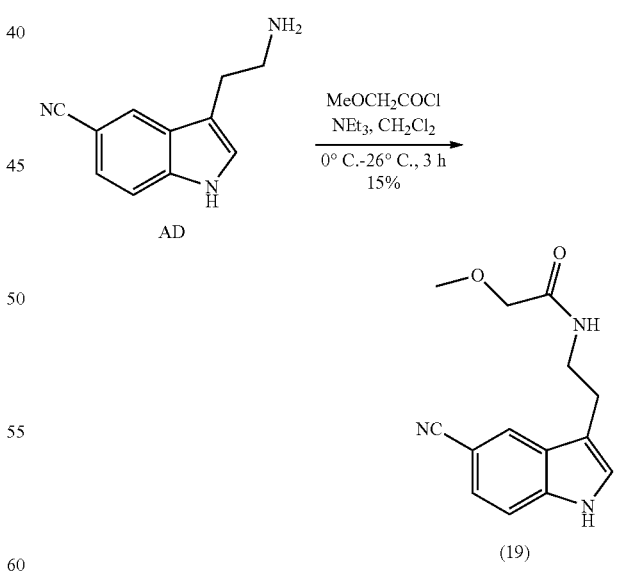

To a cold (0° C.) solution of Intermediate AD (300 mg, 1.62 mmol) and triethylamine (1.3 mL, 3.24 mmol) in dichloromethane (10.0 mL), was added slowly methoxyacetyl chloride (0.22 mL, 2.43 mmol) over 5 minutes. After the addition was complete, the reaction mixture was allowed to reach room temperature and stirred for 3 hours. The reaction mixture was diluted with dichloromethane (30 mL), washed with water (2×15 mL) and brine (20 mL), dried over anhydrous Na₂SO₄, and removal of the solvent yielded the crude product. This material was purified by column chromatography (silica gel 100-200 mesh) using 2% MeOH in chloroform as the eluent to afford Compound (19) (60 mg, 15%) as a pale brown gum. ¹H NMR (DMSO-d₆): δ 11.42 (bs, 1H), 8.11 (s, 1H), 7.89 (t, J=5.59 Hz; 1H), 7.49 (d, J=8.29 Hz; 1H), 7.42-7.37 (m, 2H), 3.76 (s, 2H), 3.40-3.34 (m, 2H), 3.32 (s, 3H), 2.87 (t, J=7.25 Hz; 2H). Mass (M+H): 258M. IR (cm⁻¹): 3386, 3210, 2921, 2222, 1651, 1542, 1124, 639. HPLC purity (%): 94.72 (Max plot), 92.32 (254 nm), 94.91 (215 nm).

Preparation of Compound (20)

To a cold (0° C.) solution of Compound (19) (50 mg, 0.194 mmol) and 3N NaOH (2.5 mL) in ethanol (3.5 mL) was added H₂O₂ (30% in water; 0.2 mL). After the addition was complete, the reaction mixture was allowed to reach room temperature and stirred for 20 hours.

The reaction mixture was concentrated, and the obtained aqueous residue was diluted with dichloromethane (50 mL), washed with water (2×10 mL) and brine (10 mL), dried over anhydrous Na₂SO₄, and the solvent was removed to afford the crude product. This material was purified by column chromatography (silica gel 100-200 mesh) using 8% MeOH in chloroform as the eluent to afford Compound (20) (36 mg, 33.6%) as a pale brown gum. ¹H NMR (DMSO-d₆): 11.03 (bs, 1H), 8.17 (s, 1H), 7.83-7.78 (m, 2H), 7.63 (d, J=8.2 Hz; 1H), 7.32 (d, J=8.39 Hz; 1H), 7.22 (s, 1H), 7.06 (bs, 1H), 3.78 (s, 2H), 3.42-3.41 (m, 2H), 3.32 (s, 3H), 2.88 (t, J=6.93 Hz; 2H). Mass (M+H): 275.9. IR (cm⁻¹): 3433, 32923, 1645, 1239, 789. HPLC purity (%): 89.89 (Max plot), 95.47 (254 nm), 90.40 (215 nm).

Synthesis of Compound (21)

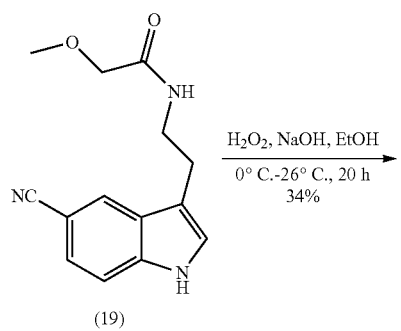

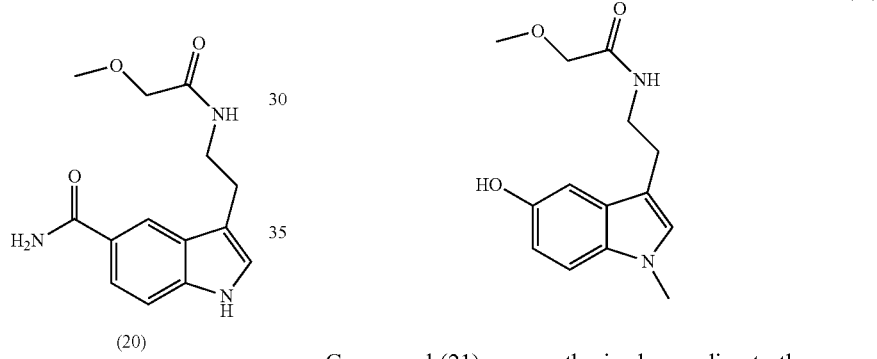

Compound (21) was synthesized according to the procedure shown in Scheme 15.

Scheme 15

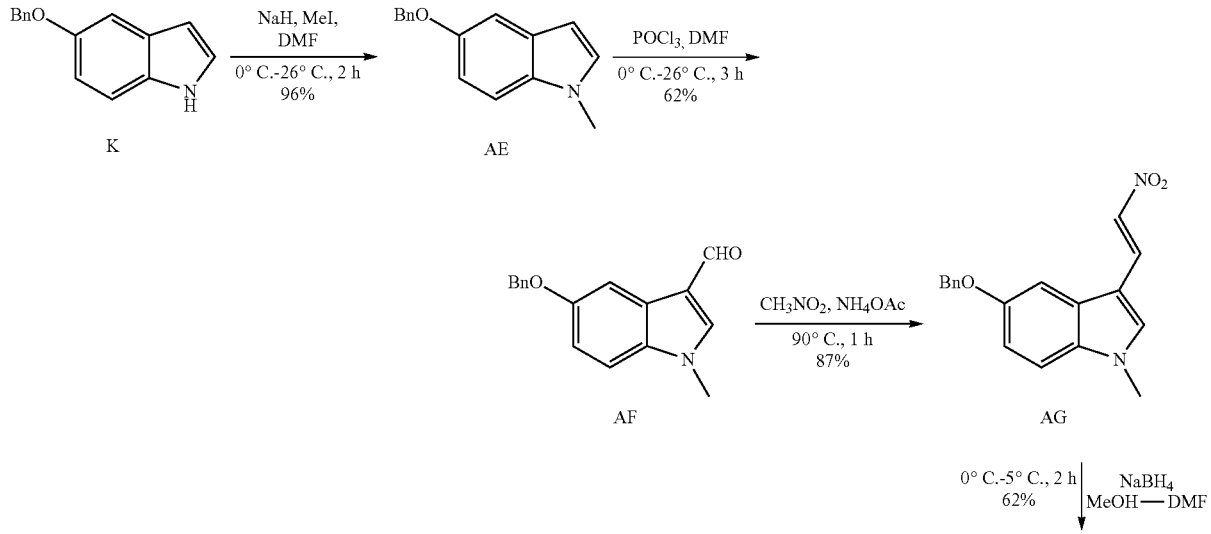

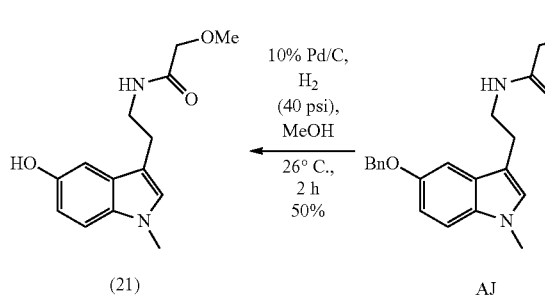
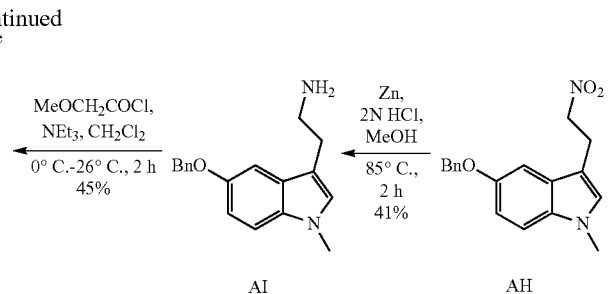

Preparation of Intermediate AE

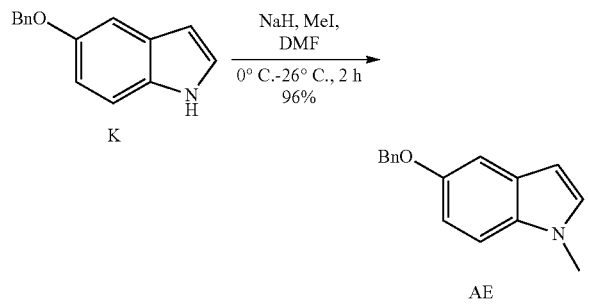

To a cold (0° C.) suspension of 60% NaH (0.51 g, 15.71 mmol) in DMF (10.0 mL), a solution of Intermediate K (3.0 g, 13.43 mmol) in DMF (10.0 mL) was added slowly over 5 minutes. The reaction stirred for 30 minutes; iodomethane (0.98 mL, 15.71 mmol) was then added, and the reaction stirred at room temperature for 1.5 hours. The reaction mixture was quenched with ice cold water (50 mL) and extracted with ethyl acetate (2×50 mL). The combined ethyl acetate layers were washed with water (2×20 mL) and brine (20 mL), dried over anhydrous $Na_2SO_4$, and the solvent was removed to afford the crude Intermediate AE (520 mg, 96%), which was used in the next step without further purifications. $^1$H NMR ($CDCl_3$): δ 7.48-7.46 (m, 2H), 7.39-7.35 (m, 2H), 7.32-7.28 (m, 1H), 7.24-7.16 (m, 2H), 7.01-6.95 (m, 2H), 6.38 (d, J=2.92 Hz; 1H), 5.10 (s, 2H), 3.75 (s, 3H). Mass (M+H): 238.1.

Preparation of Intermediate AF

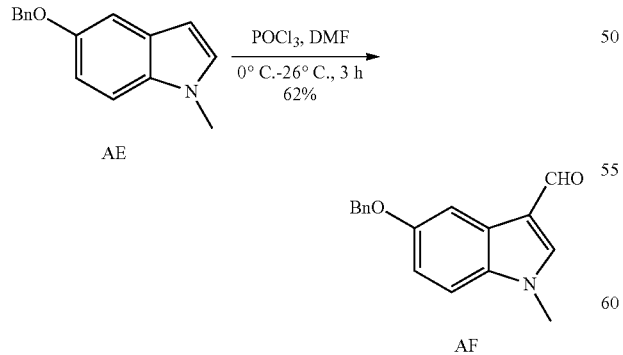

$POCl_3$ (0.21 mL, 2.32 mmol) was added to DMF (1.0 mL) dropwise at 0° C.-10° C. The resulting mixture was stirred for 30 minutes, cooled to 0° C., and a solution of Intermediate AE (0.5 g, 2.11 mmol) in DMF (1.0 mL) was added over 15 minutes. After the addition was complete, the reaction mixture was stirred at ambient temperature for 2 hours. The reaction mixture was quenched with ice (25 g), poured into water (20 mL), and basified (pH~10) using 1N NaOH solution. The mixture was extracted with ethyl acetate (2×50 mL), and the combined ethyl acetate layers were washed with water (2×20 mL) and brine (20 mL), dried over anhydrous $Na_2SO_4$, and removal of the solvent afforded crude Intermediate AF, which was washed with petroleum ether (2×5 mL) and dried to afford the product (480 mg, 85%) as yellow solid. $^1$H NMR ($CDCl_3$): δ 9.95 (s, 1H), 7.91 (s, 1H), 7.62 (s, 1H), 7.50-7.48 (m, 2H), 7.48-7.30 (m, 3H), 7.26-7.24 (m, 2H), 7.08-7.05 (dd, 1H), 5.15 (s, 2H), 3.84 (s, 3H). Mass (M+H): 266.0.

Preparation of Intermediate AG

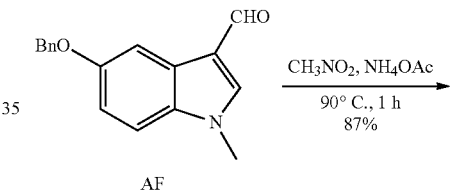

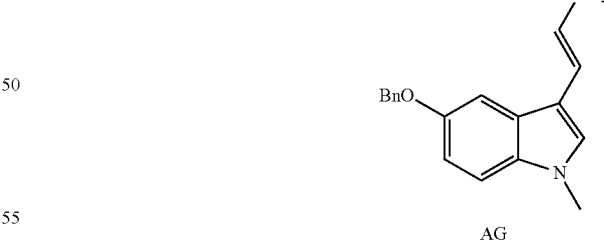

A suspension of Intermediate AF (0.47 g, 1.77 mmol) and ammonium acetate (0.47 g, 6.09 mmol) in nitromethane (33.3 mL) was stirred at 90° C. for 1 hour. The reaction mixture was concentrated under reduced pressure, and the obtained crude product was washed with 25% ethyl acetate in petroleum ether (2×20 mL) and dried to afford Intermediate AG (0.48 g, 87%) as yellow solid. $^1$H NMR (DMSO-$d_6$): δ 8.23 (d, J=13.28 Hz; 1H), 7.65 (d, J=13.28 Hz; 1H), 7.51-7.24 (m, 8H), 7.09-7.07 (m, 1H), 5.16 (s, 2H), 3.83 (s, 3H). Mass (M+H): 309.0.

Preparation of Intermediate AH

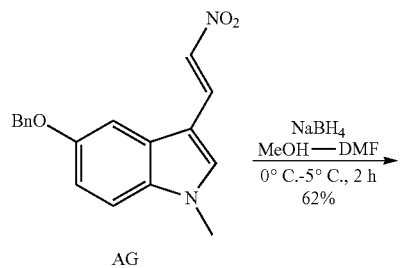

AG

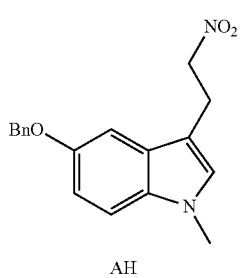

AH

To a cold (0° C.) solution of Intermediate AG (0.7 g, 2.27 mmol) in methanol and DMF (2:1; 15 mL), NaBH$_4$ (0.17 g, 4.54 mmol) was added portionwise over 20 minutes. After the addition was complete, the reaction mixture was stirred at 5° C. for 2 hours. The reaction mixture was quenched with water (10 mL) and concentrated under reduced pressure. The resulting aqueous residue was diluted with water (10 mL) and extracted with ethyl acetate (2×20 mL). The combined ethyl acetate layers were washed with water (10 mL) and brine solution (10 mL), dried over anhydrous Na$_2$SO$_4$, and the solvent was removed to afford the crude product, which was purified by column chromatography (silica gel 100-200 mesh) using 20% ethyl acetate in petroleum ether as the eluent to afford Intermediate AH (440 mg, 62%) as a pale yellow solid.

$^1$H NMR (CDCl$_3$): δ 7.49-7.47 (m, 2H), 7.41-7.32 (m, 3H), 7.20 (d, J=9.12 Hz; 1H), 7.06-7.05 (s, 1H), 7.00-6.97 (m, 1H), 6.88 (s, 1H), 5.11 (s, 2H), 4.60 (t, J=7.25 Hz; 2H), 3.71 (s, 3H), 3.42 (t, J=7.25 Hz; 2H). Mass (M+H): 311.1.

Preparation of Intermediate AI

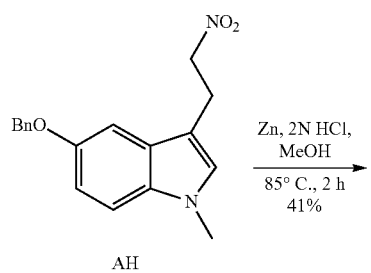

AH

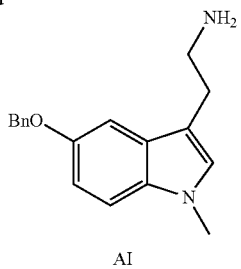

AI

A suspension of Intermediate AH (430 mg, 1.381 mmol) and zinc powder (2.13 mg, 32.59 mmol) in methanol (57.0 mL) and 2N HCl (57.0 mL) was stirred at 65° C. for 2 hours. The reaction mixture was basified (pH~10) and filtered. The cake was washed with methanol (3×10 mL), and the combined filtrate was concentrated under reduced pressure. The residue was dissolved in 5% MeOH in chloroform (150 mL) and washed with water (20 mL). The organic layer was dried over anhydrous Na$_2$SO$_4$, and the solvent was removed to afford the crude Intermediate AI (160 mg, 41%) as a brown gum. $^1$H NMR (DMSO-d$_6$): δ 7.48-7.25 (m, 6H), 7.12-7.06 (m, 2H), 6.86-6.83 (m, 1H), 5.09 (s, 2H), 3.68 (s, 3H), 2.79-2.68 (m, 4H). Mass (M+H): 281.1.

Preparation of Intermediate AJ

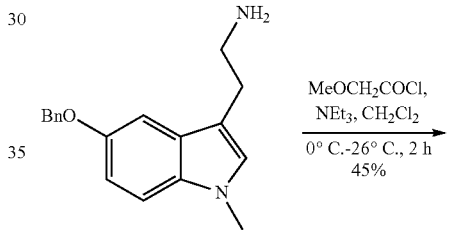

AJ

To a cold (0° C.) solution of Intermediate AI (150 mg, 0.535 mmol) and triethylamine (0.15 mL, 1.07 mmol) in dichloromethane (10.0 mL) was added slowly a solution of methoxyacetyl chloride (0.06 mL, 0.64 mmol) in dichloromethane (2.0 mL) over 5 minutes. After the addition was complete, the reaction mixture was allowed to reach room temperature and stirred for 2 hours. The reaction mixture was diluted with water (10 mL) and extracted with dichloromethane (2×20 mL). The combined dichloromethane layer was washed with water (10 mL) and brine (10 mL), dried over anhydrous Na$_2$SO$_4$, and the solvent was removed to afford the crude product, which was purified by column chromatography (silica gel 100-200 mesh) using 2% MeOH in chloroform as the eluent to afford Intermediate AJ (85 mg, 45%) as a brown gum. $^1$H NMR (CDCl$_3$): δ 7.49-7.47 (m, 2H), 7.41-7.30 (m, 3H), 7.21-7.13 (m, 2H), 6.99-6.96 (m, 1H), 6.87 (s, 1H), 6.63 (bs, 1H), 5.11 (s, 2H), 3.87 (s, 2H), 3.72 (s, 3H), 3.64-3.57 (m, 2H), 3.33 (s, 3H), 2.93 (t, J=6.84 Hz; 2H). Mass (M+H): 353.1.

Preparation of Compound (21)

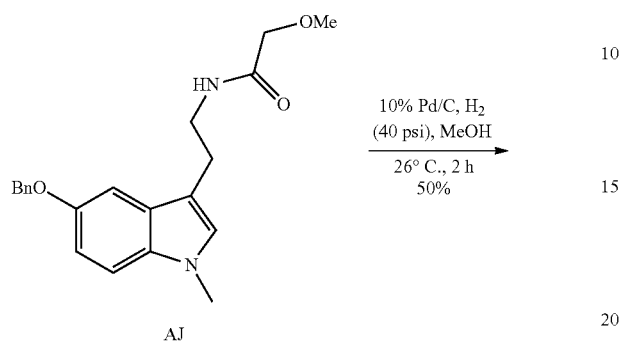

A suspension of Intermediate AJ (80 mg, 0.227 mmol) and 10% Pd/C (40 mg, dry) in MeOH (10.0 mL) was hydrogenated (40 psi H$_2$ pressure) at room temperature for 2 hours. The reaction mixture was filtered through a Celite bed, and the cake was washed with methanol (3×5 mL). The combined filtrates were concentrated under reduced pressure to give the crude product, which was purified by column chromatography (silica gel 100-200 mesh) using 2% MeOH in chloroform as the eluent to afford Compound (21) (30 mg, 50%) as a brown solid. $^1$H NMR (CDCl$_3$): δ 7.15 (d, J=8.85 Hz; 1H), 7.02 (s, 1H), 6.85-6.80 (m, 2H), 6.66 (bs, 5.02 (s, 1H), 3.88 (s, 2H), 3.71 (s, 3H), 3.61-3.56 (m, 2H), 3.33 (s, 3H), 2.91 (t, J=6.97 Hz; 2H). Mass (M+H): 262.9. IR (cm$^{-1}$): 3400, 2926, 1651, 1219, 1114, 771. HPLC purity (%): 93.49 (Max plot), 94.77 (254 nm), 97.19 (215 nm).

Synthesis of Compounds (22) and (23)

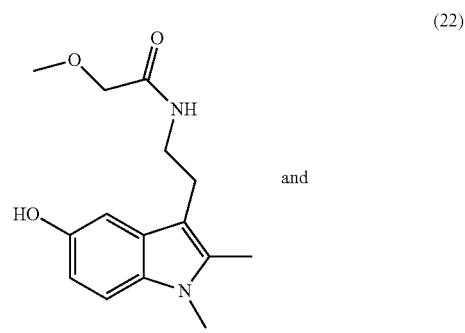

Compounds (22) and (23) were prepared according to the procedure shown in Scheme 16.

Scheme 16

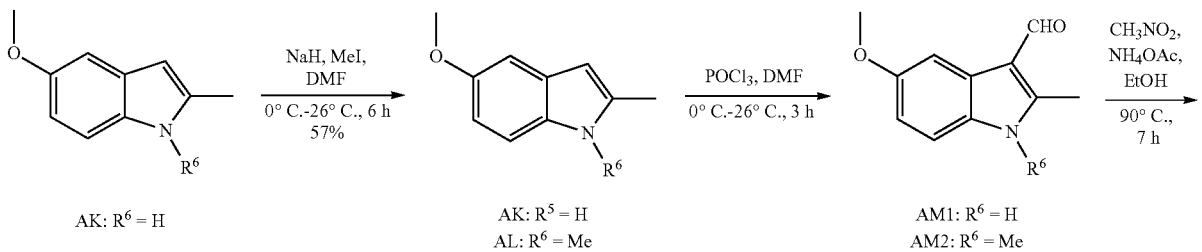

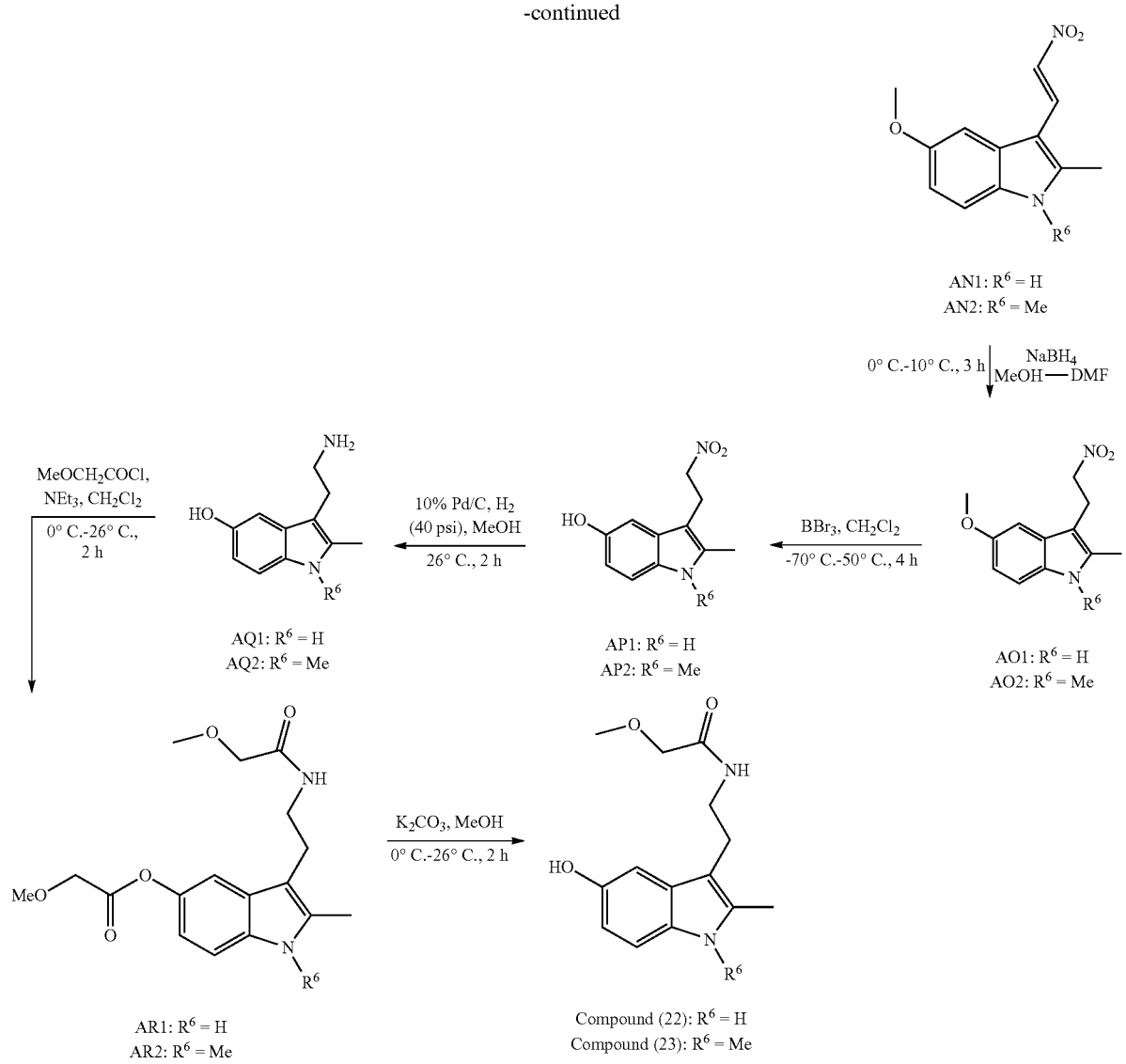

Preparation of Intermediate AL

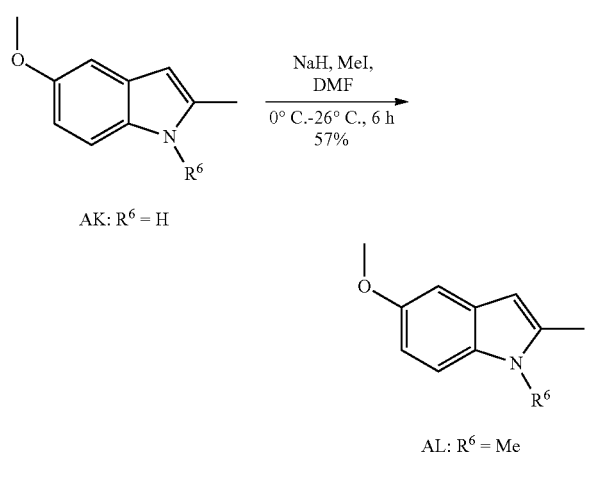

To a cold (0° C.) suspension of 60% NaH (0.58 g, 14.51 mmol) in DMF (10.0 mL) was added slowly a solution of Intermediate AK (2.0 g, 12.40 mmol) in DMF (5.0 mL) was added slowly for 5 minutes. The reaction was then stirred for 30 minutes, and iodomethane (2.06 g, 14.52 mmol) was then added to the reaction mixture. The reaction stirred at room temperature for 5 hours. The reaction mixture was quenched with ice cold water (25 mL) and extracted with ethyl acetate (3×30 mL). The combined ethyl acetate layers were washed with water (2×20 mL) and brine (20 mL), dried over anhydrous $Na_2SO_4$, and the solvent was removed to afford the crude Intermediate AL which was purified by column chromatography (silica gel 100-200 mesh) using 12% ethyl acetate in petroleum ether as the eluent to afford the product (1.25 g, 57%) as a brown solid. $^1$H NMR ($CDCl_3$): δ 7.13 (d, J=8.78 Hz; 1H), 7.00 (s, 1H), 6.81-6.78 (dd, 1H), 6.16 (s, 1H), 3.83 (s, 3H), 3.62 (s, 3H), 2.39 (s, 3H). Mass (M+H): 176.0.

Preparation of Intermediates AM1 and AM2

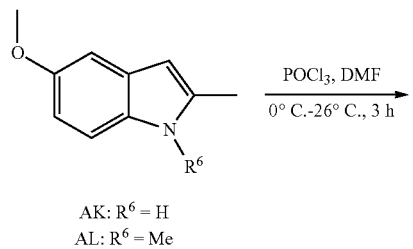

AK: R⁶ = H
AL: R⁶ = Me

Preparation of Intermediates AN1 and AN2

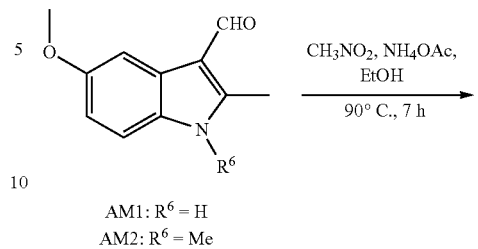

AM1: R⁶ = H
AM2: R⁶ = Me

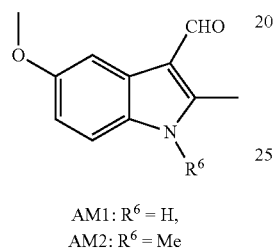

AM1: R⁶ = H,
AM2: R⁶ = Me

General Procedure. POCl$_3$ (1.1 mmol) was added to DMF (2.0 mL) dropwise at 0° C.-10° C. The resulting mixture was stirred for 30 minutes, cooled to 0° C., and a solution of Intermediate AK or Intermediate AL (1.0 mmol) in DMF (2.0 mL) was added over 15 minutes. After the addition was complete, the reaction mixture was stirred at ambient temperature for 2 hours. The reaction mixture was quenched with ice (25 g), poured into water (30 mL), and basified (pH~10) using a 1N NaOH solution. The mixture was extracted using ethyl acetate (3×20 mL), washed with water (2×10 mL) and brine (15 mL), and dried over anhydrous Na$_2$SO$_4$, and removal of the solvent afforded Intermediate AM1 or AM2 (Table 10).

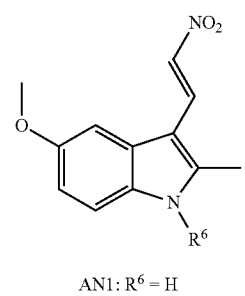

AN1: R⁶ = H
AN2: R⁶ = Me

A suspension of Intermediate AM1 or AM2 (1.0 mmol), ammonium acetate (3.43 mmol) in nitromethane (80 mL) was stirred at 90° C. for 7 hours. The reaction mixture was concentrated under reduced pressure. The resulting crude product was dissolved in ethyl acetate (100 mL), washed with water (2×30 mL) and brine solution (25 mL), dried over anhydrous Na$_2$SO$_4$, and the solvent was removed to afford the crude Intermediate AN (Table 11).

TABLE 10

| | |
|---|---|
| AM1 | Intermediate AK (2.0 g, 12.4 mmol) was reacted with POCl$_3$ (1.67 mL, 13.64 mmol) in DMF (8.0 mL) to give Intermediate AM1 (1.7 g, 72%) as a pale brown solid. $^1$H NMR (CDCl$_3$): δ 10.15 (s, 1H), 8.35 (bs, 1H), 7.77 (s, 1H), 7.21 (d, J = 8.78 Hz; 1H), 6.88 (dd, 1H), 3.88 (s, 3H), 2.72 (s, 3H). Mass (M + H): 189.9. |
| AM2 | Intermediate AL (1.25 g, 7.14 mmol) was reacted with POCl$_3$ (0.74 mL, 7.85 mmol) in DMF (10.0 mL) to give Intermediate AM2 (1.2 g, 82%) as a pale brown solid. $^1$H NMR (CDCl$_3$): δ 10.12 (s, 1H), 7.80 (s, 1H), 7.19 (d, J = 8.85 Hz; 1H), 6.91 (dd, 1H), 3.89 (s, 3H), 3.68 (s, 3H), 2.66 (s, 3H), Mass (M + H): 203.9. |

TABLE 11

| | | |
|---|---|---|
| AN1 | (structure: 5-methoxy-2-methyl-3-(2-nitrovinyl)-1H-indole) | Intermediate AM1 (1.7 g, 8.99 mmol) was reacted with ammonium acetate (2.3 g, 30.85 mmol) in nitromethane (120.0 ml,) to give Intermediate AN1 (2.1 g, 98%) as a yellow solid. $^1$H NMR (CDCl$_3$): δ 8.52 (bs, 1H), 8.33 (d, J = 13.42 Hz; 1H), 7.71 (d, J = 13.42 Hz; 1H), 7.27-7.25 (m, 1H), 7.11 (d, 1H), 6.91-6.89 (m, 1H), 3.90 (s, 3H), 2.62 (s, 3H). Mass (M + H): 203.9. |
| AN2 | (structure: 5-methoxy-1,2-dimethyl-3-(2-nitrovinyl)-1H-indole) | Intermediate AM2 (1.2 g, 5.91 mmol) was reacted with ammonium acetate (1.56 g, 20.27 mmol) in nitromethane (85.0 mL) to give Intermediate AN2 (1.4 g, 96%) as a pale yellow solid. $^1$H NMR (CDCl$_3$): δ 8.33 (d, J = 13.15 Hz; 1H), 7.71 (d, J = 13.15 Hz; 1H), 7.26-7.23 (m, 1H), 7.12 (s, 1H), 6.95-6.92 (m, 1H), 3.90 (s, 3H), 3.72 (s, 3H), 2.62 (s, 3H). Mass (M + H): 246.9. |

Preparation of Intermediates AO1 and AO2

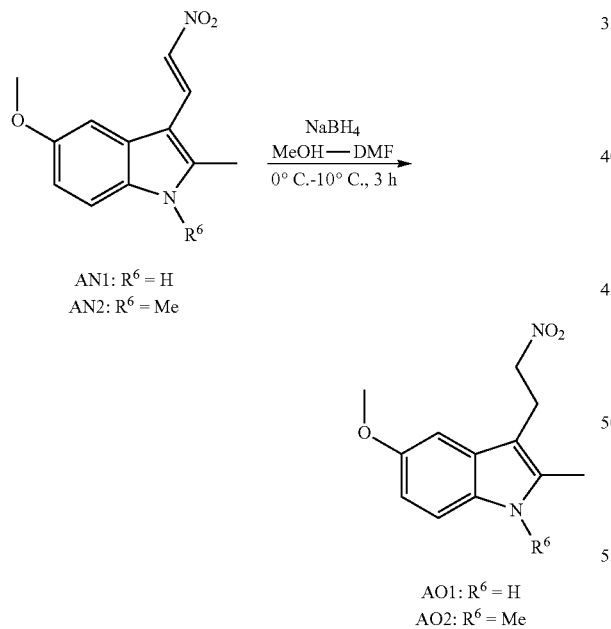

AO1: R$^6$ = H
AO2: R$^6$ = Me

To a cold (0° C.) solution of Intermediate AN1 or AN2 (1.0 mmol) in methanol and DMF (1:1; 35 mL), was added portionwise NaBH$_4$ (2.0 mmol) over 20 minutes. After the addition was complete, the reaction mixture was allowed to stir at 10° C. for 2 hours. The reaction mixture was quenched with water (10 mL) and concentrated under reduced pressure. The resulting aqueous residue was diluted with water (20 mL) and extracted with ethyl acetate (2×30 mL). The combined ethyl acetate layers were washed with water (2×20 mL) and brine solution (20 mL), dried over anhydrous Na$_2$SO$_4$, and the solvent was removed to afford the crude Intermediate AO (Table 12).

TABLE 12

| | | |
|---|---|---|
| AO1 | (structure) | Intermediate AN1 (1.0 g, 4.74 mmol) was reacted with NaBH$_4$ (360 mg, 9.48 mmol) in MeOH (40.0 mL) to give Intermediate AO1 (1.1 g, crude) as a pale brown gum. $^1$H NMR (CDCl$_3$): δ 7.75 (bs, 1H), 7.17 (d, J = 8.70 Hz; 1H), 6.90 (s, 1H), 6.81-6.78 (m, 1H), 4.57 (t, J = 7.25 Hz; 2H), 3.86 (s, 3H), 3.40 (t, J = 7.46 Hz, 2H), 2.37 (s, 3H). Mass (M + H): 235.1. |
| AO2 | (structure) | Intermediate AN2 (1.3 g, 5.28 mmol) was reacted with NaBH$_4$ (400 mg, 10.56 mmol) in MeOH (45.0 mL) to give Intermediate AO2 (1.4 g, crude) as a pale brown gum. $^1$H NMR (CDCl$_3$): δ 7.15 (d, J = 8.70 Hz; 1H), 6.91 (s, 1H), 6.85-6.84 (m, 1H), 4.55 (t, J = 7.46 Hz; 2H), 3.86 (s, 3H), 3.62 (s, 3H), 3.42 (t, J = 7.46 Hz, 2H), 2.34 (s, 3H). Mass (M + H): 249.1. |

Preparation of Intermediate AP1 and AP2

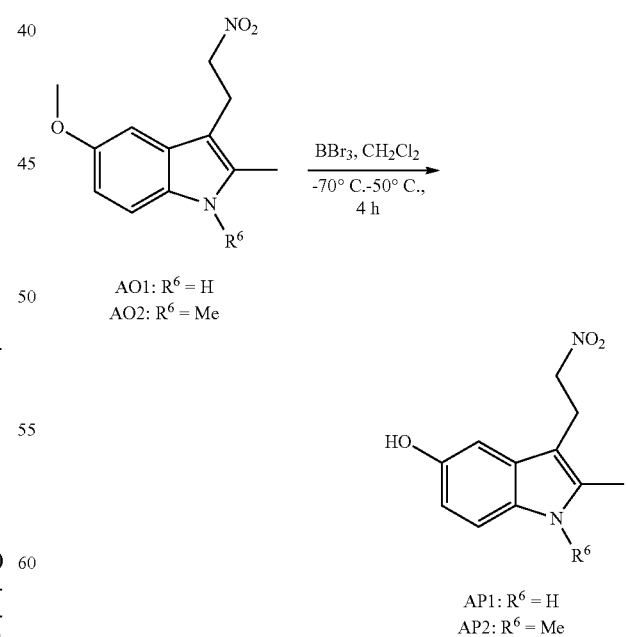

AO1: R$^6$ = H
AO2: R$^6$ = Me

AP1: R$^6$ = H
AP2: R$^6$ = Me

To a cold (−70° C.) solution of Intermediate AO (1.0 mmol) in dichloromethane (~30 mL) was added slowly BBr$_3$ (2.0 mmol). After the addition was complete, the reaction mixture was allowed to reach 0° C. and stirred for 4 hours. The reaction mixture was diluted with dichloromethane (25 mL), washed with water (2×10 mL) and brine (20 mL), dried over anhydrous Na$_2$SO$_4$, and the solvent was removed to afford the crude Intermediate AP, each of which was purified by column chromatography (silica gel 100-200 mesh) using 20% ethyl acetate in petroleum ether as the eluent (Table 13).

A suspension of Intermediate AP (1.0 mmol) and 10% Pd/C (60% w/w, dry) in MeOH (30 mL) was hydrogenated (40 psi H$_2$ pressure) at 26° C. for 2 hours. The reaction mixture was filtered, the cake was washed with methanol (3×5 mL), and the combined filtrates were concentrated under reduced pressure to afford Intermediates AQ (Table 14), which was used as such in the next step.

TABLE 13

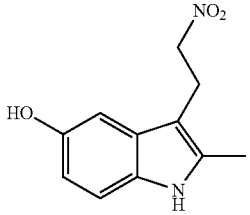 [SMILES: Cc1[nH]c2ccc(O)cc2c1CC[N+](=O)[O-]]

| AP1 | (structure) | Intermediate AO1 (600 mg, 2.56 mmol) was reacted with BBr$_3$ (0.74 mL, 5.12 mmol) in dichloromethane (20.0 mL) to give Intermediate AP1 (100 mg, 18%) as a pale brown gum. $^1$H NMR (CDCl$_3$): δ 7.75 (bs, 1H), 7.12 (d, J = 8.78 Hz; 1H), 6.86 (s, 1H), 6.71-6.68 (m, 1H), 4.73 (bs, 1H), 4.54 (t, J = 7.31 Hz; 2H), 3.35 (t, J = 7.31 Hz, 2H), 2.36 (s, 3H). Mass (M + H): 221.0. |
| AP2 | (structure) | Intermediate AO2 (600 mg, 2.41 mmol) was reacted with BBr$_3$ (0.47 mL, 4.84 mmol) in dichloromethane (20.0 mL) to give Intermediate AP2 (75 mg, 13%) as a pale brown gum. $^1$H NMR (CDCl$_3$): δ 7.11 (d, J = 8.70 Hz; 1H), 6.89 (s, 1H), 6.75-6.72 (m, 1H), 4.56-4.50 (m, 2H), 3.61 (s, 3H), 3.37 (t, J = 7.46 Hz, 2H), 2.34 (s, 3H). |

TABLE 14

| AQ1 | (structure) | Intermediate AP1 (100 mg, 0.454 mmol) was hydrogenated with 10% Pd/C (60 mg) in MeOH (20.0 mL) to give Intermediate AQ1 (80 mg, crude) as a pale brown gum. Mass (M + H): 191.1. |
| AQ2 | (structure) | Intermediate AP2 (125 mg, 0.53 mmol) was hydrogenated with 10% Pd/C (70 mg) in MeOH (20.0 mL) to give Intermediate AQ2 (108 mg, crude) as a pale brown gum. Mass (M + H): 205.1. |

Preparation of Intermediates AR1 and AR2

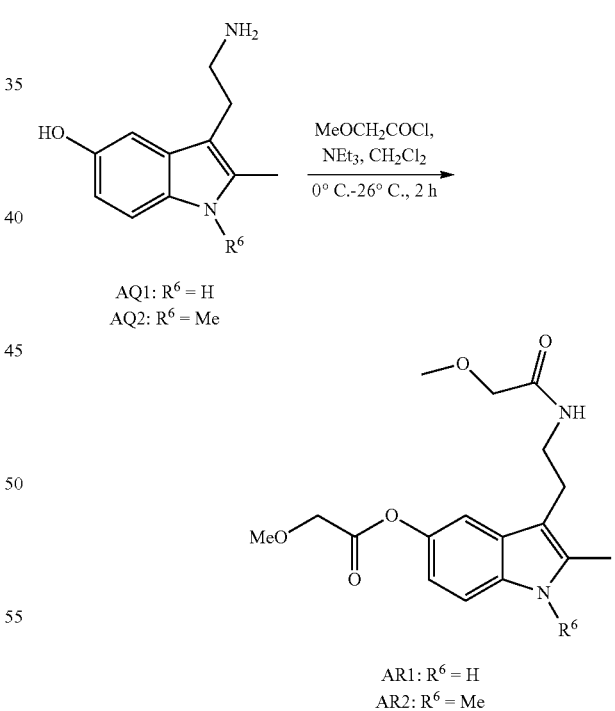

AQ1: R$^6$ = H
AQ2: R$^6$ = Me

AR1: R$^6$ = H
AR2: R$^6$ = Me

Preparation of Intermediates AQ1 and AQ2

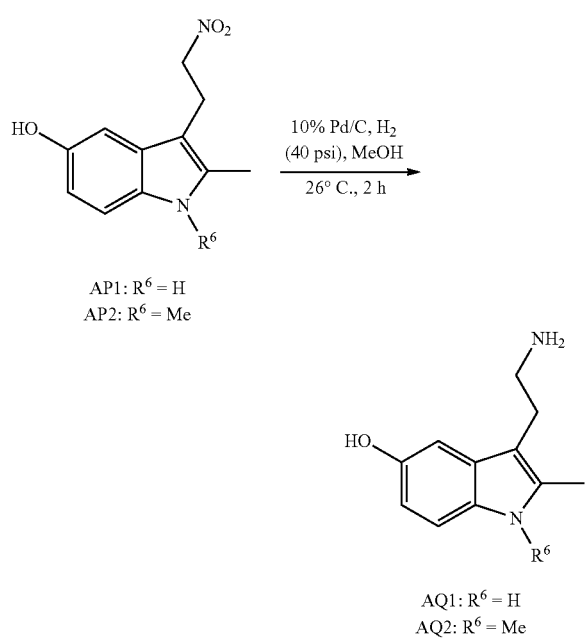

AP1: R$^6$ = H
AP2: R$^6$ = Me

AQ1: R$^6$ = H
AQ2: R$^6$ = Me

To a cold (0° C.) solution of crude Intermediate AQ (1.0 mmol) and triethylamine (2.2 mmol) in dichloromethane (20 mL), methoxyacetyl chloride (2.2 mmol) was added slowly over 5 minutes. After the addition was complete, the reaction mixture was allowed to reach room temperature and stirred for 2 hours. The reaction mixture was diluted with dichloromethane (25 mL), washed with water (2×10 mL) and brine (20 mL), dried over anhydrous Na$_2$SO$_4$, and the solvent was removed to afford the crude Intermediate AR (Table 15), which was purified by column chromatography (silica gel 100-200 mesh) using 20% ethyl acetate in petroleum ether as the eluent.

TABLE 15

| AR1 | | Intermediate AQ1 (80 mg, 0.42 mmol) was reacted with methoxyacetyl chloride (0.04 mL, 0.42 mmol) and Et$_3$N (0.06 mL, 0.46 mmol) in dichloromethane (15.0 mL) to give Intermediate AR1 (46 mg, 33%) as a pale brown gum. $^1$H NMR (CDCl$_3$): δ 7.87 (bs, 1H), 7.23-7.21 (m, 2H), 6.87-6.84 (m, 1H), 6.58 (bs, 1H), 4.31 (s, 2H), 3.85 (s, 2H), 3.56 (s, 3H), 3.53-3.48 (q, 2H), 3.31 (s, 3H), 2.90-2.86 (m, 2H), 2.38 (s, 3H). Mass (M + H): 335.1. |
| AR2 | | Intermediate AQ2 (108 mg, 0.53 mmol) was reacted with methoxyacetyl chloride (0.11 mL, 1.16 mmol) and Et$_3$N (0.18 mL, 1.164 mmol) in dichloromethane (15.0 mL) to give Intermediate AR2 (40 mg, 22%) as a pale brown gum. $^1$H NMR (CDCl$_3$): δ 7.23-7.21 (m, 2H), 6.91-6.88 (m, 1H), 6.76 (bs, 1H), 4.31 (s, 2H), 3.85 (s, 2H), 3.66 (s, 3H), 3.51-3.46 (m, 2H), 3.31 (s, 3H), 2.91 (t, J = 7.05 Hz; 2H), 2.36 (s, 3H). Mass (M + H): 363.1. |

Preparation of Compounds (22) and (23)

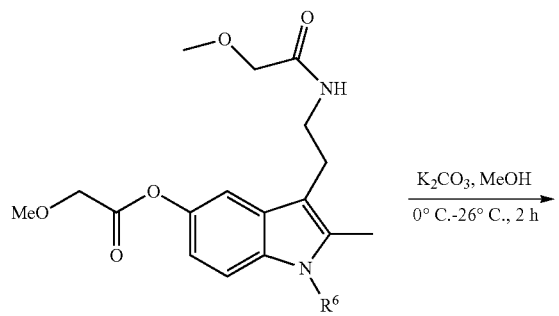

AR1: R$^6$ = H
AR2: R$^6$ = Me

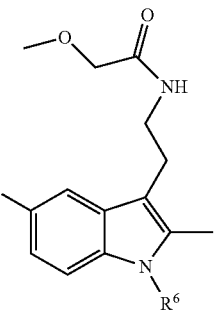

Compound (22): R$^6$ = H
Compound (23): R$^6$ = Me

A suspension of Intermediate AR (1.0 mmol) and K$_2$CO$_3$ (1.1 mmol) in methanol (20 mL) was stirred at 26° C. for 2 hours. The reaction mixture was concentrated and the residue was diluted with water (20 mL) and extracted with ethyl acetate (2×20 mL). The combined ethyl acetate layers were washed with brine (2×10 mL), dried over anhydrous Na$_2$SO$_4$, and concentrated to afford the crude product, which was purified by PREP-TLC using 70% ethyl acetate in petroleum ether as the eluent to afford the corresponding Compounds (22) and (23) (Table 16).

TABLE 16

| (22) | | Intermediate AR1 (46 mg, 0.14 mmol) was reacted with K$_2$CO$_3$ (20 mg, 0.15 mmol) in MeOH (3.0 mL) to give Compound (22) (15 mg, 36%) as a pale brown gum. $^1$H NMR (CDCl$_3$): δ 7.65 (bs, 1H), 7.13 (d, J = 8.70 Hz; 1H), 6.94 (s, 1H), 6.70-6.68 (m, 1H), 6.62 (bs, 1H), 4.79 (bs, 1H), 3.86 (s, 2H), 3.54-3.49 (m, 2H), 3.32 (s, 3H), 2.86 (t, J = 6.84 Hz; 2H), 2.35 (s, 3H). Mass (M + H): 263.1. IR (cm$^{-1}$): 3382, 2923, 1649, 1200, 1114, 799. HPLC purity (%): 97.01 (Max plot), 95.28 (254 nm), 97.22 (215 nm). |

91
TABLE 16-continued
| (23) | | Intermediate AR2 (40 mg, 0.114 mmol) was reacted with K$_2$CO$_3$ (17 mg, 0.126 mmol) in MeOH (3.0 mL) to give Compound (23) (14 mg, 38%) Pale brown solid. $^1$H NMR (CDCl$_3$): δ 7.10 (d, J = 8.78 Hz; 1H), 6.96 (s, 1H), 6.75-6.72 (m, 1H), 6.65 (bs, 1H), 4.93 (bs, 1H), 3.86 (s, 2H), 3.62 (s, 3H), 3.51-3.46 (m, 2H), 3.31 (s, 3H), 2.89 (t, J = 6.83 Hz; 2H), 2.33 (s, 3H). Mass (M + H): 277.1. IR (cm$^{-1}$): 3378, 2925, 1661, 1211, 1116, 795. HPLC purity (%): 93.05 (Max plot), 80.02 (254 nm), 93.42 (215 nm). |
|---|---|---|
92
Synthesis of Compound (24)
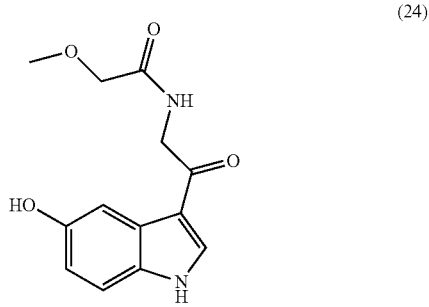 [SMILES: COCC(=O)NCC(=O)c1c[nH]c2ccc(O)cc12]
Compound (24) was synthesized according to the procedure shown in Scheme 17.
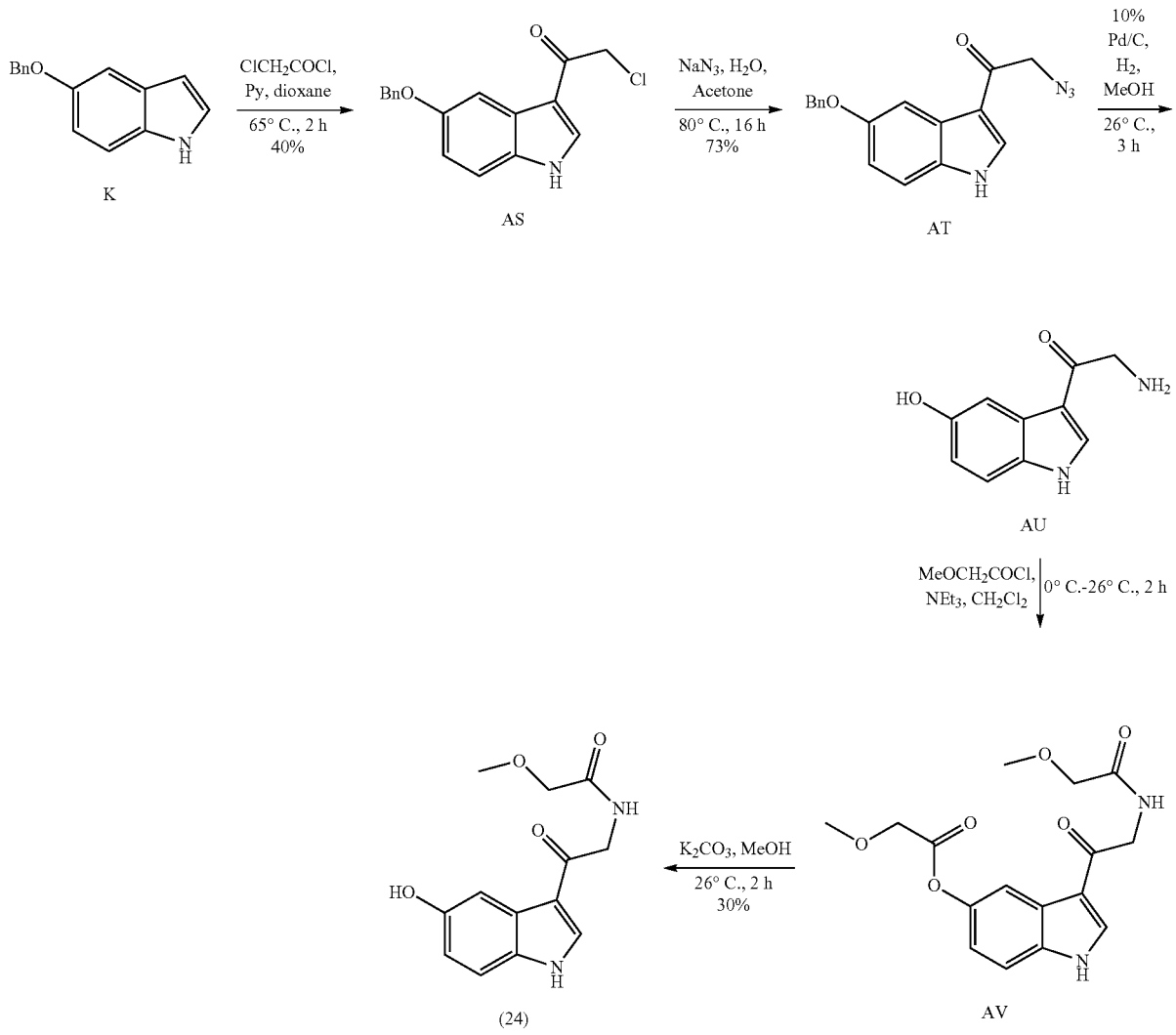

Preparation of Intermediate AS

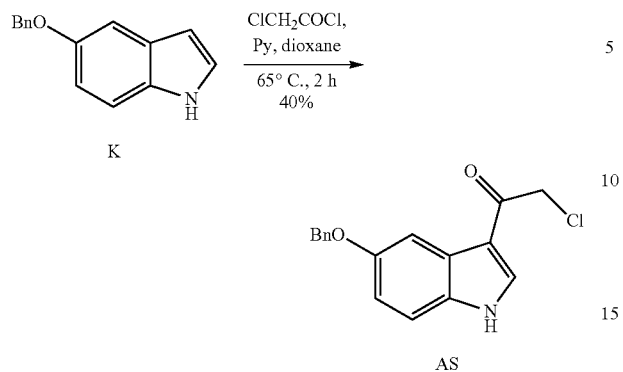

A solution of Intermediate K (3.0 g, 13.45 mmol) and pyridine (1.8 mL, 22.86 mmol) in dioxane (25.0 mL) was stirred at 65° C. for 1 hour. A solution of chloroacetyl chloride (1.8 mL, 22.86 mmol) in dioxane (5.0 mL) was then added dropwise. After the addition was complete, the reaction mixture was stirred for 1 hour. The reaction mixture was cooled, poured into cold ether (150 mL), and stirred. The resulting solid was filtered, washed with cold ether (2×20 mL), and dried to afford crude Intermediate AS (1.6 g, 40%) as a yellow solid. $^1$H NMR (DMSO-$d_6$): δ 12.04 (bs, 1H), 8.38 (s, 1H), 7.76 (s, 1H), 7.49-7.32 (m, 6H), 6.96 (m, 1H), 5.13 (s, 2H), 4.84 (s, 2H). Mass (M+H):300.0.

Preparation of Intermediate AT

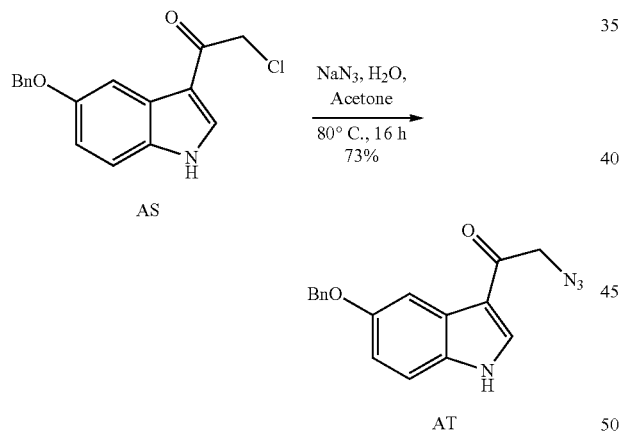

To a solution of Intermediate AS (1.6 g, 5.35 mmol) in acetone (80.0 mL) and water (40.0 mL), was added $NaN_3$ (800 mg, 1.23 mmol) and the resulting reaction mixture was stirred at 80° C. for 16 hours. The reaction mixture was cooled to room temperature, diluted with water (100 mL), and extracted with dichloromethane (2×100 mL). The combined organic layers were washed with water (50 mL) and brine (30 mL), dried over anhydrous $Na_2SO_4$, and the solvent was removed to yield the crude Intermediate AT. This material was washed with petroleum ether (2×10 mL) and dried to afford Intermediate AT (1.2 g, 73%) as a yellow solid.

$^1$H NMR (CDCl$_3$): δ 8.52 (bs, 1H), 7.99 (s, 1H), 7.85 (s, 1H), 7.50 (d, J=7.31 Hz; 1H), 7.41-7.32 (m, 4H), 7.05 (m, 1H), 5.16 (s, 2H), 4.37 (s, 2H). Mass (M-H): 305.0. IR (cm$^{-1}$): 3190, 2924, 2103, 1641, 1259, 746.

Preparation of Intermediate AU

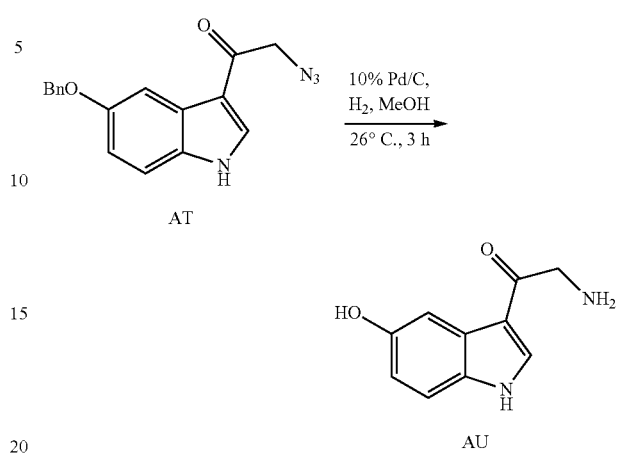

A suspension of Intermediate AT (1.2 g, 3.93 mmol) and 10% Pd/C (750 mg, dry) in MeOH (40.0 mL) was hydrogenated (60 psi $H_2$ pressure) at room temperature for 3 hours. The reaction mixture was filtered, and the cake was washed with methanol (3×5 mL). The combined filtrates were concentrated under reduced pressure to afford Intermediate AU (750 mg, crude) as a brown solid, which was used without further purification in the next step. Mass (M+H): 191.0.

Preparation of Intermediate AV

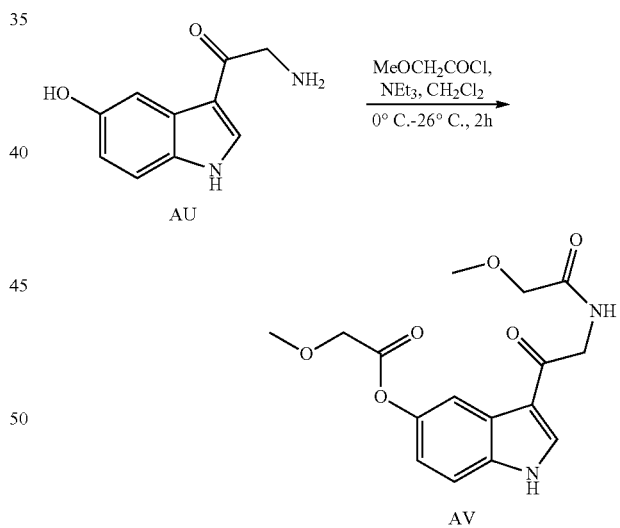

To a cold (0° C.) solution of Intermediate AU (500 mg, 2.63 mmol) and triethylamine (1.09 mL, 7.89 mmol) in dichloromethane (20.0 mL) was added slowly methoxyacetyl chloride (430 mg, 3.94 mmol) over 5 minutes. After the addition was complete, the reaction mixture was allowed to reach room temperature and stirred for 2 hours. The reaction mixture was diluted with dichloromethane (50 mL), washed with water (2×20 mL) and brine (20 mL), dried over anhydrous $Na_2SO_4$, and the solvent was removed to afford the crude Intermediate AV (800 mg, crude) which was used in next step without further purification.

Preparation of Compound (24)

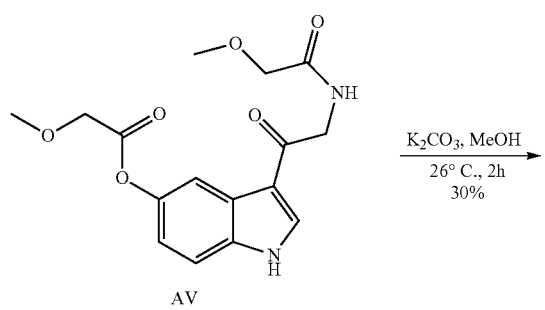

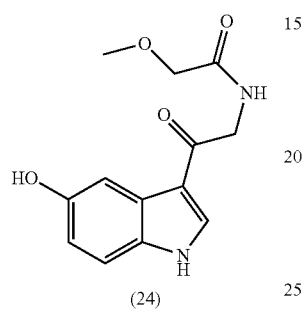

A suspension of crude Intermediate AV (800 mg, 2.63 mmol) and K$_2$CO$_3$ (363 mg, 2.63 mmol) in methanol (15.0 mL) was stirred at 26° C. for 1 hour. The reaction mixture was concentrated under reduced pressure; the residue was diluted with water (20 mL) and extracted with ethyl acetate (2×20 mL). The combined ethyl acetate layers were washed with water (10 mL) and brine (10 mL), dried over anhydrous Na$_2$SO$_4$, and the solvent was removed to afford the crude product. This material was purified by column chromatography (100-200 mesh silica gel) using 10% MeOH in chloroform as the eluent to afford Compound (24) (190 mg, 30%) as a pale yellow solid. $^1$H NMR (DMSO-d$_6$): δ 11.75 (bs, 1H), 9.01 (s, 1H), 8.30 (s, 1H), 7.92 (m, 1H), 7.54 (s, 1H), 7.26 (d, J=8.70 Hz 1H), 6.71 (m, 1H), 4.47 (d, J=5.39 Hz; 1H), 3.89 (s, 2H), 3.38 (s, 3H). Mass (M+H): 263.0. IR (cm$^{-1}$): 3259, 2930, 1661, 1614, 1215, 1122, 924. HPLC purity (%): 93.7 (Max plot), 96.40 (254 nm), 94.59 (215 nm).

Synthesis of Compound (25)

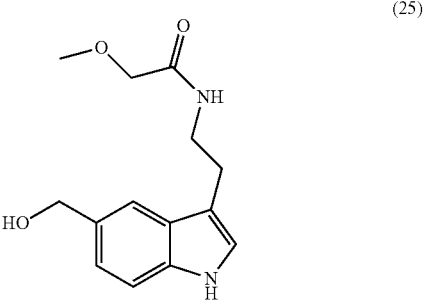 [SMILES: COCC(=O)NCCc1c[nH]c2ccc(CO)cc12]

Compound (25) can be synthesized according to the procedure shown in Scheme 18. The aniline starting material can be transformed to the corresponding arylhydrazine. Treatment of this arylhydrazine intermediate with 4-chlorobutyraldehyde diethyl acetal can afford the requisite indole intermediate. N-acylation followed by reduction of the C5 ester can result in the desired Compound (25).

Scheme 18

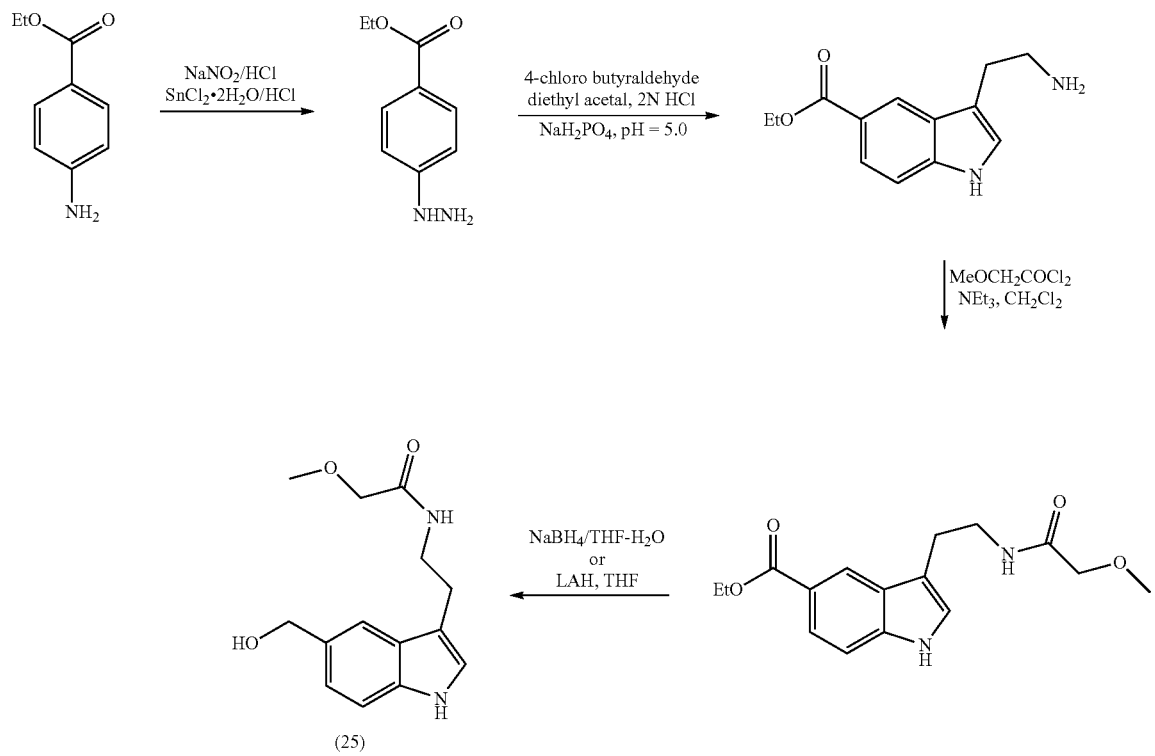

Synthesis of Formula (II) Compounds

Synthesis of Compound (26)

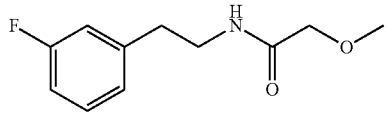
(26)

Compound (26) was synthesized according to the procedure shown in Scheme 19.

Scheme 19

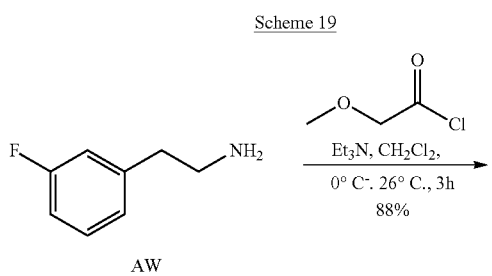

Na$_2$SO$_4$, and the solvent was removed to afford the crude product, which was purified by column chromatography (silica gel 100-200 mesh) using 2% MeOH in chloroform as the eluent to afford Compound (26) (380 mg, 88%) as a pale brown oil. $^1$H NMR (DMSO-d$_6$): δ 7.30-7.24 (m, 1H), 6.99-6.90 (m, 3H), 6.58 (bs, 1H), 3.87 (s, 2H), 3.55 (q, J=13.26 Hz; J=7.09 Hz; 2H), 3.36 (s, 3H), 2.84 (t, J=7.04, Hz; 2H). Mass (M+H): 212.0. IR (cm$^{-1}$): 3418, 2934, 1671, 1534, 1116, 783. HPLC purity (%): 97.37 (Max plot), 98.95 (215 nm).

Synthesis of Compound (27)

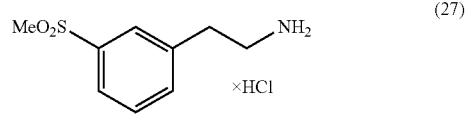 [SMILES: CS(=O)(=O)c1cccc(CCN)c1]
(27)

Compound (27) was prepared according to the procedure shown in Scheme 20.

Scheme 20

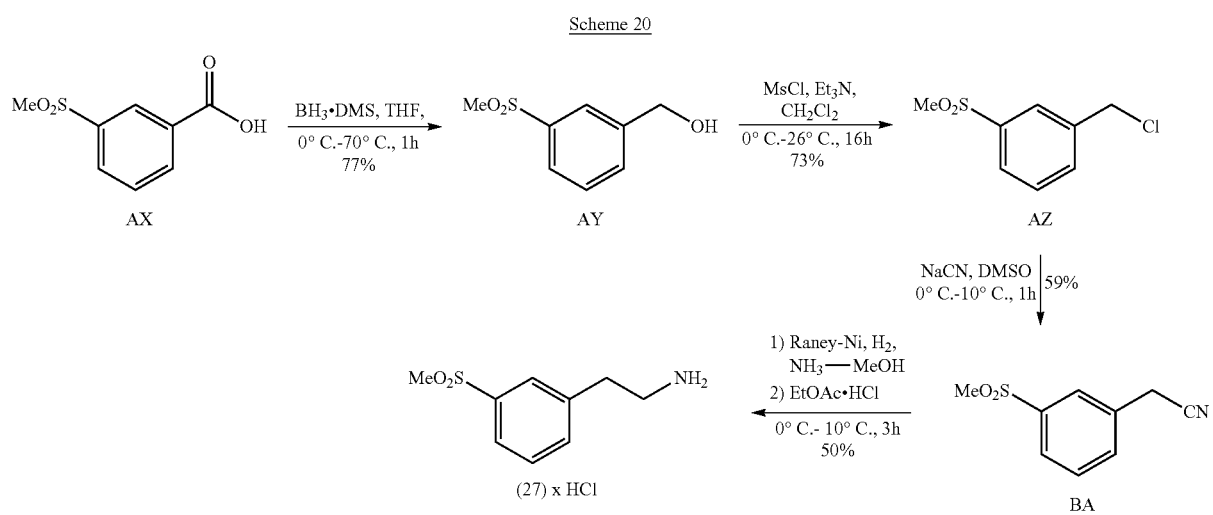

-continued

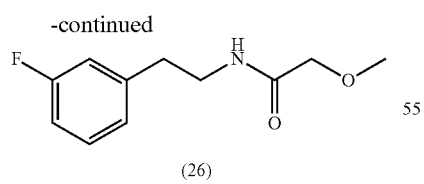
(26)

Preparation of Intermediate AY

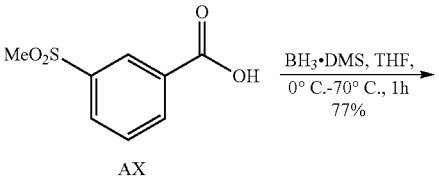

To a cold (0° C.) solution of Intermediate AW (250 mg, 1.79 mmol) and triethylamine (0.3 mL, 2.13 mmol) in dichloromethane (5.0 mL) was added slowly methoxyacetyl chloride (0.18 mL, 2.12 mmol) over 5 minutes. After the addition was complete, the reaction mixture was allowed to reach room temperature and stirred for 3 hours. The reaction mixture was diluted with dichloromethane (20 mL), washed with water (2×20 mL) and brine (20 mL), dried over anhydrous

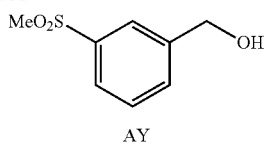

AY

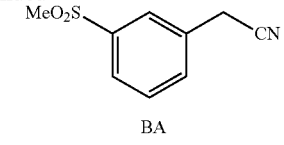

BA

To a solution of Intermediate AX (1.0 g, 4.99 mmol) in THF (20 mL) at 0° C. was added a solution of BH$_3$DMS (0.94 mL, 9.98 mmol). After the addition was complete, the reaction mixture was stirred at 70° C. for 1 hour. The reaction mixture was cooled, methanol (5.0 mL) was added, and the mixture was refluxed for 30 minutes. Solvent from the reaction mixture was removed via distillation, and the residue was diluted with ethyl acetate (30 mL), washed with water (2×15 mL) and brine (15 mL), dried over dried over anhydrous Na$_2$SO$_4$, and the solvent was removed to afford the crude Intermediate AY (720 mg, 77%) as an off white solid. This material was used in the next step without further purifications. $^1$H NMR (CDCl$_3$): δ 7.95 (s, 1H), 7.85 (d, J=7.88 Hz; 1H), 7.66 (d, J=7.88 Hz, 1H), 7.56 (t, J=7.65 Hz; 1H), 4.80 (s, 2H), 3.06 (s, 3H). Mass (M+H): 187.0.

Preparation of Intermediate AZ

To a cold solution of Intermediate AZ (500 mg, 2.45 mmol) in DMSO (5.0 mL) at 0° C. was added sodium cyanide (240 mg, 4.89 mmol) portionwise over 15 minutes. After the addition was complete, the reaction mixture was allowed and stirred at 10° C. for 1 hour. Ice cold water (20 mL) was added to the reaction mixture. The reaction was then extracted with ethyl acetate (3×20 mL), washed with water (20 mL) and brine (15 mL), dried over anhydrous Na$_2$SO$_4$, and the solvent was removed to afford the crude Intermediate BA. This material was purified by column chromatography (silica gel 100-200 mesh) using 40% ethyl acetate in petroleum ether as the eluent to afford the product (280 mg, 59%) as a pale brown solid. $^1$H NMR (CDCl$_3$): δ 7.95-7.91 (m, 2H), 7.69-7.61 (m, 2H), 3.86 (s, 2H), 3.07 (s, 3H). Mass (M−H): 194.0. IR (cm$^{-1}$): 2927, 2249, 1300, 1144, 964, 761.

Preparation of Compound (27)

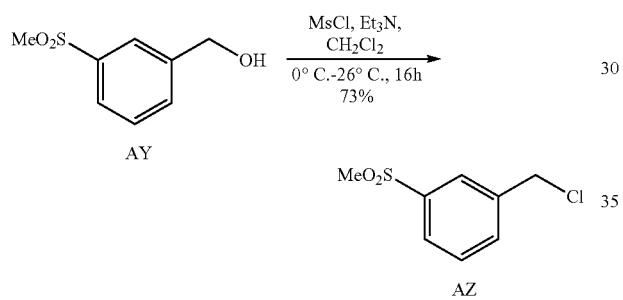

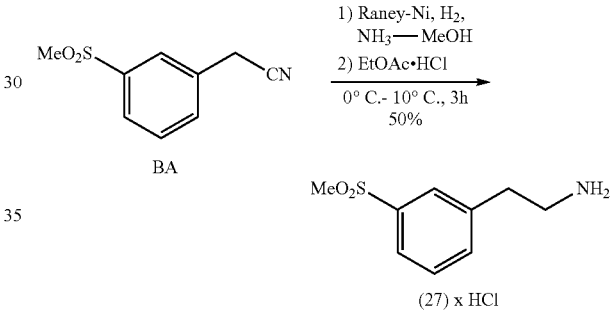

To a cold (0° C.) solution of Intermediate AY (2 g, 10.75 mmol) and triethylamine (2.26 mL, 16.12 mmol) in dichloromethane (25 mL) was added slowly methanesulfonyl chloride (1.08 mL, 13.85 mmol) over 5 minutes. After the addition was complete, the reaction mixture was allowed to reach room temperature and stirred for 16 hours. The reaction mixture was quenched with cold water (10 mL), diluted with dichloromethane (20 mL), washed with cold water (2×50 mL) and brine (20 mL), dried over anhydrous Na$_2$SO$_4$, and the solvent was removed to afford the crude Intermediate AZ. This material was purified by column chromatography (silica gel 100-200 mesh) using 10% ethyl acetate in petroleum ether as the eluent to afford the product (1.6 g, 73%) as a pale yellow oil. $^1$H NMR (CDCl$_3$): δ 7.98 (s, 1H), 7.91 (d, J=7.80 Hz; 1H), 7.70 (d, J=7.80 Hz, 1H), 7.59 (t, J=7.80 Hz; 1H), 4.65 (s, 2H), 3.07 (s, 3H). Mass (M+H): 205.0.

Preparation of Intermediate BA

A suspension of Intermediate BA (250 mg, 1.28 mmol) and Raney-Ni (100 mg, wet) in methanolic NH$_3$ (5.0 mL) was hydrogenated by bubbling H$_2$ at 10° C. for 3 hours. The reaction mixture was filtered, the cake was washed with methanol (3×10 mL), and the combined filtrate was concentrated under reduced pressure. The resulting oily residue was dissolved in ethyl acetate (2.0 mL), cooled in ice, treated with EtOAc and HCl, and stirred for 10 minutes. The resulting solid was filtered, washed with ethyl acetate (3×5 mL), and dried to afford Compound (27).HCl (150 mg, 50%) as an off white solid. $^1$H NMR (DMSO-d$_6$): δ 7.91 (bs, 2H), 7.83-7.81 (m, 2H), 7.64-7.62 (m, 2H), 3.21 (s, 3H), 3.11-3.01 (m, 2H), 2.99-2.97 (m, 2H). Mass (M+H): 200.0. IR (cm$^{-1}$): 3402, 3034, 1601, 1290, 1141, 965, 767, 532. HPLC purity (%): 99.92 (Max plot), 99.90 (215 nm).

Preparation of Compound (28)

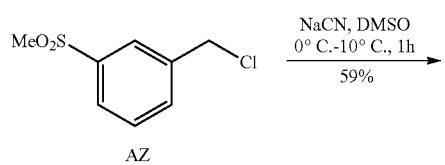

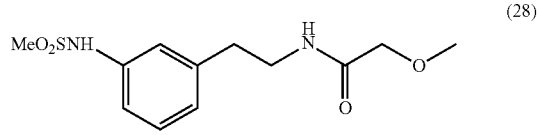

Compound (28) was prepared according to the procedure shown in Scheme 21.

Scheme 21

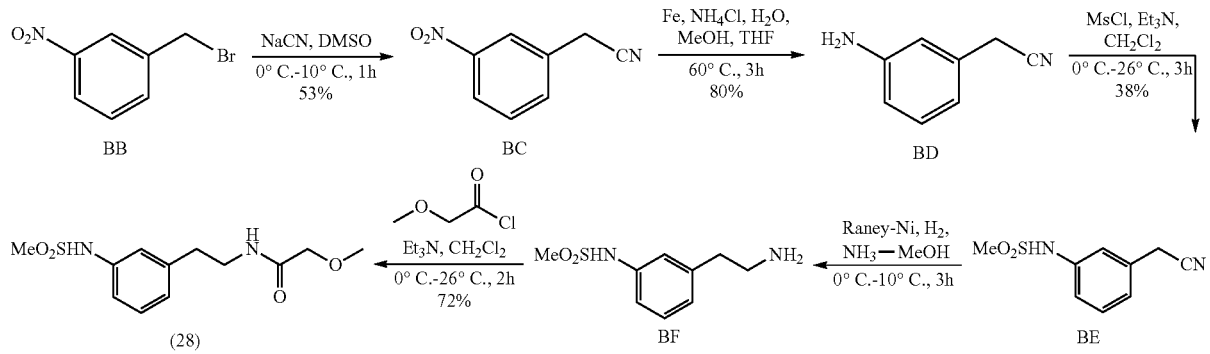

Preparation of Intermediate BC

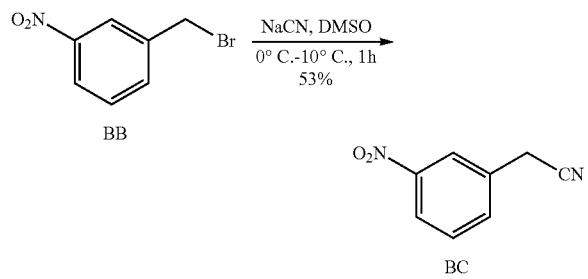

To a cold solution of Intermediate BB (2 g, 9.25 mmol) in DMSO (20.0 mL) at 0° C. was added sodium cyanide (900 mg, 18.36 mmol) portionwise over 15 minutes. After the addition was complete, the reaction mixture was allowed and stirred at 10° C. for 3 hours. Ice cold water was added to the reaction mixture (30 mL), and the reaction mixture was extracted with ethyl acetate (3×25 mL), washed with water (20 mL) and brine (15 mL), dried over dried over anhydrous $Na_2SO_4$, and the solvent was removed to afford the crude product. The mixture was purified by column chromatography (silica gel 100-200 mesh) using 40% ethyl acetate in petroleum ether as the eluent to afford Intermediate BC (800 mg, 53%) as a brown gum. $^1$H NMR ($CDCl_3$): δ 8.23-8.21 (m, 2H), 7.72 (d, J=7.80 Hz, 1H), 7.62 (m, 1H), 3.89 (s, 2H). Mass (M–H): 161.0.

Preparation of Intermediate BD

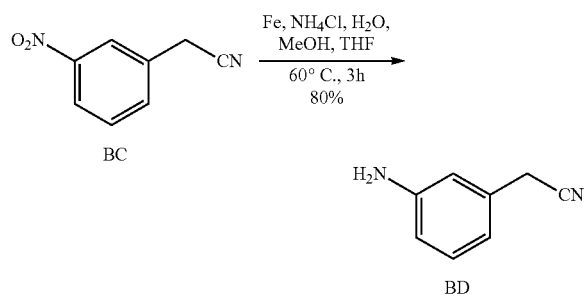

To a stirred solution of $NH_4Cl$ (1.1 g, 19.74 mmol) in $H_2O$ (16 mL) was added Fe powder (1.01 g, 18.08 mmol) followed by Intermediate BC (800 mg, 4.23 mmol) in a mixture of THF (8.0 mL) and MeOH (8.0 mL) slowly at room temperature. The reaction was then stirred for 3 h at 60° C. The reaction mixture was cooled to room temperature, diluted with ethyl acetate (100 mL), and filtered through a Celite bed. The organic layer was washed with water (2×25 mL) and brine solution (20 mL), dried over anhydrous $Na_2SO_4$, and evaporated to afford the crude product. This material was purified by column chromatography (silica gel 100-200 mesh) using 40% ethyl acetate in petroleum ether as the eluent to afford Intermediate BD (520 mg, 80%) as a brown gum. $^1$H NMR ($CDCl_3$): δ 7.14 (d, J=7.67 Hz, 1H), 7.68-6.62 (m, 3H), 3.74 (bs, 2H), 3.65 (s, 2H). Mass (M+H): 238.0.

Preparation of Intermediate BE

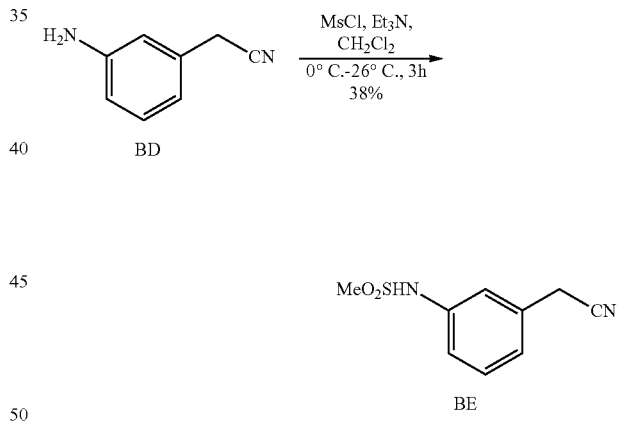

To a cold (0° C.) solution of Intermediate BD (500 mg, 3.78 mmol) and triethylamine (0.63 mL, 4.48 mmol) in dichloromethane (10 mL) was added slowly methanesulfonyl chloride (0.35 mL, 4.49 mmol) over 5 minutes. After the addition was complete, the reaction mixture was allowed to reach room temperature and stirred for 2 hours. The reaction mixture was diluted with dichloromethane (10 mL), washed with water (2×20 mL) and brine (10 mL), dried over anhydrous $Na_2SO_4$, and the solvent was removed to afford the crude product. This material was purified by column chromatography (silica gel 100-200 mesh) using 15% ethyl acetate in petroleum ether as the eluent to afford Intermediate BE (300 mg, 38%) as a brown gum. $^1$H NMR ($CDCl_3$): δ 7.40-7.34 (m, 1H), 7.20-7.16 (m, 2H), 6.63 (bs, 1H), 3.76 (s, 2H), 3.04 (s, 3H). Mass (M–H): 187.0.

Preparation of Intermediate BF

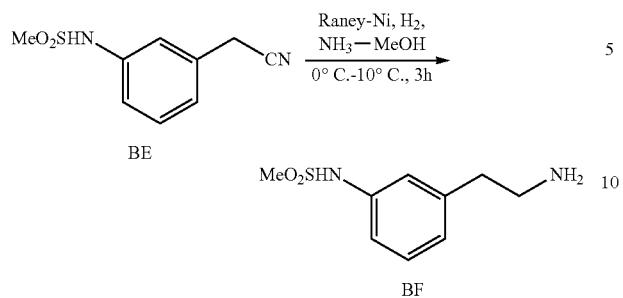

A suspension of Intermediate BE (100 mg, 0.47 mmol) and Raney-Ni (20 mg, wet) in methanolic $NH_3$ (5.0 mL) was hydrogenated by bubbling $H_2$ at 10° C. for 3 hours. The reaction mixture was filtered, and the cake was washed with methanol (3×10 mL). The combined filtrates were concentrated under reduced pressure to afford Intermediate BF (80 mg, crude) as a pale brown oil, which was used in the next step without further purification.

Preparation of Compound (28)

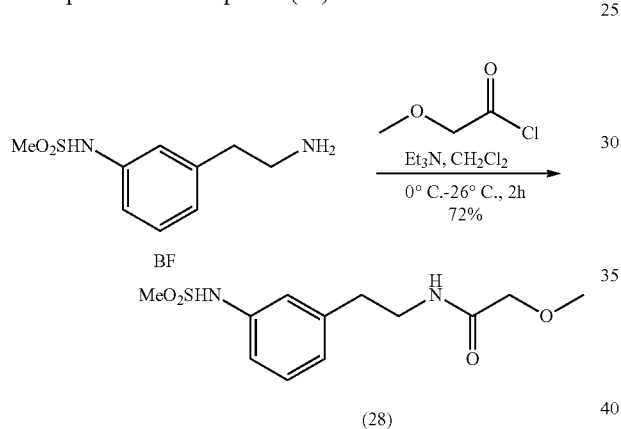

To a cold (0° C.) solution of crude Intermediate BF (30 mg, 0.14 mmol) and triethylamine (0.02 mL, 0.14 mmol) in dichloromethane (4.0 mL) was added slowly a solution of methoxyacetyl chloride (0.03 mL, 0.13 mmol) in dichloromethane (1.0 mL) over 5 minutes. After the addition was complete, the reaction mixture was allowed to reach room temperature and stirred for 2 hours. The reaction mixture was diluted with dichloromethane (10 mL), washed with water (2×10 mL) and brine (10 mL), dried over anhydrous $Na_2SO_4$, and the solvent was removed to afford the crude product. This material was purified by column chromatography (silica gel 100-200 mesh) using 23% ethyl acetate in petroleum ether as the eluent to afford Compound (28) (29 mg, 72%) as a pale brown gum. $^1H$ NMR ($CDCl_3$): δ 7.31-7.25 (m, 2H), 7.09-7.03 (m, 2H), 6.58 (bs, 1H), 6.50 (bs, 1H), 3.87 (s, 2H), 3.59-3.53 (q, 2H), 3.37 (s, 3H), 2.84 (t, J=7.11 Hz; 2H). Mass (M+H): 286.9. IR ($cm^{-1}$): 3401, 2927, 1655, 1328, 1149, 976, 763, 515. HPLC purity (%): 94.51 (Max plot), 92.11 (215 nm).

Synthesis of Compounds (29) and (30)

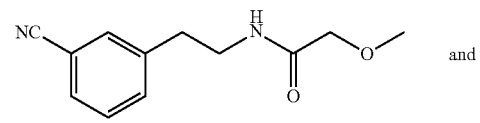

(29)

and

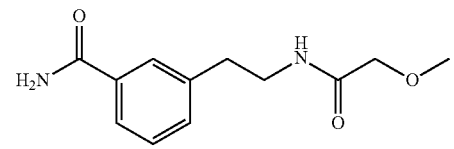

(30)

Compounds (29) and (30) were prepared according to the procedure in Scheme 22.

Scheme 22

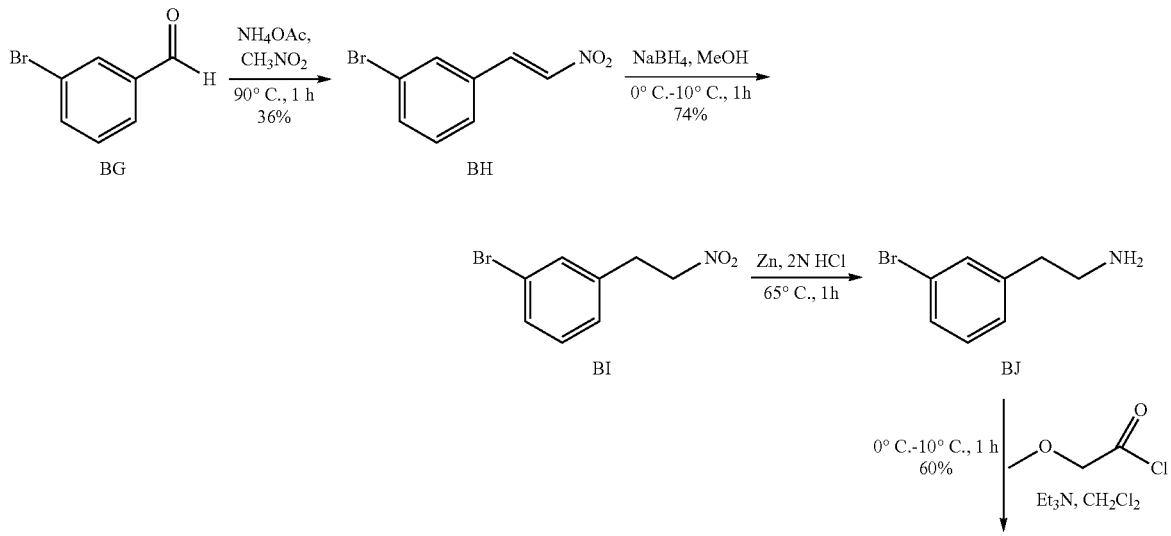

-continued

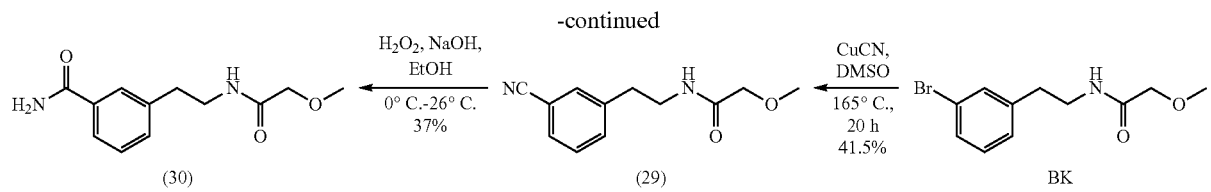

Preparation of Intermediate BH

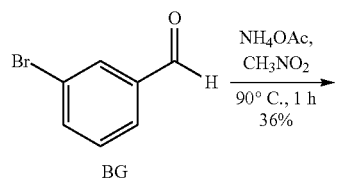

A suspension of Intermediate BG (5 g, 27.02 mmol) and ammonium acetate (4.57 g, 59.45 mmol) in nitromethane (150.0 mL) was stirred at 90° C. for 1 hour. The reaction mixture was concentrated under reduced pressure, and the resulting crude material was dissolved in ethyl acetate (100 mL), washed with water (2×30 mL) and brine solution (25 mL), dried over anhydrous $Na_2SO_4$, and the solvent was removed to afford the crude product. This material was purified by column chromatography (silica gel 100-200 mesh) using 2% ethyl acetate in petroleum ether as the eluent to afford Intermediate BH (2.2 g, 36%) as a yellow solid. $^1H$ NMR ($CDCl_3$): δ 7.93 (d, J=13.66 Hz, 1H), 7.70 (s, 1H), 7.62 (d, J=8.00 Hz, 1H), 7.56 (d, J=13.66 Hz, 1H), 7.48 (d, J=7.61 Hz, 1H), 7.34 (s, J=7.90 Hz, 1H). Mass (M−2H), M: 226.9, 228.9.

Preparation of Intermediate BI

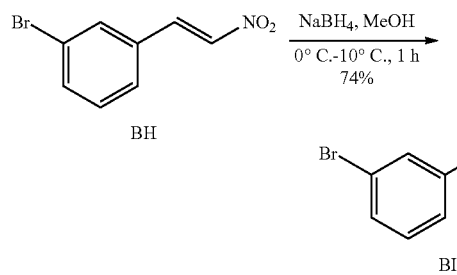

To a cold (0° C.) solution of Intermediate BH (2 g, 8.77 mmol) in methanol (30 mL) at 0° C. was added $NaBH_4$ (0.4 g, 10.52 mmol) portionwise over 15 minutes. After the addition was complete, the reaction mixture was allowed to stir at 10° C. for 1 hour. The reaction mixture was quenched with water (10 mL) and concentrated under reduced pressure. The resulting aqueous residue was diluted with water (25 mL) and extracted with ethyl acetate (2×50 mL). The combined ethyl acetate layers were washed with water (30 mL) and brine solution (25 mL), dried over anhydrous $Na_2SO_4$, and the solvent was removed to afford the crude product. This material was purified by column chromatography (silica gel 100-200 mesh) using 5% ethyl acetate in petroleum ether as the eluent to afford Intermediate BI (1.5 g, 74%) as pale yellow solid. $^1H$ NMR ($CDCl_3$): δ 7.39 (d, J=10.78 Hz, 1H), 7.37 (s, 1H), 7.22-7.15 (m, 2H), 4.61 (t, J=7.46 Hz, 2H), 3.29 (t, J=7.03 Hz, 2H). Mass (M−2H), M: 227.9, 229.9.

Preparation of Intermediate BJ

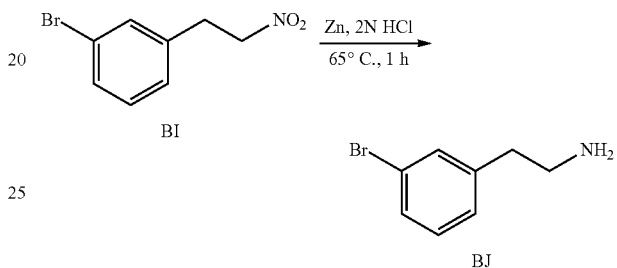

A suspension of Intermediate BI (350 mg, 15.21 mmol) and zinc powder (300 mg, 4.56 mmol) in methanol (50.0 mL) and 2N HCl (50.0 mL) was stirred at 65° C. for 1 hour. The reaction mixture was filtered, and the cake was washed with methanol (3×10 mL). The combined filtrates were concentrated under reduced pressure, and the residue was dissolved in dichloromethane, dried over anhydrous $Na_2SO_4$, and the solvent was removed to afford the crude Intermediate BJ (1 g, crude), which was used in the next step without further purification.

Preparation of Intermediate BK

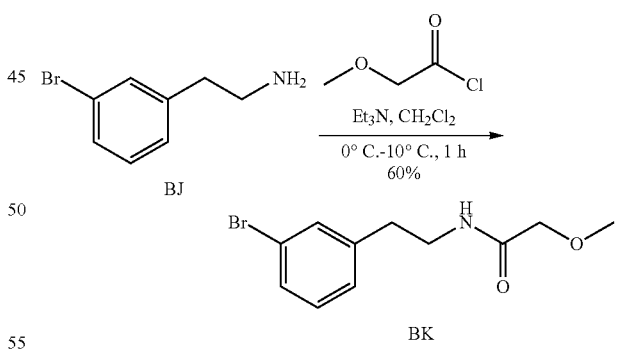

To a cold (0° C.) solution of crude Intermediate BJ (300 mg, 1.50 mmol) and triethylamine (0.42 mL, 3.01 mmol) in dichloromethane (15.0 mL) was added slowly a solution of methoxyacetyl chloride (0.15 mL, 1.65 mmol) in dichloromethane (2.0 mL) over 5 minutes. After the addition was complete, the reaction mixture was allowed to reach room temperature and stirred for 2 hours. The reaction mixture was diluted with dichloromethane (10 mL), washed with water (2×20 mL) and brine (10 mL), dried over anhydrous $Na_2SO_4$, and the solvent was removed to afford the crude product. This material was purified by column chromatography (silica gel 100-200 mesh) using 1% MeOH in chloroform as the eluent to afford Intermediate BK (200 mg, 60%) as a pale brown solid. $^1$H NMR (CDCl$_3$): δ 7.38-7.36 (m, 2H), 7.20-7.12 (m, 2H), 6.55 (bs, 1H), 3.87 (s, 2H), 3.56-3.51 (m, 2H), 3.37 (s, 3H), 2.81 (t, J=7.12 Hz, 2H). Mass (M, M+H): 271.9, 273.9.

Preparation of Compound (29)

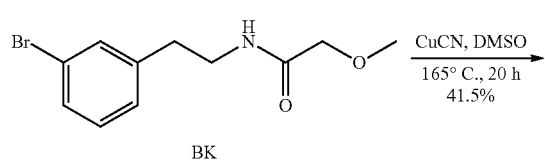

A suspension of Intermediate BK (300 mg, 1.10 mmol) and CuCN (200 mg, 2.20 mmol) in DMSO (4.0 mL) was stirred in a sealed tube at 165° C. for 20 hours. The reaction mixture was cooled to room temperature, diluted with water (10 mL), and extracted with ethyl acetate (2×20 mL). The combined ethyl acetate layers were washed with water (2×10 mL) and brine (10 mL), dried over anhydrous Na$_2$SO$_4$, and the solvent was removed to afford the crude product. This material was purified by column chromatography (silica gel 100-200 mesh) using 2% MeOH in chloroform as the eluent to afford Compound (29) (100 mg, 41.5%) as a pale brown gum. $^1$H NMR (CDCl$_3$): δ 7.55-7.42 (m, 4H), 6.6 (bs, 1H), 3.88 (s, 2H), 3.58-3.53 (q, 2H), 3.38 (s, 3H), 2.89 (t, J=7.31 Hz; 2H). Mass (M−H): 217. IR (cm$^{-1}$): 3412, 2928, 2230, 1665, 1537, 1116, 798, 691. HPLC purity (%): 95.33 (Max plot), 92.55 (215 nm).

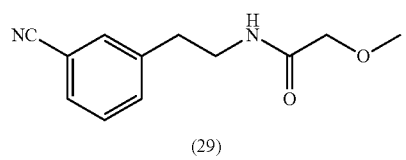

Preparation of Compound (30)

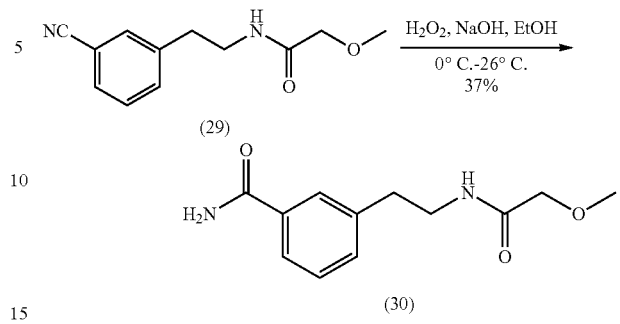

To a cold (0° C.) solution of Compound (29) (100 mg, 0.45 mmol), 3N NaOH (3.0 mL) in ethanol (3.0 mL) at 0° C. was added added H$_2$O$_2$ (30% in water; 0.05 mL). After the addition was complete, the reaction mixture was allowed to reach room temperature and stirred for 20 hours. The reaction mixture was concentrated, and the resulting aqueous residue was diluted with dichloromethane (50 mL), washed with water (2×10 mL) and brine (10 mL), dried over anhydrous Na$_2$SO$_4$, and the solvent was removed to afford the crude product. This material was purified by column chromatography (silica gel 100-200 mesh) using 5% MeOH in chloroform as the eluent to afford Compound (30) (40 mg, 37%) as an off white solid. $^1$H NMR (CDCl$_3$): δ 7.70-7.67 (m, 2H), 7.40-7.38 (m, 2H), 6.58 (bs, 1H), 6.2 (bs, 1H), 5.6 (bs, 1H), 3.86 (s, 2H), 3.63-3.60 (q, 2H), 3.58 (s, 3H), 2.91 (t, J=7.04 Hz; 2H). Mass (M+H): 237.1. IR (cm$^{-1}$): 3339, 3162, 1661, 1543, 1199, 1120, 690. HPLC purity (%): 95.95 (Max plot), 95.29 (215 nm).

Preparation of Compound (31)

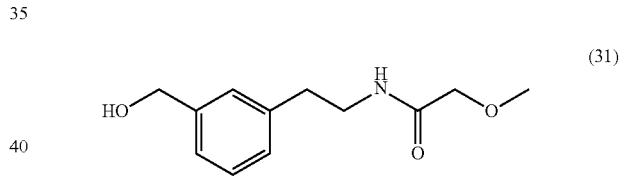

Compound (31) was prepared according to the procedure shown in Scheme 23.

Scheme 23

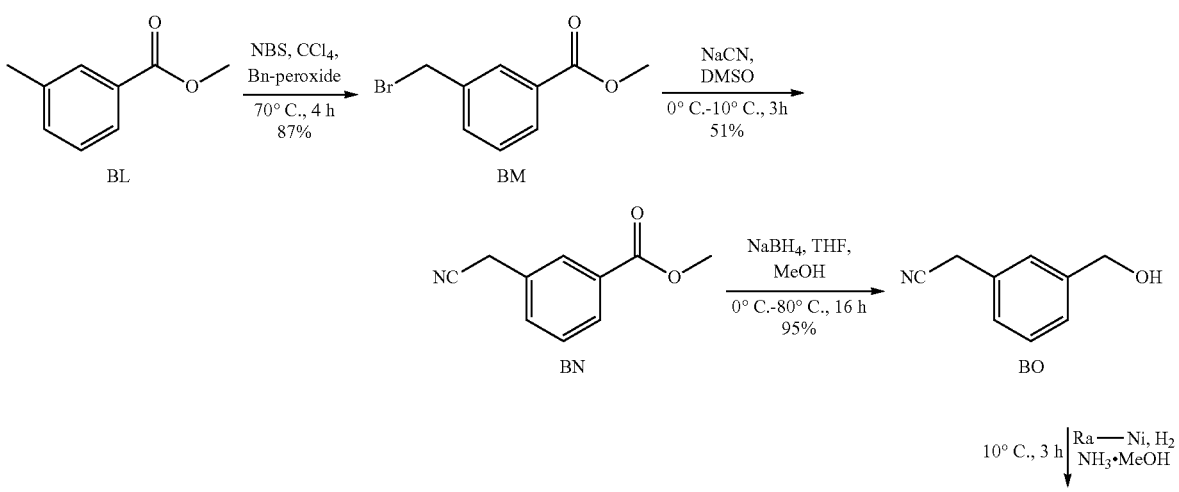

-continued

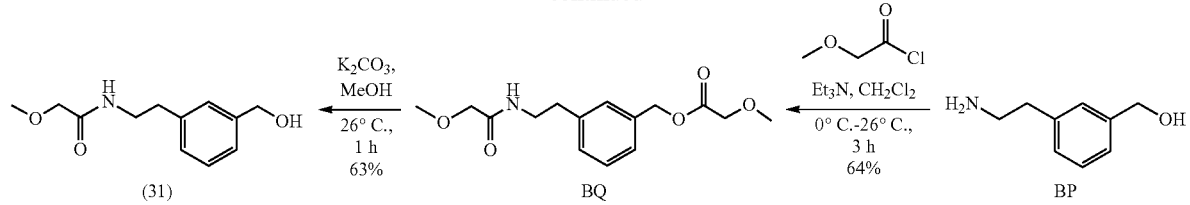

Preparation of Intermediate BM

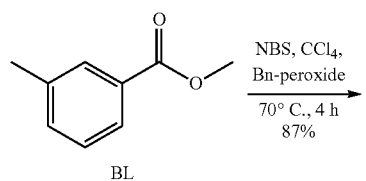

To a solution of Intermediate BL (5.0 g, 33.29 mmol) and benzoyl peroxide (0.4 g, L66 mmol) in $CCl_4$ (60.0 mL) was added NBS (5.75 g, 33.29 mmol). The reaction mixture was stirred at 70° C. for 4 hours. The reaction mixture was filtered, and the filtrate was concentrated to obtain the crude product. This material was purified by column chromatography (silica gel 100-200 mesh) using 1% ethyl acetate in petroleum ether as the eluent to afford Intermediate BM (6.8 g, 87%) as pale yellow oil. $^1$H NMR ($CDCl_3$): δ 8.07 (s, 1H), 8.00-7.96 (m, 1H), 7.60-7.58 (m, 1H), 7.43 (t, J=7.67 Hz, 1H), 4.52 (s, 2H), 3.93 (s, 31-1).

Preparation of Intermediate BN

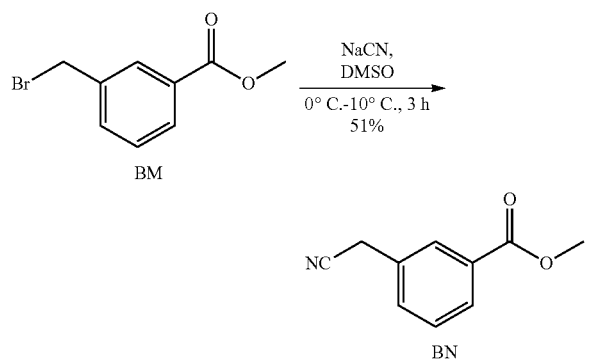

To a cold solution of Intermediate BM (7.2 g, 31.44 mmol) in DMSO (35.0 mL) at 0° C. was added a sodium cyanide (3.0 g, 62.88 mmol) portionwise over 15 minutes. After the addition was complete, the reaction mixture was allowed to stir at 10° C. for 3 hours. Ice cold water was added to the reaction mixture (50 mL), and the reaction was extracted with ethyl acetate (3×50 mL), washed with water (2×25 mL) and brine (25 mL), dried anhydrous $Na_2SO_4$, and the solvent was removed to afford the crude product. This material was puri- fied by column chromatography (silica gel 100-200 mesh) using 10% ethyl acetate in petroleum ether as the eluent to afford Intermediate BN (2.8 g, 51%) as a pale brown liquid. $^1$H NMR ($CDCl_3$): δ 9.44-9.42 (m, 2H), 8.90-8.78 (m, 2H), 4.63 (s, 3H), 4.49 (s, 2H). Mass (M–H): 174.1.

Preparation of Intermediate BO

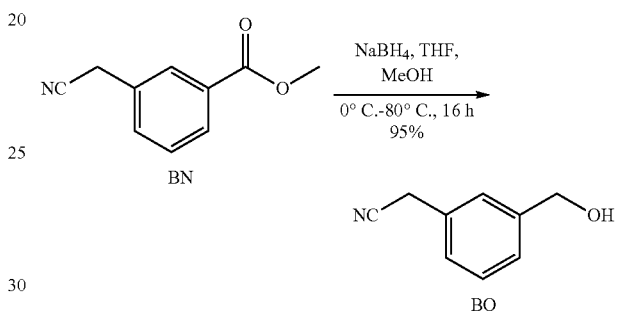

To a cold (0° C.) solution of Intermediate BN (500 mg, 2.85 mmol) in THF (25.0 mL) was added $NaBH_4$ (216 mg, 5.71 mmol), and the reaction stirred at 80° C. for 15 minutes. Methanol (8.0 mL) was then added to the reaction mixture at 80° C. until the effervescence eased. The reaction was then stirred for approximately 16 hours. The reaction mixture was then quenched with water (10 mL) and concentrated under reduced pressure. The resulting aqueous residue was diluted with water (25 mL) and extracted with ethyl acetate (2×50 mL). The combined ethyl acetate layers were washed with water (25 mL) and brine solution (25 mL), dried over anhydrous $Na_2SO_4$, and the solvent was removed to afford the crude product. This material was purified by column chromatography (silica gel 100-200 mesh) using 12% ethyl acetate in petroleum ether as the eluent to afford Intermediate BO (410 mg, 95%) as as pale yellow oil. $^1$H NMR ($CDCl_3$): δ 7.40-7.32 (m, 3H), 7.27 (s, 1H), 4.72 (d, J=5.66 Hz, 2H), 3.76 (s, 2H), 1.72 (t, J=5.76 Hz, 1H). Mass (M–H): 146.1.

Preparation of Intermediate BP

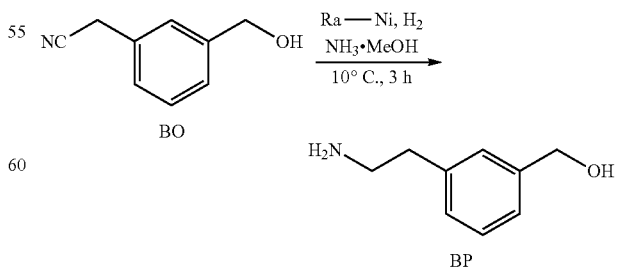

A suspension of Intermediate BO (200 mg, 1.32 mmol) and Raney-Ni (50 mg, wet) in methanolic $NH_3$ (6.0 mL) was hydrogenated by bubbling H₂ at 10° C. for 3 hours. The reaction mixture was filtered, and the cake was washed with methanol (3×10 mL). The combined filtrates were concentrated under reduced pressure to afford Intermediate BP (200 mg, crude), as a pale brown gum. $^1$H NMR (CDCl₃): δ 7.30-7.21 (m, 4H), 4.69 (s, 2H), 3.49 (s, 2H), 2.9 (bs, 2H), 4.80 (s, 2H). Mass (M+H): 152.0.

Preparation of Intermediate BQ

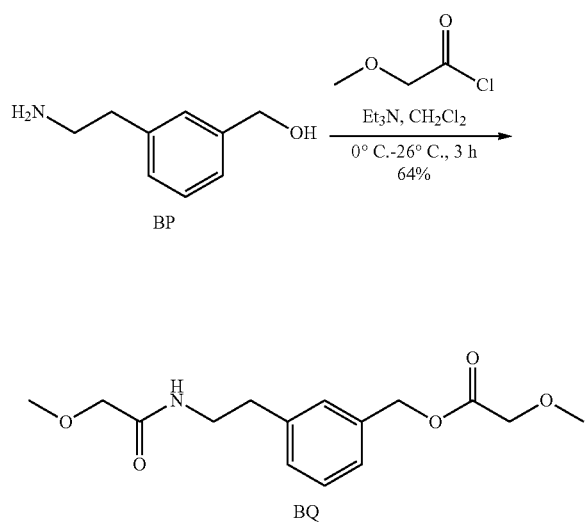

To a cold (0° C.) solution of Intermediate BP (200 mg, 1.32 mmol) and triethylamine (0.27 mL, 1.92 mmol) in dichloromethane (10.0 mL) was added slowly methoxyacetyl chloride (0.18 mL, 1.96 mmol) over 5 minutes. After the addition was complete, the reaction mixture was allowed to reach room temperature and stirred for 3 hours. The reaction mixture was diluted with dichloromethane (10 mL), washed with water (2×20 mL) and brine (10 mL), dried over anhydrous Na₂SO₄, and the solvent was removed to afford the crude product. This material was purified by column chromatography (silica gel 100-200 mesh) using 5-10% ethyl acetate in petroleum ether as the eluent to afford Intermediate BQ (250 mg, 64%) as a pale brown gum. $^1$H NMR (CDCl₃): δ 7.33-7.17 (m, 4H), 6.56 (bs, 1H), 5.18 (s, 2H), 4.08 (s, 2H), 3.87 (s, 2H), 3.58-3.53 (m, 2H), 3.46 (s, 3H), 3.36 (s, 3H), 2.85 (t, J=7.07 Hz; 2H). Mass (M+H): 295.9.

Preparation of Compound (31)

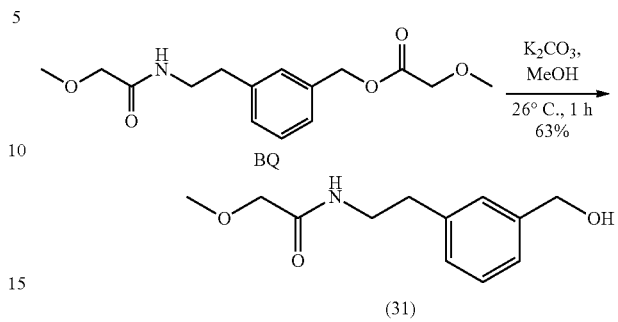

A suspension of Intermediate BQ (250 mg, 0.84 mmol) and K₂CO₃ (130 mg, 0.94 mmol) in methanol (3.0 mL) was stirred at 26° C. for 1 hour. The reaction mixture was concentrated under reduced pressure; the residue was then diluted with water (20 mL) and extracted with ethyl acetate (2×20 mL). The combined ethyl acetate layers were washed with water (10 mL) and brine (10 mL), dried over anhydrous Na₂SO₄, and the solvent was removed to afford the crude product. This material was purified by column chromatography (100-200 mesh silica gel) using 20% ethyl acetate in petroleum ether as the eluent to afford Compound (31) (120 mg, 63%) as a pale brown solid. $^1$H NMR (CDCl₃): δ 7.32-7.22 (m, 3H), 7.13 (d, J=7.41 Hz; 1H), 6.56 (bs, 1H), 4.67 (s, 2H), 3.85 (s, 2H), 3.58-3.53 (m, 3H), 3.35 (s, 3H), 2.84 (t, J=7.12 Hz; 2H). Mass (M+H): 223.9. IR (cm$^{-1}$): 3401, 2931, 1658, 1540, 1116, 791. HPLC purity (%): 98.9 (Max plot), 96.92 (254 nm), 97.11 (215 nm).

Synthesis of Compound (32)

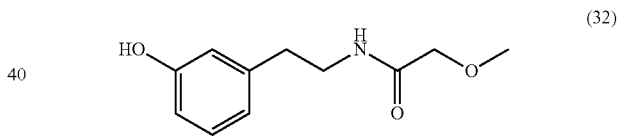

Compound (32) was synthesized according to the procedure shown in Scheme 24.

Scheme 24

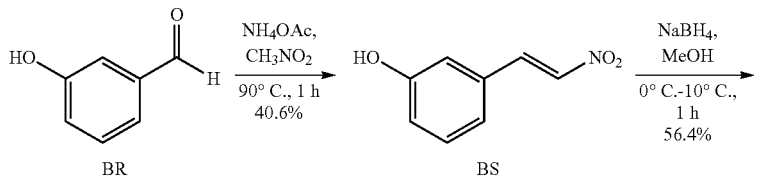

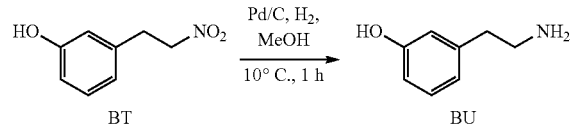

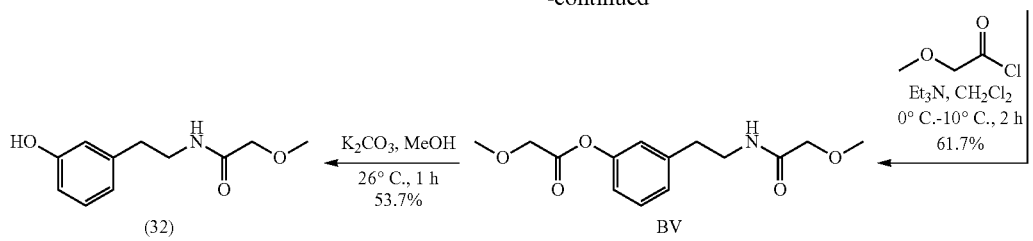

Preparation of Intermediate BS

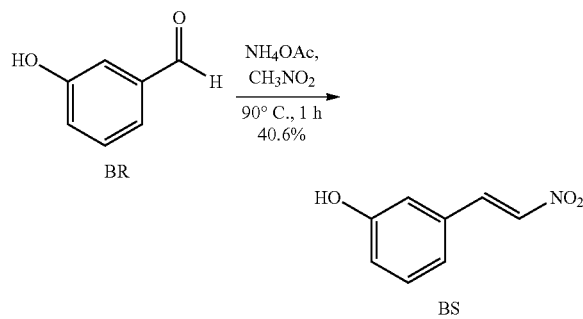

A suspension of Intermediate BR (1 g, 8.19 mmol) and ammonium acetate (1.38 g, 18.03 mmol) in nitromethane (70.0 mL) was stirred at 90° C. for 1 hour. The reaction mixture was concentrated under reduced pressure, the resulting crude material was dissolved in ethyl acetate (50 mL), washed with water (2×20 mL) and brine solution (25 mL), dried over anhydrous $Na_2SO_4$, and the solvent was removed to afford the crude product. This material was purified by column chromatography (silica gel 100-200 mesh) using 10% ethyl acetate in petroleum ether as the eluent to afford Intermediate BS (550 mg, 40.6%) as yellow solid. $^1$H NMR (CDCl$_3$): δ 7.95 (d, J=13.68 Hz; 1H), 7.55 (d, J=13.68 Hz; 1H), 7.13 (d, J=7.87 Hz, 1H), 7.01-6.95 (m, 2H), 4.97 (s, 2H). Mass (M−H): 164.0.

Preparation of Intermediate BT

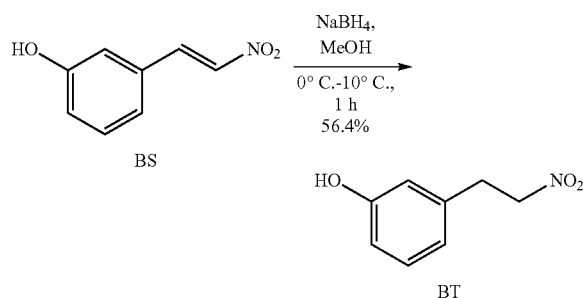

To a cold (0° C.) solution of Intermediate BS (350 mg, 2.12 mmol) in methanol (3.5 mL) at 0° C. was added portionwise NaBH$_4$ (100 mg, 2.54 mmol) over 5 minutes. After the addition was complete, the reaction mixture was allowed to stir at 10° C. for 1 hour. The reaction mixture was quenched with water (5 mL) and concentrated under reduced pressure. The resulting aqueous residue was diluted with water (15 mL) and extracted with ethyl acetate (2×20 mL). The combined ethyl acetate layers were washed with water (10 mL) and brine solution (15 mL), dried over anhydrous Na$_2$SO$_4$, and the solvent was removed to afford the crude product. This material was purified by column chromatography (silica gel 100-200 mesh) using 10% ethyl acetate in petroleum ether as the eluent to afford Intermediate BT (200 mg, 56.4%) as a pale yellow solid. $^1$H NMR (CDCl$_3$): δ 7.19 (s, J=7.90 Hz; 1H), 6.77-6.72 (m, 2H), 6.68 (s, 1H), 4.59 (t, J=7.32 Hz, 2H), 3.27 (t, J=7.32 Hz). Mass (M−H): 166.0.

Preparation of Intermediate BU

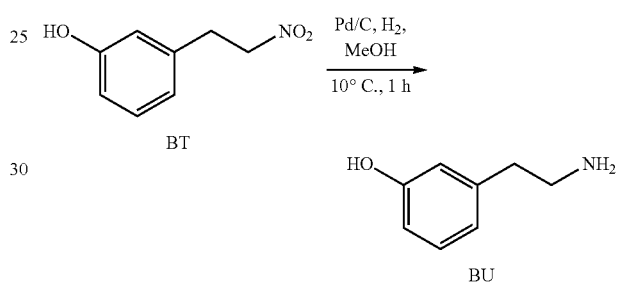

A suspension of Intermediate BT (150 mg, 0.89 mmol) and 10% Pd/C (25 mg, dry) in MeOH (1.0 mL) was hydrogenated by bubbling H$_2$ at 10° C. for 3 hours. The reaction mixture was filtered, and the cake was washed with methanol (3×5 mL). The combined filtrates were concentrated under reduced pressure. The obtained gummy material was dissolved in ethyl acetate (1 mL), treated with EtOAc and HCl (0.5 mL). The reaction stirred for 10 minutes and was then concentrated to afford the HCl salt of Intermediate BU (200 mg, crude) as a pale brown gum. This material was used without further purification in the next step.

Preparation of Intermediate BV

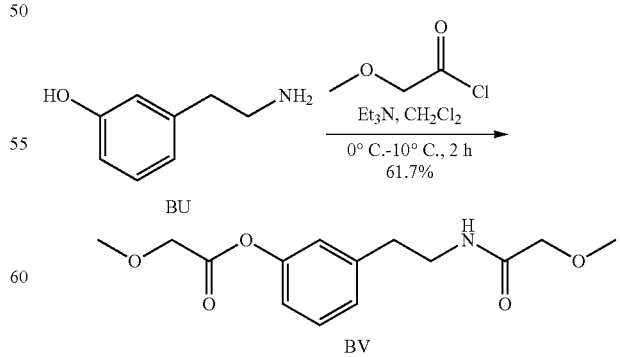

To a cold (0° C.) solution of Intermediate BU (200 mg, 1.15 mmol) and triethylamine (0.323 mL, 2.3 mmol) in dichloromethane (3.0 mL) was added slowly methoxyacetyl chloride (0.136 mL, 1.26 mmol) over 5 minutes. After the addition was complete, the reaction mixture was allowed to reach room temperature and stirred for 2 hours. The reaction mixture was diluted with dichloromethane (10 mL), washed with water (2×20 mL) and brine (10 mL), dried over anhydrous Na$_2$SO$_4$, and the solvent was removed to afford the crude product. This material was purified by column chromatography (silica gel 100-200 mesh) using 2% MeOH in chloroform as the eluent to afford Intermediate BV (20 mg, 61.7%) as a pale brown gum. $^1$H NMR (CDCl$_3$): δ 7.33 (t, J=7.86 Hz; 1H), 7.09 (d, J=7.64 Hz; 1H), 7.00-6.97 (m, 2H), 6.56 (bs, 1H), 4.28 (s, 2H), 3.87 (s, 2H), 3.59-3.54 (m, 5H), 3.35 (s, 3H), 2.85 (t, J=7.04 Hz; 2H). Mass (M+H): 282.0.

Preparation of Compound (32)

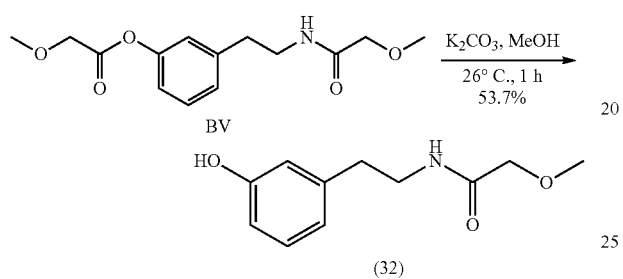

(32)

A suspension of Intermediate BV (200 mg, 0.71 mmol) and K$_2$CO$_3$ (108 mg, 0.78 mmol) in methanol (2.0 mL) was stirred at 26° C. for 1 hour. The reaction mixture was concentrated under reduced pressure; the residue was then diluted with water (10 mL) and extracted with ethyl acetate (2×20 mL). The combined ethyl acetate layers were washed with water (10 mL) and brine (10 mL), dried over anhydrous Na$_2$SO$_4$, and the solvent was removed to afford the crude product. This material was purified by column chromatography (100-200 mesh silica gel) using 4% MeOH in chloroform as the eluent to afford Compound (32) (80 mg, 53.7%) as a pale brown gum. $^1$H NMR (CDCl$_3$): δ 7.17 (t, J=8.30 Hz; 1H), 6.77 (d, J=7.81 Hz; 1H), 6.71-6.69 (m, 2H), 6.55 (bs, 1H), 4.85 (s, 1H), 3.87 (s, 2H), 3.58-3.53 (m, 3H), 3.35 (s, 3H), 2.79 (t, J=7.08 Hz; 2H). Mass (M+H): 210.0. IR (cm$^{-1}$): 3392, 2936, 1658, 1542, 1455, 1116, 783. HPLC purity (%): 94.43 (Max plot), 94.16 (215 nm).

Synthesis of Compounds (33), (34), and (35)

(33)

(34)

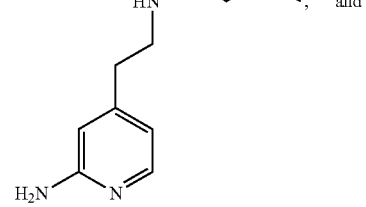
, and

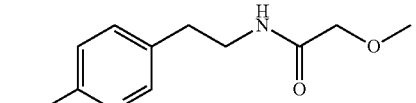

(35)

Compounds (33)-(35) were synthesized according to the procedure shown in Scheme 25.

Scheme 25

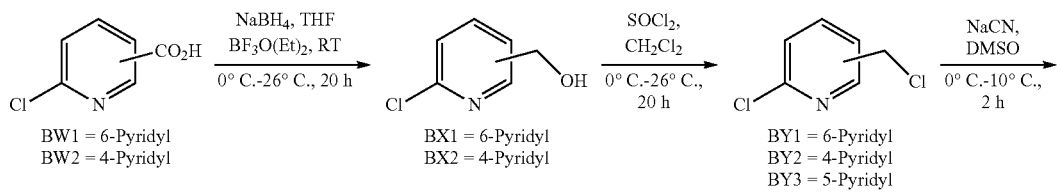

BW1 = 6-Pyridyl
BW2 = 4-Pyridyl

BX1 = 6-Pyridyl
BX2 = 4-Pyridyl

BY1 = 6-Pyridyl
BY2 = 4-Pyridyl
BY3 = 5-Pyridyl

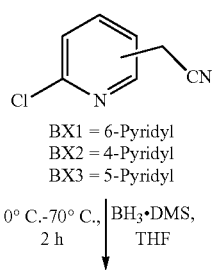

BX1 = 6-Pyridyl
BX2 = 4-Pyridyl
BX3 = 5-Pyridyl

0° C.-70° C., 2 h | BH$_3$·DMS, THF

-continued

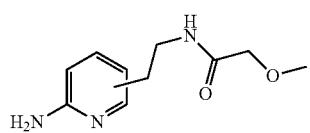 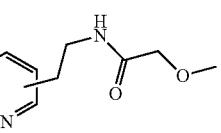 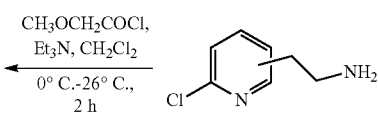

1) $(C_6H_5)_2CNH$, NaOtBu, $Pd_2(dba)_3$, BINAP, Toluene, 80° C., 6 h
2) $NH_2OH$, RT, 3 h $CH_3OCH_2COCl$, $Et_3N$, $CH_2Cl_2$
0° C.-26° C., 2 h Compound (33) R = 6-Pyridyl
Compound (34) R = 4-Pyridyl
Compound (35) R = 5-Pyridyl BZ1 = 6-Pyridyl
BZ2 = 4-Pyridyl
BZ3 = 5-Pyridyl BY1 = 6-Pyridyl
BY2 = 4-Pyridyl
BY3 = 5-Pyridyl Preparation of Intermediate BX

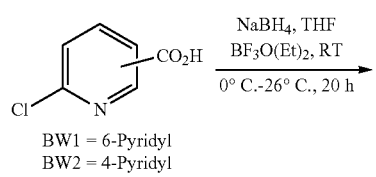

$NaBH_4$, THF
$BF_3O(Et)_2$, RT
0° C.-26° C., 20 h

BW1 = 6-Pyridyl
BW2 = 4-Pyridyl

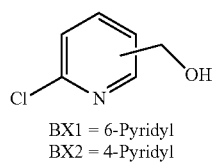

BX1 = 6-Pyridyl
BX2 = 4-Pyridyl

To a cold suspension of $NaBH_4$ (1.5 mmol) in THF (30 mL) at 0° C., Intermediate BW (1.0 mmol) was added portionwise over 15 minutes. After the addition was complete, the reaction mixture was allowed to stir at room temperature for 2 hours. To the reaction mixture was added slowly a solution of $BF_3.O(Et)_2$ (2.0 mmol) in THF (10 mL) over 3 hours. After the addition was complete, the reaction mixture was stirred at room temperature for 20 hours. The reaction mixture was quenched with 1.5N HCl (10 mL) and MeOH (20 mL) then concentrated. The obtained aqueous residue was basified (pH~10) with 1N NaOH solution and extracted with ethyl acetate (3×30 mL). The combined ethyl acetate layers were washed with brine solution (2×20 mL), dried over anhydrous $Na_2SO_4$, and the solvent was removed to afford the crude Intermediate BX (Table 17), which was used in the next step without further purification.

TABLE 17

| BX1 | 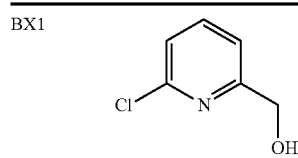 | Intermediate BW1 (1.5 g, 9.52 mmol) was reacted with $NaBH_4$ (1.08 g, 28.57 mmol) and $BF_3\cdot O(Et)_2$ (4.8 mL, 38.09 mmol) in THF (100 mL) to give Intermediate BX1 (1.3 g, crude) as a colorless thick oil. $^1H$ NMR ($CDCl_3$): δ 7.66 (t, J = 7.67 Hz; 1H). 7.25 (d, J = 7.87 Hz; 2H), 4.75 (s, 2H), 3.41 (bs, 1H). Mass (M + H): 144.0. |

TABLE 17-continued

| BX2 | 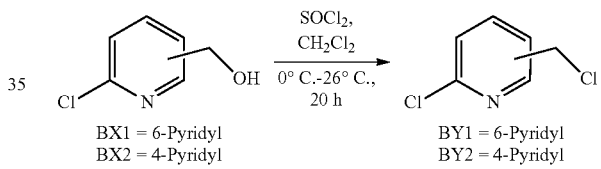 | Intermediate BW2 (2.5 g, 15.87 mmol) was reacted with NaBH4 (0.9 g, 23.80 mmol) and $BF_3\cdot O(Et)_2$ (3.9 mL, 31.74 mmol) in THF (100 mL) to give Intermediate BX2 (3.0 g, crude) as a colorless thick oil. $^1H$ NMR ($CDCl_3$): δ 8.35 (d, J = 4.87 Hz 1H), 7.36 (s, 1H), 7.21 (d, J = 5.85 Hz; 2H), 4.75 (d, J = 5.36 Hz; 2H). Mass (M + H): 144.0. |

Preparation of Intermediate BY

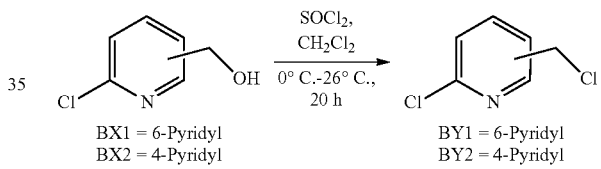

$SOCl_2$, $CH_2Cl_2$
0° C.-26° C., 20 h

BX1 = 6-Pyridyl
BX2 = 4-Pyridyl

BY1 = 6-Pyridyl
BY2 = 4-Pyridyl

To a cold solution of Intermediate BX (1.0 mmol) in dichloromethane (15 mL) at 0° C. was added slowly thionyl chloride (1.0 mmol) over 15 minutes. After the addition was complete, the reaction mixture was allowed to stir at room temperature for 20 hours. The reaction mixture was cooled, and ice cold water was added (30 mL). The mixture was extracted with dichloromethane (3×50 mL), washed with water (25 mL) and brine (25 mL), dried over anhydrous $Na_2SO_4$, and the solvent was removed to afford the crude Intermediate BY (Table 18), which was purified by column chromatography (silica gel 100-200 mesh) using 20% ethyl acetate in petroleum ether as the eluent.

TABLE 18

| BY1 | 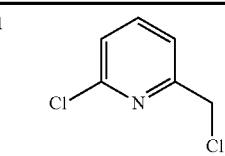 | Intermediate BX1 (1.3 g, 9.09 mmol) was reacted with thionyl chloride (0.66 mL, 13.98 mmol) in dichloromethane (30 mL) to give Intermediate BY1 (800 mg, 57%) as a pale brown solid. $^1H$ NMR ($CDCl_3$): δ 7.69 (t, J = 7.87 Hz; 1H), 7.43 (d, J = 7.46 Hz; 1H), 7.28 (d, J = 7.87 Hz; 1H), 4.63 (s, 2H). Mass (M + H): 161.9. |

TABLE 18-continued

| | | |
|---|---|---|
| BY2 | 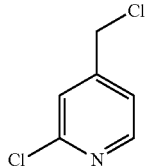 | Intermediate BX2 (2.0 g, 13.98 mmol) was reacted with thionyl chloride (1.0 mL, 13.98 mmol) in dichloromethane (30 mL) to give Intermediate BY2 (1.5 g, 68%) as a pale brown solid. $^1$H NMR (CDCl$_3$): δ 8.39 (d, J = 4.97 Hz; 1H), 7.38 (s, 1H), 7.25 (d, J = 4.56 Hz; 1H), 4.52 (s, 2H). Mass (M + H): 162.0. |

Preparation of Intermediate BZ

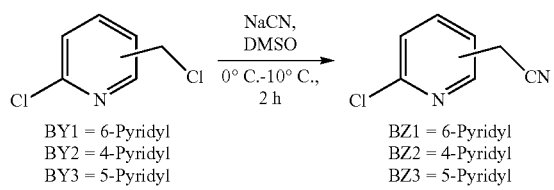

BY1 = 6-Pyridyl  BZ1 = 6-Pyridyl
BY2 = 4-Pyridyl  BZ2 = 4-Pyridyl
BY3 = 5-Pyridyl  BZ3 = 5-Pyridyl To a cold solution of Intermediate BY (1.0 mmol) in DMSO (10 mL) at 0° C. was added sodium cyanide (2.0 mmol) portionwise over 15 minutes. After the addition was complete, the reaction mixture was allowed to stir at 10° C. for 2 hours. Ice cold water was added to the reaction mixture (30 mL), and the mixture was extracted with ethyl acetate (3×50 mL), washed with water (25 mL) and brine (25 mL), dried over anhydrous Na$_2$SO$_4$, and the solvent was removed to afford the crude Intermediate BZ (Table 19), which was purified by column chromatography (silica gel 100-200 mesh) using 10% ethyl acetate in petroleum ether as the eluent.

TABLE 19

| | | |
|---|---|---|
| BZ1 | 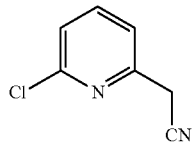 | Intermediate BY1 (800 mg, 4.93 mmol) was reacted with sodium cyanide (484 mg, 9.87 mmol) in DMSO (8 mL) to give Intermediate BZ1 (400 mg, 53%) as a pale brown solid, $^1$H NMR (CDCl$_3$): δ 7.73 (t, J = 7.81 Hz; 1H), 7.42 (d, J = 7.61 Hz; 1H), 7.33 (d, J = 8.00 Hz; 1H), 3.93 (s, 2H). Mass (M + H): 152.9. IR (cm$^{-1}$): 3079.79, 2923.5, 2252.12, 1439.39 and 789.42. |
| BZ2 | 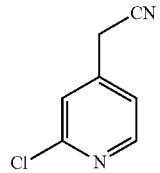 | Intermediate BY2 (1.5 g, 9.25 mmol) was reacted with sodium cyanide (0.9 g, 18.51 mmol) in DMSO (15 mL) to give Intermediate BZ2 (300 mg, 16.6%) as a pale brown solid. $^1$H NMR (CDCl$_3$): δ 8.43 (d, J = 5.07 Hz; 1H), 7.36 (s, 1H), 7.24 (d, J = 5.07 Hz; 1H), 3.78 (s, 2H). Mass (M + H): 153.0. IR (cm$^{-1}$): 2923.5, 2245.9, 1595.3, 1404.6 and 825.9. |
| BZ3 | 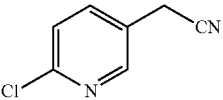 | Intermediate BY3 (1.5 g, 9.25 mmol) was reacted with sodium cyanide (0.9 g, 18.51 mmol) in DMSO (15 mL) to give Intermediate BZ3 (800 mg, 57%) as a pale brown solid. $^1$H NMR (CDCl$_3$): δ 8.37 (s, 1H), 7.68 (d, J = 8.29 Hz; 1H), 7.39 (s, J = 8.29 Hz; 1H), 7.25 (d, J = 4.56 Hz; 2H), 3.77 (s, 2H). Mass (M + H): 153.0. IR (cm$^{-1}$): 2923.5, 1439.3, 1108.8 and 789.4. |

Preparation of Intermediate CA

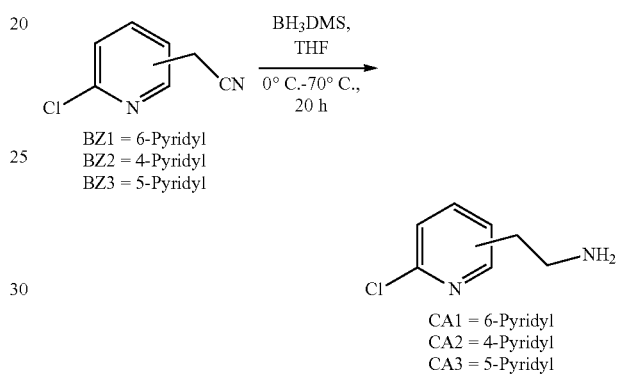

BZ1 = 6-Pyridyl
BZ2 = 4-Pyridyl
BZ3 = 5-Pyridyl

CA1 = 6-Pyridyl
CA2 = 4-Pyridyl
CA3 = 5-Pyridyl

To a cold solution of Intermediate BZ (1.0 mmol) in THF (30 mL) at 0° C. was BH$_3$.DMS (9.0 mmol) was added slowly over 5 minutes. After the addition was complete, the reaction mixture was allowed to reach room temperature and stirred for 20 hours. The reaction mixture was cooled in ice and then quenched with MeOH (5 mL). The reaction was then refluxed for 1 hour and concentrated. The residue was dissolved in ethyl acetate (50 mL), washed with water (2×10 mL) and brine solution (15 mL), dried over anhydrous Na$_2$SO$_4$, and the solvent was removed to afford the crude Intermediate CA (Table 20), which was in the next step without further purification.

TABLE 20

| | | |
|---|---|---|
| CA1 | 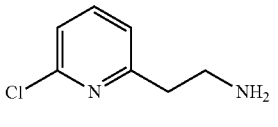 | Intermediate BZ1 (360 mg, 2.36 mmol) was reacted with BH$_3$•DMS (2.0 mL, 21.24 mmol) in THF (12 mL) to give Intermediate CA1 (250 mg, crude) as a pale brown gum. Mass (M + H): 157.0. |
| CA2 | 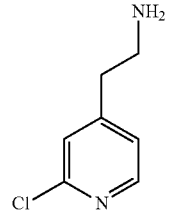 | Intermediate BZ2 (350 mg, 2.30 mmol) was reacted with BH$_3$•DMS (1.9 mL, 20.72 mmol) in THF (10 mL) to give Intermediate CA2 (350 mg, crude) as a pale brown gum Mass (M + H): 157.0. |

TABLE 20-continued

| | | |
|---|---|---|
| CA3 |  | Intermediate BZ3 (1.0 g, 6.57 mmol) was reacted with BH₃•DMS (5.6 mL, 59.13 mmol) in THF (30 mL) to give Intermediate CA3 (1 g, crude) as a pale brown gum. Mass (M + H): 157.0. |

Preparation of Intermediate CB

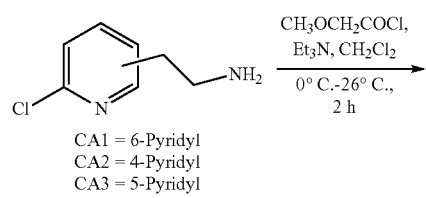

CA1 = 6-Pyridyl
CA2 = 4-Pyridyl
CA3 = 5-Pyridyl

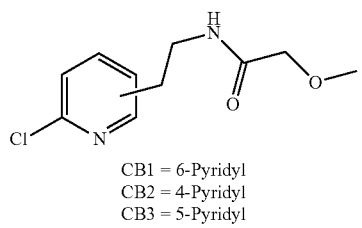

CB1 = 6-Pyridyl
CB2 = 4-Pyridyl
CB3 = 5-Pyridyl

To a cold (0° C.) solution of Intermediate CA (1.0 mmol) and triethylamine (2.0 mmol) in dichloromethane (20 mL) was added slowly methoxyacetyl chloride (1.1 mmol) over 5 minutes. After the addition was complete, the reaction mixture was allowed to reach room temperature and stirred for 4 hours. The reaction mixture was diluted with dichloromethane (10 mL), washed with water (2×15 mL) and brine (10 mL), dried over anhydrous Na₂SO₄, and the solvent was removed to afford the crude Intermediate CB (Table 21), which was purified by PREP-TLC plate using 5% MeOH in ethyl acetate as the eluent.

TABLE 21

| | | |
|---|---|---|
| CB1 | 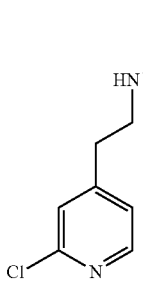 | Intermediate CA1 (370 mg, 2.37 mmol) was reacted with methoxyacetyl chloride (0.24 mL, 2.60 mmol) and Et₃N (0.67 mL, 4.74 mmol) in CH₂Cl₂ (10.0 mL) to give Intermediate CB1 (150 mg 27%) as a pale brown gum. ¹H NMR (CDCl₃): 7.58 (t, J = 7.6 Hz; 1H), 7.20 (d, J = 8.2 Hz; 1H), 7.11 (d, J = 7.4 Hz; 1H), 3.88 (s, 2H), 3.71 (t, J = 6.2 Hz; 2H), 3.40 (s, 3H), 3.0 (t, J = 6.4 Hz; 2H). Mass (M + H): 229.0. |

TABLE 21-continued

| | | |
|---|---|---|
| CB2 |  | Intermediate CA2 (360 mg, 2.30 mmol) was reacted with methoxyacetyl chloride (0.24 mL, 2.54 mmol) and Et₃N (0.65 mL, 4.61 mmol) in CH₂Cl₂ (10.0 mL) to give Intermediate CB2 (190 mg 35%) as a pale brown gum. ¹H NMR (CDCl₃): 8.31 (t, J = 4.9 Hz; 1H), 7.19 (s, 1H), 7.08 (d, J = 4.56 Hz; 1H), 6.61 (bs, 1H), 3.88 (s, 2H), 3.58 (t, J = 6.6 Hz; 2H), 3.38 (s, 3H), 2.86 (t, J = 7.2 Hz: 2H). Mass (M + H): 229.0. |
| CB3 | 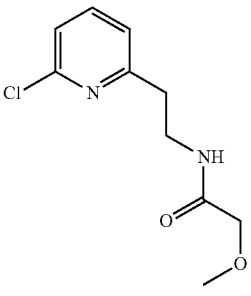 | Intermediate CA3 (1 g, 6.41 mmol) was reacted with methoxyacetyl chloride (0.65 mL, 7.05 mmol) and Et₃N (1.79 mL, 12.8 mmol) in CH₂Cl₂ (20.0 mL) to give Intermediate CB3 (700 mg 50%) as a pale brown gum. ¹H NMR (CDCl₃): δ 8.23 (d,, J = 2.48 Hz; 1H), 7.52 (dd, J = 8.2, 2.48 Hz; 1H), 7.28 (d, J = 7.87 Hz, 1H), 6.61 (bs, 1H), 3.87 (s, 2H), 3.55 (q, J = 6.6 Hz; 2H), 3.38 (s, 3H), 3.00 (t, J = 6.42 Hz; 2H). Mass (M + H): 229.0. |

Preparation of Compounds (33)-(35)

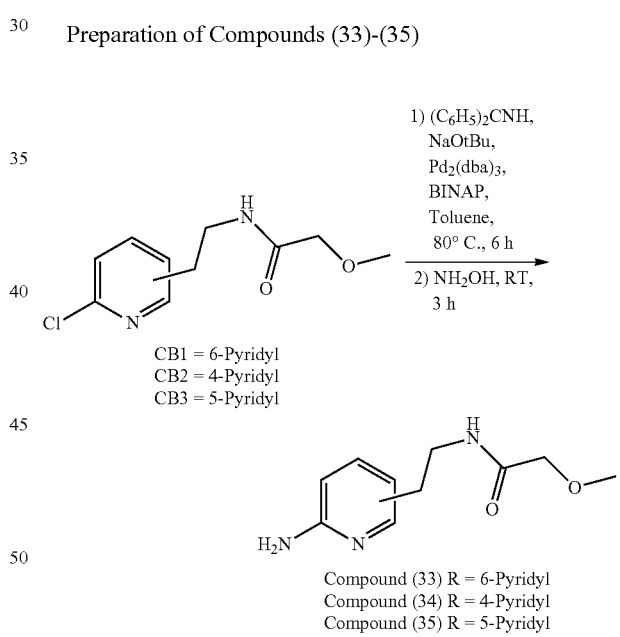

CB1 = 6-Pyridyl
CB2 = 4-Pyridyl
CB3 = 5-Pyridyl 1) (C₆H₅)₂CNH, NaOtBu, Pd₂(dba)₃, BINAP, Toluene, 80° C., 6 h
2) NH₂OH, RT, 3 h Compound (33) R = 6-Pyridyl
Compound (34) R = 4-Pyridyl
Compound (35) R = 5-Pyridyl To a solution of Intermediate CB (1.0 mmol) in toluene (10 mL) were added sequentially NaOtBu (1.4 mmol), (±) BINAP (0.02 mmol), Pd₂(dba)₃ (0.01 mmol), and benzophenone imine (1.2 mmol). The mixture was degassed with argon for 30 minutes and stirred at 80° C. for 6 hours. The reaction mixture was concentrated, and the crude imine was purified by column chromatography (silica gel 100-200 mesh) using 20% MeOH in chloroform as the eluent. The resulting intermediate was dissolved in MeOH (15 mL), and a hydroxylamine solution (50% in water; 1.2 mmol) was added, and the mixture was stirred at room temperature for 3 hours. The reaction mixture was concentrated; the resulting aqueous residue was then diluted with water (10 mL) and extracted ethyl acetate (2×15 mL). The combined ethyl acetate layers were washed with water (10 mL) and brine (15 mL), dried over anhydrous Na$_2$SO$_4$, and the solvent was removed to afford the crude product, which was purified using PREP TLC by eluting with 3% MeOH in chloroform. The product amine was treated with EtOAc.HCl and Compounds (33)-(35) were obtained as the corresponding HCl salt (Table 22).

TABLE 22

| | | |
|---|---|---|
| (33) | 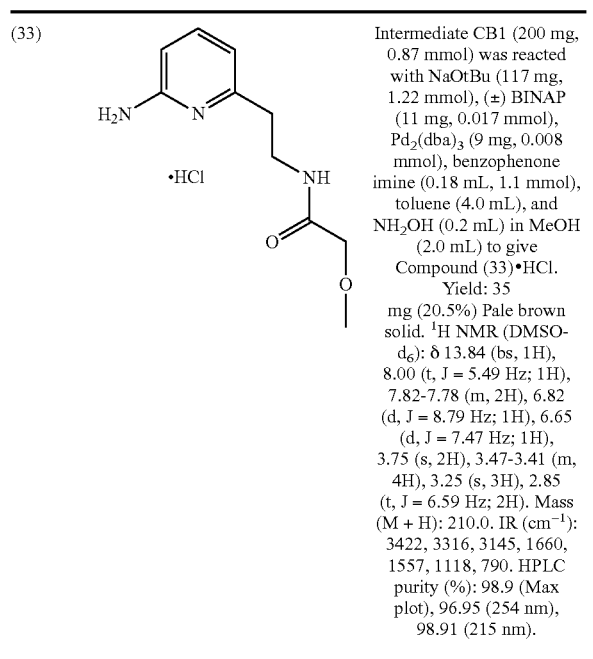 | Intermediate CB1 (200 mg, 0.87 mmol) was reacted with NaOtBu (117 mg, 1.22 mmol), (±) BINAP (11 mg, 0.017 mmol), Pd$_2$(dba)$_3$ (9 mg, 0.008 mmol), benzophenone imine (0.18 mL, 1.1 mmol), toluene (4.0 mL), and NH$_2$OH (0.2 mL) in MeOH (2.0 mL) to give Compound (33)•HCl. Yield: 35 mg (20.5%) Pale brown solid. $^1$H NMR (DMSO-d$_6$): δ 13.84 (bs, 1H), 8.00 (t, J = 5.49 Hz; 1H), 7.82-7.78 (m, 2H), 6.82 (d, J = 8.79 Hz; 1H), 6.65 (d, J = 7.47 Hz; 1H), 3.75 (s, 2H), 3.47-3.41 (m, 4H), 3.25 (s, 3H), 2.85 (t, J = 6.59 Hz; 2H). Mass (M + H): 210.0. IR (cm$^{-1}$): 3422, 3316, 3145, 1660, 1557, 1118, 790. HPLC purity (%): 98.9 (Max plot), 96.95 (254 nm), 98.91 (215 nm). |
| (34) | 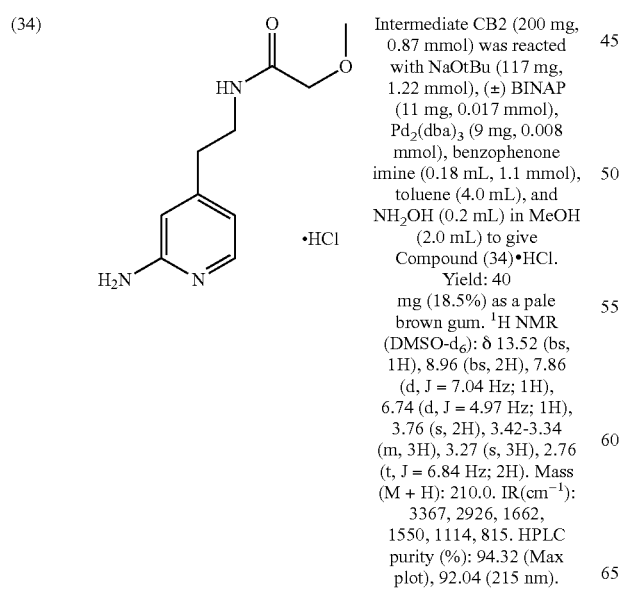 | Intermediate CB2 (200 mg, 0.87 mmol) was reacted with NaOtBu (117 mg, 1.22 mmol), (±) BINAP (11 mg, 0.017 mmol), Pd$_2$(dba)$_3$ (9 mg, 0.008 mmol), benzophenone imine (0.18 mL, 1.1 mmol), toluene (4.0 mL), and NH$_2$OH (0.2 mL) in MeOH (2.0 mL) to give Compound (34)•HCl. Yield: 40 mg (18.5%) as a pale brown gum. $^1$H NMR (DMSO-d$_6$): δ 13.52 (bs, 1H), 8.96 (bs, 2H), 7.86 (d, J = 7.04 Hz; 1H), 6.74 (d, J = 4.97 Hz; 1H), 3.76 (s, 2H), 3.42-3.34 (m, 3H), 3.27 (s, 3H), 2.76 (t, J = 6.84 Hz; 2H). Mass (M + H): 210.0. IR(cm$^{-1}$): 3367, 2926, 1662, 1550, 1114, 815. HPLC purity (%): 94.32 (Max plot), 92.04 (215 nm). |
| (35) | 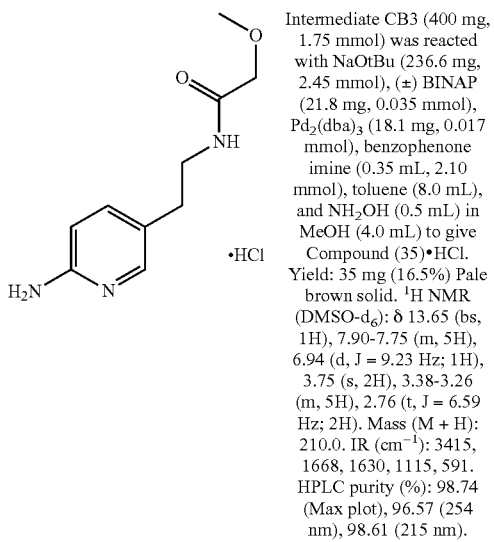 | Intermediate CB3 (400 mg, 1.75 mmol) was reacted with NaOtBu (236.6 mg, 2.45 mmol), (±) BINAP (21.8 mg, 0.035 mmol), Pd$_2$(dba)$_3$ (18.1 mg, 0.017 mmol), benzophenone imine (0.35 mL, 2.10 mmol), toluene (8.0 mL), and NH$_2$OH (0.5 mL) in MeOH (4.0 mL) to give Compound (35)•HCl. Yield: 35 mg (16.5%) Pale brown solid. $^1$H NMR (DMSO-d$_6$): δ 13.65 (bs, 1H), 7.90-7.75 (m, 5H), 6.94 (d, J = 9.23 Hz; 1H), 3.75 (s, 2H), 3.38-3.26 (m, 5H), 2.76 (t, J = 6.59 Hz; 2H). Mass (M + H): 210.0. IR (cm$^{-1}$): 3415, 1668, 1630, 1115, 591. HPLC purity (%): 98.74 (Max plot), 96.57 (254 nm), 98.61 (215 nm). |

Synthesis of Compounds (36)-(39)

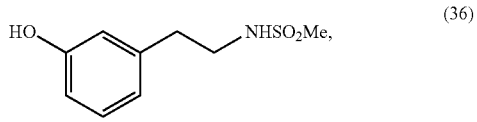

(36)

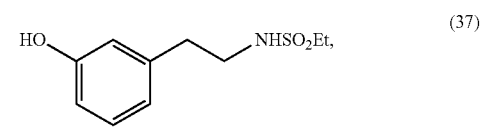

(37)

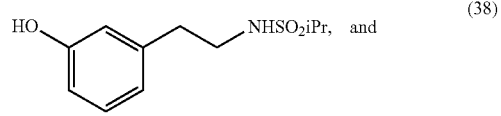

(38)

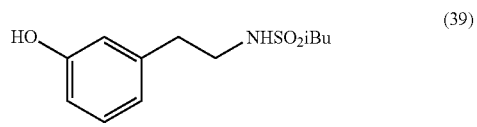

(39)

Compounds (36)-(39) were synthesized according to the procedure shown in Scheme 26.

Scheme 26

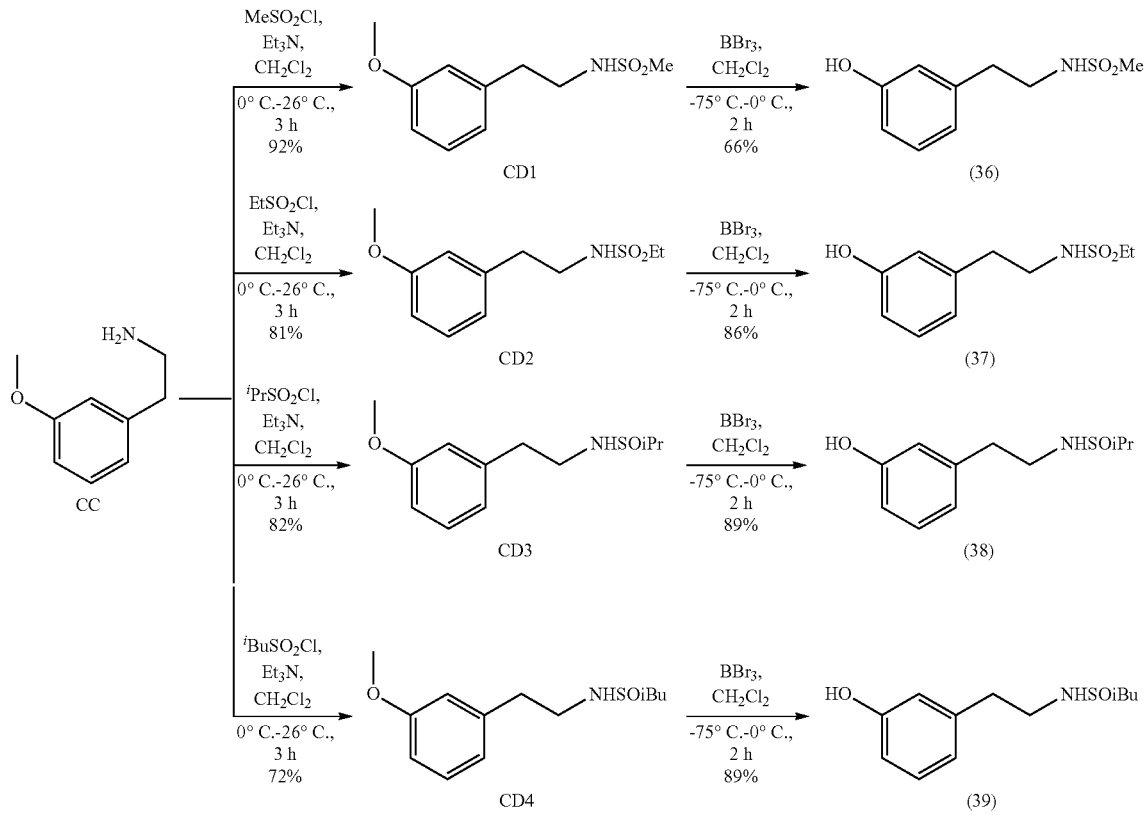

Preparation of Intermediate CD

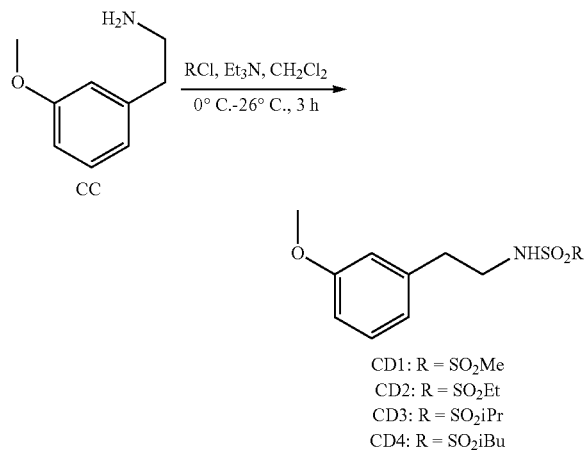

To a cold (0° C.) solution of Intermediate CC (1.0 mmol) and triethylamine (1.2 mmol) in dichloromethane (20 mL) was added slowly the requisite sulfonyl chloride (1.2 mmol) over 5 minutes. After the addition was complete, the reaction mixture was allowed to reach room temperature and stirred for 3 hours. The reaction mixture was then diluted with dichloromethane (25 mL), washed with water (2×25 mL) and brine (20 mL), dried over anhydrous $Na_2SO_4$, and the solvent was removed to afford the crude Intermediate CD (Table 23), which was purified by column chromatography (silica gel 100-200 mesh) using 2% MeOH in chloroform as the eluent.

TABLE 23

| CD1 | Intermediate CC (250 mg, 1.65 mmol) was reacted with methanesulfonyl chloride (0.15 mL, 1.92 mmol) and $Et_3N$ (0.28 mL, 1.99 mmol) in $CH_2Cl_2$ (5.0 mL) to give Intermediate CD1 (350 mg, 92%) as a pale brown oil. $^1$H NMR ($CDCl_3$): 7.24 (m, 1H), 6.80-6.75 (m, 3H), 4.22 (bs, 1H), 3.80 (s, 3H), 3.43-3.38 (m, 2H), 2.87-2.84 (m, 5H). Mass (M + H): 230.0. |
|---|---|
| CD2 | Intermediate CC (250 mg, 1.65 mmol) was reacted with ethanesulfonyl chloride (0.18 mL, 1.89 mmol) and $Et_3N$ (0.27 mL, 1.92 mmol) in $CH_2Cl_2$ (5.0 mL) to give Intermediate CD2 (320 mg, 81%) as a pale brown oil. $^1$H NMR ($CDCl_3$): 7.26-7.22 (m, 1H), 6.81-6.75 (m, 3H), 4.05 (bs, 1H), 3.80 (s, 3H), 3.41-3.36 (m, 2H), 2.97 (q, 2H), 2.85(t, J = 6.6 Hz; 2H), 1.26 (t, J = 6.6 Hz; 3H). Mass (M − H): 242.0. |

TABLE 23-continued

| | | |
|---|---|---|
| CD3 | (structure: 3-methoxyphenethyl-NH-SO2-iPr) | Intermediate CC (250 mg, 1.65 mmol) was reacted with isopropylsulfonyl chloride (0.22 mL, 1.96 mmol) and Et$_3$N (0.28 mL, 1.97 mmol) in CH$_2$Cl$_2$ (5.0 mL) to give Intermediate CD3 (340 mg, 82%) as a pale brown oil. $^1$H NMR (CDCl$_3$): 7.24 (t, J = 7.5 Hz; 1H), 6.80-6.75 (m, 3H), 3.98 (bs, 1H), 3.80 (s, 3H), 3.39 (q, 2H), 3.12-3.08 (m, 1H), 2.85 (t, J = 6.8 Hz; 2H), 1.32 (s, 3H), 1.30 (s, 3H),. Mass (M − H): 242.1. Mass (M + H): 258.0. |
| CD4 | (structure: 3-methoxyphenethyl-NH-SO2-iBu) | Intermediate CC (100 mg, 0.66 mmol) was reacted with isobutylsulfonyl chloride (0.11 mL, 0.78 mmol) and triethylamine (0.11 mL, 0.78 mmol) in dichloromethane (5.0 mL) to give Intermediate CD4 (130 mg, 72%) as a pale brown oil. $^1$H NMR (CDCl$_3$): 7.24 (t, J = 7.8 Hz; 1H), 6.80-6.74 (m, 3H), 4.15 (bs, 1H), 3.80 (s, 3H), 3.37 (q, 2H), 2.86-2.80 (m, 4H), 2.17 (m, 1H), 1.06 (s, 3H), 1.04 (s, 3H). Mass (M + H): 272.0. |

Preparation of Compounds (36)-(39)

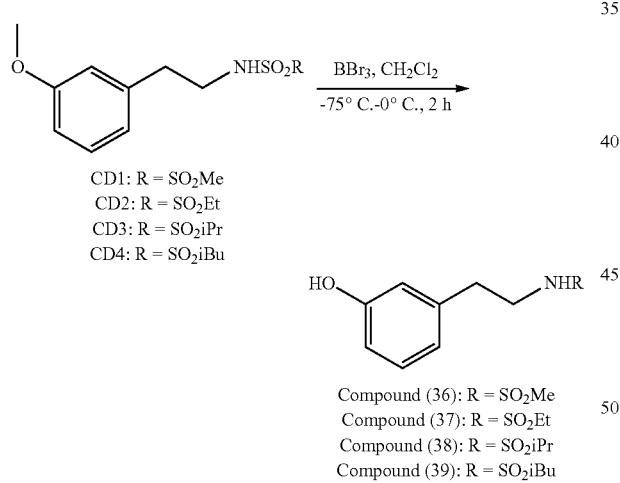

CD1: R = SO$_2$Me
CD2: R = SO$_2$Et
CD3: R = SO$_2$iPr
CD4: R = SO$_2$iBu

Compound (36): R = SO$_2$Me
Compound (37): R = SO$_2$Et
Compound (38): R = SO$_2$iPr
Compound (39): R = SO$_2$iBu To a cold (−70° C.) solution of Intermediate CD (1.0 mmol) in dichloromethane (20 mL) was added slowly BBr$_3$ (1.3 mmol). After the addition was complete, the reaction mixture was allowed to reach 0° C. and stirred for 2 hours. The reaction mixture was quenched with ice cold water (15 mL) and extracted with dichloromethane (2×30 mL). The combined dichloromethane layers were washed with water (2×10 mL) and brine (20 mL), dried over anhydrous Na$_2$SO$_4$, and the solvent was removed to afford the crude product (Table 24). This material was then purified by column chromatography (silica gel 100-200 mesh) using 40% ethyl acetate in petroleum ether as the eluent to afford the desired product.

TABLE 24

| | | |
|---|---|---|
| (36) | (structure: 3-hydroxyphenethyl-NH-SO2-Me) | Intermediate CD1 (350 mg, 1.52 mmol) was reacted with BBr$_3$ (0.18 mL, 1.89 mmol) in dichloromethane (6.0 mL) to give Compound (36) (220 mg, 66%) as a pale brown gum. $^1$H NMR (CDCl$_3$): δ 7.19 (t, J = 7.80 Hz; 1H), 6.78-6.69 (m, 3H), 4.81 (s, 1H), 4.19 (bs, 1H), 3.42-3.38 (m, 2H), 2.88-2.81 (m, 5H). Mass (M − H): 214.0. IR (cm$^{-1}$): 3434, 2930, 1597, 1311, 1144, 973, 521. HPLC purity (%): 97.01 (Max plot), 96.81 (215 nm). |
| (37) | (structure: 3-hydroxyphenethyl-NH-SO2-Et) | Intermediate CD2 (320 mg, 1.31 mmol) was reacted with BBr$_3$ (0.16 mL, 1.68 mmol) in dichloromethane (5.0 mL) to give Compound (37) (260 mg, 86%) as a pale brown oil. $^1$H NMR (CDCl$_3$): δ 7.18 (t, J = 7.71 Hz; 1H), 6.76-6.71 (m, 3H), 5.43 (s, 1H), 4.28 (t, J = 5.85 Hz; 1H), 3.39-3.34 (m, 2H), 2.98-2.93 (m, 2H), 2.84-2.79 (m, 2H), 1.27 (t, J = 7.32 Hz; 3H),. Mass (M − H): 214.0. IR (cm$^{-1}$): 3402, 3294, 2931, 1589, 1456, 1312, 1137, 869, 697. HPLC purity (%): 97.63 (Max plot), 97.04 (215 nm). |
| (38) | (structure: 3-hydroxyphenethyl-NH-SO2-iPr) | Intermediate CD3 (340 mg, 1.32 mmol) was reacted with BBr$_3$ (0.16 mL, 1.71 mmol) in dichloromethane (5.0 mL) to give Compound (38) (285 mg, 89%) as a pale brown oil. $^1$H NMR (CDCl$_3$): δ 7.19 (t, J = 7.87 Hz; 1H), 6.79-6.70 (m, 3H), 4.86 (s, 1H), 3.95 (bs, 1H), 3.41-3.36 (q, 2H), 3.12-3.09 (m, 1H), 2.83 (t, J = 6.63 Hz; 2H), 1.32 (s, 3H), 1.30 (s, 3H),. Mass (M − H): 242.1. IR (cm$^{-1}$): 3414, 2928, 1589, 1456, 1308, 1132, 885, 783, 696. HPLC purity (%): 94.44 (Max plot), 93.92 (215 nm). |

TABLE 24-continued

| (39) | Intermediate CD4 (130 mg, 0.47 mmol) was reacted with BBr₃ (0.06 mL, 0.61 mmol) in dichloromethane (5.0 mL) to give Compound (39) (110 mg, 89%) as a pale brown oil. $^1$H NMR (CDCl₃): δ 7.19 (t, 1H), 6.69 (m, 3H), 4.83 (s, 1H), 4.05 (t, 1H), 3.38 (q, 2H), 2.84-2.81 (m, 4H), 2.2 (m, 1H), 1.06 (s, 3H), 1.05 (s, 3H),. Mass (M − H): 256.1. IR (cm$^{-1}$): 3413, 2963, 1589, 1457, 1308, 1139, 869, 784, 696. HPLC purity (%): 97.14 (Max plot), 97.28 (215 nm). |
|---|---|

Screening Conditions for Identifying SPR Inhibition

The compounds described herein were screened for activity as inhibitors of Sepiapterin Reductase (SPR).

Protein Production

His-tagged recombinant human SPR (GenBank accession number: NM_003124) was cloned as synthetic gene and expressed in *E. coli* Rosetta 2 strain. Bacteria were grown at 37° C., and expression of SPR protein was induced for 4 hours. After cell lysis, the His-tagged SPR protein was affinity purified with a TALON column (purity of the isolated SPR protein is >95%). In an initial quality control, the enzymatic activity of recombinant SPR was confirmed with a chromogenic assay (read-out OD at 420 nm).

Primary Screen

To screen for SPR inhibition, a biochemical assay based on LC/MS (and chromogenic) read-out has been developed. The LC/MS assay monitors the product formation (L-biopterin) and the chromogenic assay measures OD at 420 nm.

N-methoxyacetyl serotonin was used as a reference compound (positive control). The IC$_{50}$ measured using the screening conditions was 20-40 nM, which agrees with the literature (Smith et al., *Journal of Biological Chemistry*, 297:5601, 1992).

The exemplary assay protocol uses the following conditions: SPR (6 nM); L-Sepiapterin (50 µM); NADPH (100 µM); Na-Phosphate buffer, pH 6.5 (100 mM); 82 µL assay volume; 60 minutes incubation with compounds (0.5% final concentration in DMSO) at 37° C. in Greiner µClear® 384 well plates.

The following experimental procedure was applied:
(1) Add 2 µL compound (inhibitor) dilutions (20% DMSO) in Greiner µClear® 384 well plates.
(2) Add 40 µL enzyme/assay buffer.
(3) Start: 40 µL substrate solution/assay buffer.
(4) Final: 82 µL assay solution.
(5) Incubation: Safire 1 hour at 37° C. and measuring after 1 hour using OD at 420 nm (chromogenic read-out).
(6) Transfer 50 µL to a 384 Matrix flat bottom (clear) for LC/MS measurement.
(7) Stop: add 5 µL 1M HCl and 10 µL of 0.1 M I₂/NaI solution.
(8) Incubation: 45 minutes at 37° C.
(9) Neutralization: 10 µL 0.1 M ascorbic acid and 5 µL 1 N NaOH.
(10) LC/MS measurement.

If desired, the compounds can be been further screened using an 8 point dilution series to validate the results. For example, the compounds of Table 1 were screened using this additional method in triplicate. These tests were performed at the following concentrations:

Most potent: 0.2-0.7-2.1-6.2-18.5-55.6-166.7-500 nM
Medium potent: 0.002-0.007-0.02-00.6-0.02-0.7-1.7-5 µM
Less potent: 0.02-0.07-0.2-0.6-1.9-5.6-16.7-50 µM A robust performance of the SPR assay was achieved throughout the screen, resulting in a mean Z'-value of 0.93 (chromogenic) and 0.82 (LC/MS), and the inhibitors showed the expected response in the LC/MS (chromogenic) assay.

Screening of the compounds has been performed at three concentrations (20 nM, 200 nM, and 2000 nM) in singletons (0.5% final concentration in DMSO). Z' was 0.91 and 0.81 for the chromogenic and the LC/MS measurements, respectively. The screens showed that compounds of Formulas (I) and (II) can inhibit SPR, even at the lower concentrations. For example, at the 20 nM concentration, up to 77% inhibition of enzyme activity was observed. Exemplary IC$_{50}$ values are presented in Table 25.

TABLE 25

| No. | Structure | IC$_{50}$ chromogenic [µM] | IC$_{50}$ LC/MS [µM] |
|---|---|---|---|
| control | N-Methoxyacetyl-Serotonin | 0.042 | 0.043 |
| (1) | 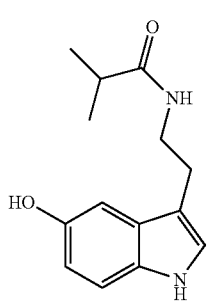 [SMILES: CC(C)C(=O)NCCc1c[nH]c2ccc(O)cc12] | 0.40 | 0.33 |

TABLE 25-continued

| No. | Structure | IC$_{50}$ chromogenic [μM] | IC$_{50}$ LC/MS [μM] |
|---|---|---|---|
| (2) | 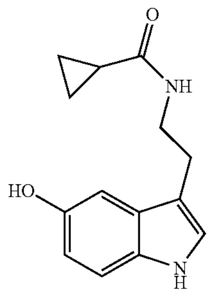 [SMILES: O=C(NCCc1c[nH]c2ccc(O)cc12)C1CC1] | 0.36 | 0.34 |
| (3) | 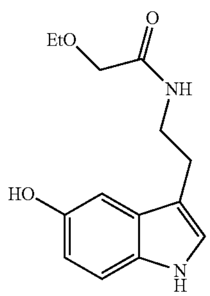 | 2.8 | 2.2 |
| (16) | 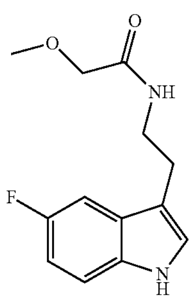 [SMILES: COCC(=O)NCCc1c[nH]c2ccc(F)cc12] | 3.4 | 2.8 |
| (17) | 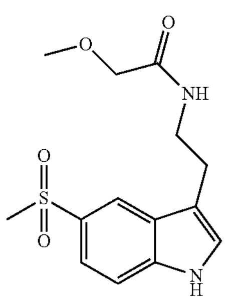 [SMILES: COCC(=O)NCCc1c[nH]c2ccc(S(C)(=O)=O)cc12] | 4.5 | 3.2 |
| (18) | 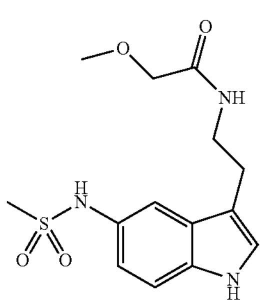 [SMILES: COCC(=O)NCCc1c[nH]c2ccc(NS(C)(=O)=O)cc12] | 1.1 | 1.0 |

TABLE 25-continued

| No. | Structure | IC$_{50}$ chromogenic [μM] | IC$_{50}$ LC/MS [μM] |
| --- | --- | --- | --- |
| (21) | 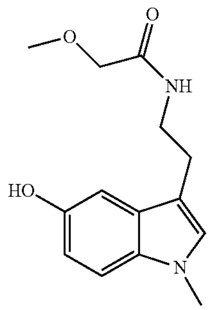 [SMILES: COCC(=O)NCCc1cn(C)c2ccc(O)cc12] | 0.084 | 0.086 |
| (22) | 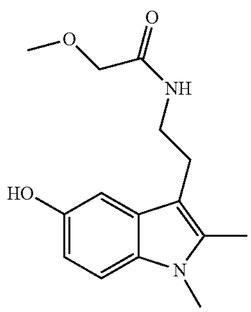 [SMILES: COCC(=O)NCCc1c(C)n(C)c2ccc(O)cc12] | 0.011 | 0.019 |
| (23) | 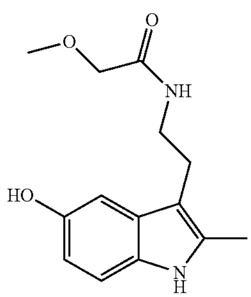 [SMILES: COCC(=O)NCCc1c(C)[nH]c2ccc(O)cc12] | 0.011 | 0.012 |
| (24) | 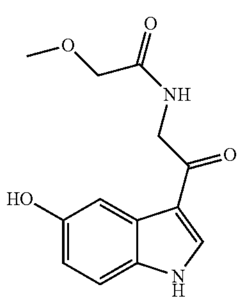 [SMILES: COCC(=O)NCC(=O)c1c[nH]c2ccc(O)cc12] | 0.31 | 0.31 |
| (32) | 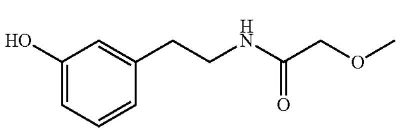 | 0.064 | 0.069 |

TABLE 25-continued

| No. | Structure | IC$_{50}$ chromogenic [μM] | IC$_{50}$ LC/MS [μM] |
|---|---|---|---|
| (12) | 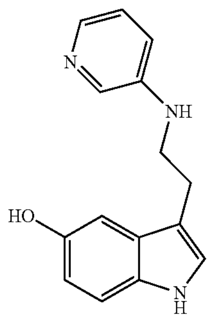 [SMILES: Oc1ccc2[nH]cc(CCNc3cccnc3)c2c1] | 2.1 | 1.6 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A compound of Formula (1):

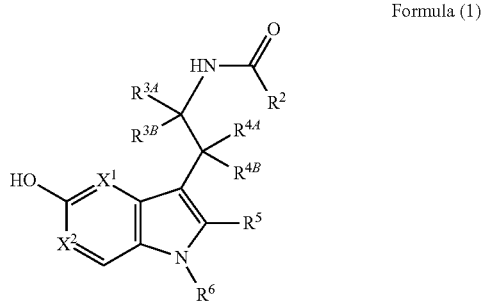

Formula (1)

wherein, $X^1$ and $X^2$ are independently selected from N, C—H, and C-halogen;

$R^2$ is CH$_2$OR$^{2A}$ or C$_{1-6}$ alkyl;

$R^{2A}$ is H or C$_{1-6}$ alkyl;

$R^{3A}$ and $R^{3B}$ are both H;

$R^{4A}$ and $R^{4B}$ are both H; and $R^5$ and $R^6$ are independently selected from the group consisting of H and C$_{1-6}$ alkyl wherein the alkyl may be unsubstituted or substituted one or more times with groups independently selected from the group consisting of: C$_{1-6}$ alkyl, C$_{2-6}$ alkenyl, C$_{2-6}$ alkynyl, cycloalkyl, cycloalkenyl, heterocyclyl, aryl, heteroaryl, halogen; azido(—N$_3$), nitro (—NO$_2$), cyano (—CN), acyloxy(—OC(═O)R'), acyl (—C(═O)R'), alkoxy (—OR'), amido (—NR'C(═O)R" or —C(═O)NRR'), amino (—NRR'), carboxylic acid (—CO$_2$H), carboxylic ester (—CO$_2$R'), carbamoyl (—OC(═O)NR'R" or —NRC(═O)OR'), hydroxy (—OH), isocyano (—NC), sulfonate (—S(═O)$_2$OR), sulfonamide (—S(═O)$_2$NRR' or —NRS(═O)$_2$R'), or sulfonyl (—S(═O)$_2$R), where each R or R' is selected, independently, from H, C$_{1-6}$ alkyl, C$_{2-6}$ alkenyl, C$_{2-6}$ alkynyl, cycloalkyl, heterocyclyl, aryl, and heteroaryl;

or the compound is a pharmaceutically acceptable salt thereof.

2. The compound of claim 1, wherein one or both of $X^1$ and $X^2$ is C—H.

3. The compound of claim 1, wherein both of $X^1$ and $X^2$ are C—H.

4. A compound of Formula (I):

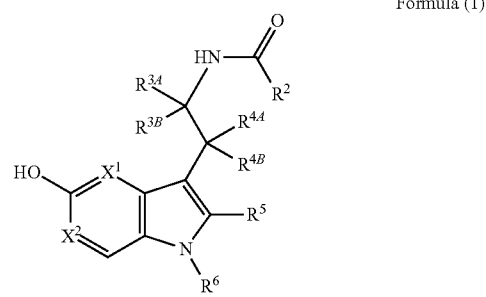

Formula (1)

wherein, one or both of $X^1$ and $X^2$ is C—Cl;

$R^2$ is CH$_2$OR$^{2A}$ or C$_{1-6}$ alkyl;

$R^{2A}$ is H or C$_{1-6}$ alkyl;

$R^{3A}$ and $R^{3B}$ are both H;

$R^{4A}$ and $R^{4B}$ are both H; and $R^5$ and $R^6$ are independently selected from the group consisting of H and C$_{1-6}$ alkyl;

wherein said C$_{1-6}$ alkyl may be unsubstituted or substituted one or more times with groups independently selected from the group consisting of: C$_{1-6}$ alkyl, C$_{2-6}$ alkenyl, C$_{2-6}$ alkynyl, cycloalkyl, cycloalkenyl, heterocyclyl, aryl, heteroaryl, halogen; azido(—N$_3$), nitro (—NO$_2$), cyano (—CN), acyloxy(—OC(═O)R'), acyl (—C(═O)R'), alkoxy (—OR'), amido (—NR'C(═O)R" or —C(═O)NRR'), amino (—NRR'), carboxylic acid (—CO$_2$H), carboxylic ester (—CO$_2$R'), carbamoyl (—OC(═O)NR'R" or —NRC(═O)OR'), hydroxy (—OH), isocyano (—NC), sulfonate (—S(═O)$_2$OR), sulfonamide (—S(═O)$_2$NRR' or —NRS(═O)$_2$R'), or sulfonyl (—S(═O)$_2$R), where each R or R' is selected, independently, from H, $C_{1-6}$ alkyl, $C_{2-6}$ alkenyl, $C_{2-6}$ alkynyl, cycloalkyl, heterocyclyl, aryl, and heteroaryl; or the compound is a pharmaceutically acceptable salt thereof.

5. The compound of claim 3, wherein $R^5$ and $R^6$ are independently selected from H and $CH_3$.

6. A compound of Formula (1):

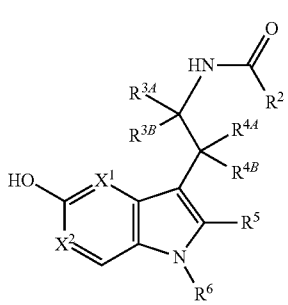

Formula (1)

wherein, $X^1$ and $X^2$ are independently selected from N, C—H, and C-halogen;

$R^2$ is $CH_2OR^{2A}$;

$R^{2A}$ is H or $C_{1-6}$ alkyl;

$R^{3A}$ and $R^{3B}$ are both H;

$R^{4A}$ and $R^{4B}$ are both H; and $R^5$ and $R^6$ are independently selected from the group consisting of H and $C_{1-6}$ alkyl;

wherein the $C_{1-6}$ alkyl may be unsubstituted or substituted one or more times with groups independently selected from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, halogen; azido(—$N_3$), nitro (—$NO_2$), cyano (—CN), acyloxy(—OC(=O)R'), acyl (—C(=O)R'), alkoxy (—OR'), amido (—NR'C(=O)R'' or —C(=O)NRR'), amino (—NRR'), carboxylic acid (—$CO_2H$), carboxylic ester (—$CO_2R'$), carbamoyl (—OC(=O)NR'R'' or —NRC(=O)OR'), hydroxy (—OH), isocyano (—NC), sulfonate (—S(=O)$_2$OR), sulfonamide (—S(=O)$_2$NRR' or —NRS(=O)$_2R'$), or sulfonyl (—S(=O)$_2R$), where each R or R' is selected, independently, from H, $C_{1-6}$ alkyl, $C_{2-6}$ alkenyl, $C_{2-6}$ alkynyl, cycloalkyl, heterocyclyl, aryl, and heteroaryl; or the compound is a pharmaceutically acceptable salt thereof.

7. A compound of Formula (1):

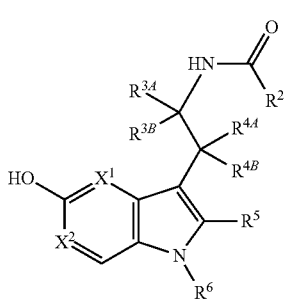

Formula (1)

wherein, both of $X^1$ and $X^2$ is C—H;

$R^2$ is $CH_2OR^{2A}$;

$R^{2A}$ is H or $C_{1-6}$ alkyl;

$R^{3A}$ and $R^{3B}$ are both H;

$R^{4A}$ and $R^{4B}$ are both H; and $R^5$ and $R^6$ are independently selected from the group consisting of H and $C_{1-6}$ alkyl;

wherein the aid $C_{1-6}$ alkyl may be unsubstituted or substituted one or more times with groups independently selected from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, halogen; azido(—$N_3$), nitro (—$NO_2$), cyano (—CN), acyloxy(—OC(=O)R'), acyl (—C(=O)R'), alkoxy (—OR'), amido (—NR'C(=O)R'' or —C(=O)NRR'), amino (—NRR'), carboxylic acid (—$CO_2H$), carboxylic ester (—$CO_2R'$), carbamoyl (—OC(=O)NR'R'' or —NRC(=O)OR'), hydroxy (—OH), isocyano (—NC), sulfonate (—S(=O)$_2$OR), sulfonamide (—S(=O)$_2$NRR' or —NRS(=O)$_2R'$), or sulfonyl (—S(=O)$_2R$), where each R or R' is selected, independently, from H, $C_{1-6}$ alkyl, $C_{2-6}$ alkenyl, $C_{2-6}$ alkynyl, cycloalkyl, heterocyclyl, aryl, and heteroaryl; or the compound is a pharmaceutically acceptable salt thereof.

8. A compound selected from:

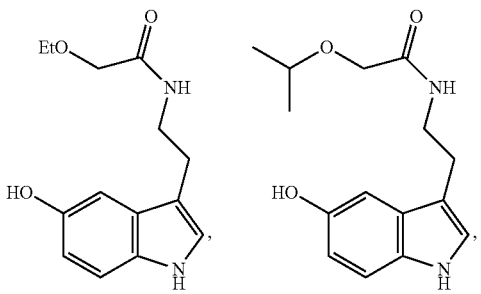

9. A compound selected from:

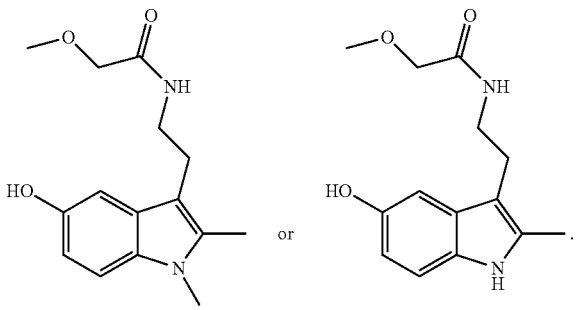 [SMILES: COCC(=O)NCCc1c(C)n(C)c2ccc(O)cc12 ; COCC(=O)NCCc1c(C)[nH]c2ccc(O)cc12]

or

10. A compound of Formula I-B:

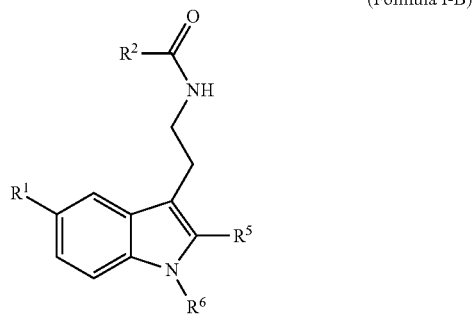

(Formula I-B)

wherein,
$R^1$ is OH;
$R^2$ is $C_{3-6}$ alkyl;
$R^5$ is $CH_3$; and
$R^6$ is independently selected from the group consisting of H or $C_{1-3}$ alkyl;
wherein the $C_{3-6}$ or $C_{1-3}$ alkyl may be unsubstituted or substituted one or more times with groups independently selected from the group consisting of: $C_{1-6}$ alkyl, $C_{2-6}$ alkenyl, $C_{2-6}$ alkynyl, cycloalkyl, cycloalkenyl, heterocyclyl, aryl, heteroaryl, halogen; azido(—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, cycloalkyl, heterocyclyl, aryl, and heteroaryl.

11. The compound of claim 1, wherein said compound is an inhibitor of Sepiapterin Reductase (SPR).

12. A pharmaceutical composition comprising the compound of claim 1, or a prodrug or pharmaceutically acceptable salt thereof, and a pharmaceutically acceptable excipient.

13. A method of treating or reducing pain in a mammal, wherein said method comprises the administration of the compound of claim 1, or a prodrug or pharmaceutically acceptable salt thereof to the mammal in a dosage sufficient to inhibit SPR.

14. The method of claim 13, wherein said pain is neuropathic, inflammatory, nociceptive, or functional pain.

15. The method of claim 13, wherein said pain is chronic pain.

16. The method of claim 13, wherein said pain is acute pain.

* * * * *